(12) United States Patent
Sugiyama et al.

(10) Patent No.: US 6,545,009 B1
(45) Date of Patent: Apr. 8, 2003

(54) RETINOID-RELATED RECEPTOR FUNCTION REGULATING AGENT

(75) Inventors: Yasuo Sugiyama, Kawanishi (JP); Yu Momose, Takarazuka (JP); Hiroyuki Kimura, Sakai (JP); Junichi Sakamoto, Toyonaka (JP); Hiroyuki Odaka, Kobe (JP)

(73) Assignee: Takeda Chemical Industries, Ltd., Osaka (JP)

( * ) Notice: Subject to any disclaimer, the term of this patent is extended or adjusted under 35 U.S.C. 154(b) by 0 days.

(21) Appl. No.: 09/720,644

(22) PCT Filed: Jun. 30, 1999

(86) PCT No.: PCT/JP99/03520

§ 371 (c)(1),
(2), (4) Date: Dec. 28, 2000

(87) PCT Pub. No.: WO00/01679

PCT Pub. Date: Jan. 13, 2000

(30) Foreign Application Priority Data

Jul. 1, 1998 (JP) .......................... 10-186698

(51) Int. Cl.$^7$ .................... A61K 31/435; A61K 31/425; C07D 277/30; C07D 233/54; C07D 401/04

(52) U.S. Cl. ................. 514/277; 514/365; 514/374; 514/396; 546/256; 548/204; 548/236; 548/341.5

(58) Field of Search ..................... 546/256; 514/277, 514/365, 374, 396; 548/204, 236, 341.5

(56) References Cited

U.S. PATENT DOCUMENTS

| | | |
|---|---|---|
| 3,840,548 A | 10/1974 | Malen et al. |
| 3,939,115 A | 2/1976 | Wang et al. |
| 4,001,420 A | 1/1977 | Malen et al. |
| 4,043,973 A | 8/1977 | Wang et al. |
| 4,164,480 A | 8/1979 | Irick, Jr. et al. |
| 5,061,705 A | 10/1991 | Wuest et al. |
| 5,342,851 A | 8/1994 | Sanfilippo et al. |
| 5,595,685 A | 1/1997 | Takiguchi et al. |
| 5,639,770 A | 6/1997 | Chihiro et al. |
| 5,643,932 A | 7/1997 | Chihiro et al. |
| 5,846,907 A | 12/1998 | von Deyn et al. |
| 5,877,187 A | 3/1999 | Orjales et al. |
| 5,977,108 A | 11/1999 | Kikuchi et al. |

FOREIGN PATENT DOCUMENTS

| | | |
|---|---|---|
| EP | 0 838 453 | 4/1998 |
| JP | 47-784 | 1/1972 |
| JP | 49-32853 | 9/1974 |
| JP | 51-63844 | 6/1976 |
| JP | 62-178590 | 8/1987 |
| JP | 1-156736 | 6/1989 |
| JP | 2-240058 | 9/1990 |
| JP | 4-128274 | 4/1992 |
| JP | 4-154773 | 5/1992 |
| JP | 6-65222 | 3/1994 |
| JP | 7-2851 | 1/1995 |
| JP | 9-71566 | 3/1997 |
| JP | 10-59951 | 3/1998 |
| JP | 10-101562 | 4/1998 |
| JP | 10-152437 | 6/1998 |
| SU | 1078859 A1 | 10/1997 |
| WO | WO 96/26206 | 8/1996 |
| WO | WO 98/08830 | 3/1998 |
| WO | WO 98/52967 | 11/1998 |

OTHER PUBLICATIONS

V. Tkachev et al. "Polymorphism of Some Diphilic Molecule Langmuir Monolayers. Experiment and Computer Modeling", Mol. Mats., 1992, vol. 1, pp. 169–174.

M. Chihiro et al. "Novel Thiazole Derivatives as Inhibitors of Superoxide Production by Human Neutrophils: Synthesis and Structure–Activity Relationships", J. Med. Chem. 1995, 38(2), 353–358.

Kevan Brown et al. "Nonsteroidal Antiinflammatory Agents. 1. 2,4–Diphenylthiazole–5–acetic Acid and Related Compounds", J. Med. Chem., 1974, vol. 17(11), pp. 1177–1181.

B.M.Krasovitskii et al. "Synthesis and Spectral and Luminescent Properties of 4–(5–aryloxazoyl–2)benzoic Acids and Their Derivatives", (Translated from Khimiya Geterotsiklicheskikh Soedinenii, 1986, No. 9, pp. 1261–1264).

F. Akutsu, et al. "Synthesis and Properties of Novel Aromatic Polyamides Containing 2–Methyl–4,5–Oxazolediyl Structure", POLYMER (1998) vol. 39, Nos. 8–9, pp. 1637–1641.

K. Liu, et al. "Photochemical Synthesis of 2(2–Aryl–5–Oxazolyl) Benzoates", OPPI BRIEFS (1983) vol. 15, No. 4, pp. 265–268.

A. Drusiani, "Phenylene–oxazoles", 59(8–9): 834–40(1969)—Chemical Abstract Service.

M.V. Kudrevatckh, et al. "Synthesis of 4–(5–phenyloxazol–2–yl)benzoic acid" (1996)—Chemical Abstracts Service.

*Primary Examiner*—Cecilia Tsang
*Assistant Examiner*—Ebenezer Sackey
(74) *Attorney, Agent, or Firm*—Mark Cha; Elaine Ramesh

(57) ABSTRACT

1,3-Azole derivatives, pharmaceutical compositions thereof and methods for regulating the function of retinoid-related receptors with 1,3-azole derivatives are disclosed. Such regulation may be useful for preventing or treating diabetes, preventing or treating hyperlipidemia, preventing or treating impaired glucose tolerance (IGT) or for preventing transition from impaired glucose tolerance to diabetes.

25 Claims, No Drawings

RETINOID-RELATED RECEPTOR FUNCTION REGULATING AGENT

This applicatin is the National Stage of International Application No. PCT/JP99/03520 filed on Jun. 30, 1999.

TECHNICAL FIELD

The present invention relates to a retinoid-related receptor function regulating agent comprising a 1,3-azole derivative or its salt, which is useful for treating or preventing diabetes, hyperlipidemia, impaired glucose tolerance, etc.

BACKGROUND ART

So far, 1,3-azole derivatives have been report in various references. For example, a compound having an anti-inflammatory effect (e.g., JP-A-4-154773, U.S. Pat. No. 5,342,851), a compound having a platelet aggregation-inhibiting effect (e.g., U.S. Pat. No. 5,342,851), a compound having an active oxygen-inhibiting effect (e.g., WO 9209586, Journal of Medicinal Chemistry, Vol.38, p. 353 1(1995), a compound having a thrombolytic effect (e.g., JP-B-49-32853) and a compound having a phospholipase IV-inhibiting effect (e.g., WO9808830) have been reported. Also, they have been reported as a liquid crystal composition (EP-A 439170) and a raw material compound for producing a vasopressin receptor ligand (WO9534540). Further, 1,3-azole carboxylic acid derivatives are described in Chemical Abstracts, vol.107, 23273h (1987), Chemical Abstracts, vol.113, 6239h (1990) and Chemical Abstracts, vol.120, 190974n (1994).

Some 1,3-azole derivatives are marketed as reagents by BIONET (Cornwall, England).

However, there has been no report that these compounds have a retinoid-related receptor function regulating effect, and exhibit excellent effects in treating or preventing diabetes, hyperlipidemia, impaired glucose tolerance, etc.

On the other hand, retinoid-related receptor function regulating agents are reported in JP-A-9-71566 (WO 9702244, EP838453), etc. However, there has been no report that these compounds exhibit excellent effects in treating or preventing hyperlipidemia, impaired glucose tolerance, etc.

Peroxisome proliferator-activated receptor gamma (PPARγ), a member of the intranuclear hormone receptor superfamily, which is typically exemplified by steroid hormone receptors and thyroid hormone receptors, plays an important role as a master regulator in the differentiation of adipose cells with its expression induced in the very early stage of adipose cell differentiation. PPARγ forms a dimer with the retinoid X receptor (RXR) by binding to a ligand, and binds to a responsive site of the target gene in the nucleus to directly control (activate) transcription efficiency. In recent years, it has been revealed that 15-deoxy-$\Delta^{12,14}$ prostaglandin $J_2$, a metabolite of prostaglandin $D_2$, serves as an endogenous ligand for PPARγ. Further it has been revealed that a class of insulin sensitivity enhancers, typically exemplified by thiazolidinedione derivatives, possess ligand activity for PPARγ, and that its potency is proportional to its hypoglycemic action or adipose cell differentiation-promoting action [Cell, vol. 83, p. 803 (1995): the Journal of Biological Chemistry, vol. 270, p. 12953 (1995); Journal of Medicinal Chemistry, vol. 39, p. 655 (1996)].

Many agents have been employed as agents for treating diabetes, hyperlipidemia, arteriosclerosis, etc. However, they are not satisfactory in terms of their therapeutic effects or reduced side effects, and the development of agents improved in these terms is strongly desired.

DISCLOSURE OF INVENTION

The inventors have discovered that a certain 1,3-azole derivative or its salt has an unexpectedly excellent PPAR ligand activity, and that it is useful as an agent for preventing or treating diabetes, hyperlipidemia, arteriosclerosis, etc. Based on these findings, the inventors made further investigations to complete the present invention.

Thus, the present invention relates to:

(1) a retinoid-related receptor function regulating agent comprising a 1,3-azole derivative represented by formula (I):

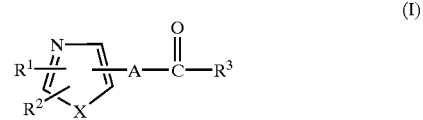

wherein $R^1$ is an aromatic hydrocarbon group or an aromatic heterocyclic group, each of which may be substituted; $R^2$ is hydrogen or an optionally substituted hydrocarbon group; X is O, S or a group represented by the formula: —$NR^4$— wherein $R^4$ is hydrogen or an optionally substituted alkyl group; A is an aromatic hydrocarbon group or an aromatic heterocyclic group, each of which may be substituted; $R^3$ is a group represented by the formula: —$OR^5$ wherein $R^5$ is hydrogen or an optionally substituted hydrocarbon group, or —$NR^6R^7$ wherein $R^6$ and $R^7$ are same or different and each is hydrogen or an optionally substituted hydrocarbon group, or $R^6$ and $R^7$ may be taken together with an adjacent nitrogen atom to form a ring, provided that compounds represented by the formulae:

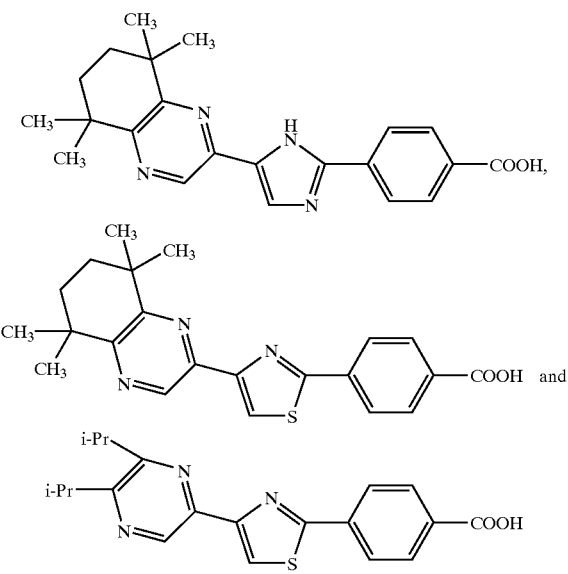

are excluded, or its salt.

(2) a function regulating agent according to the above (1) wherein $R^1$ is an aromatic hydrocarbon group or an aromatic heterocyclic group which does not contain a nitrogen atom, each of which may be substituted.

(3) a function regulating agent according to the above (1) which is an agent for preventing or treating diabetes.

(4) a function regulating agent according to the above (1) which is a lipid metabolism-improving agent.

(5) a function regulating agent according to the above (1) which is an agent for preventing or treating hyperlipidemia.

(6) a function regulating agent according to the above (1) which is an agent for preventing or treating obesity.

(7) a function regulating agent according to the above. (1) which is an anti-obesity agent.

(8) a function regulating agent according to the above (1) which is an insulin sensitivity enhancer.

(9) a function regulating agent according to the above (1) which is an insulin resistance improving agent.

(10) a function regulating agent according to the above (1) which is an agent for preventing or treating impaired glucose tolerance.

(11) an oxazole derivative represented by formula (I-1):

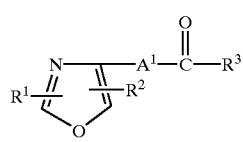

(I-1)

wherein $R^1$ is an aromatic hydrocarbon group or an aromatic heterocyclic group, each of which may be substituted; $R^2$ is hydrogen or an optionally substituted hydrocarbon group; $A^1$ is an aromatic hydrocarbon group or thienyl group, each of which may be substituted; $R^3$ is a group represented by the formula: —$OR^5$ wherein $R^5$ is hydrogen or an optionally substituted hydrocarbon group, or —$NR^6R^7$ wherein $R^6$ and $R^7$ are same or different and each is hydrogen or an optionally substituted hydrocarbon group, or $R^6$ and $R^7$ may be taken together with an adjacent nitrogen atom to form a ring, provided that compounds represented by the formula:

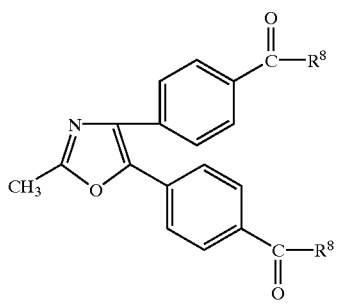

wherein both $R^8$s are $NH_2$, OH, phenoxy, $OCH_3$,

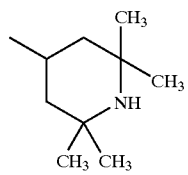 or 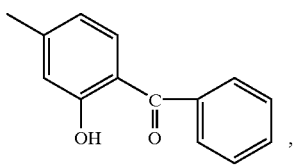, are excluded, or its salt.

(12) an oxazole derivative or its salt according to the above (11) wherein the formula is

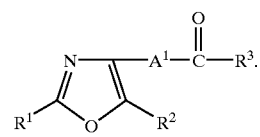

(13) an oxazole derivative represented by formula (I-2):

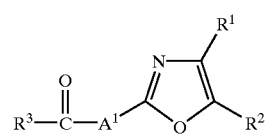

(I-2)

wherein $R^1$ is an aromatic hydrocarbon group or an aromatic heterocyclic group, each of which may be substituted; $R^2$ is hydrogen or an optionally substituted hydrocarbon group; $A^1$ is an aromatic hydrocarbon group or thienyl group, each of which may be substituted; $R^3$ is a group represented by the formula: —$OR^5$ wherein $R^5$ is hydrogen or an optionally substituted hydrocarbon group, or —$NR^6R^7$ wherein $R^6$ and $R^7$ are same or different and each is hydrogen or an optionally substituted hydrocarbon group, or $R^6$ and $R^7$ may be taken together with an adjacent nitrogen atom to form a ring, provided that compounds represented by the formulae:

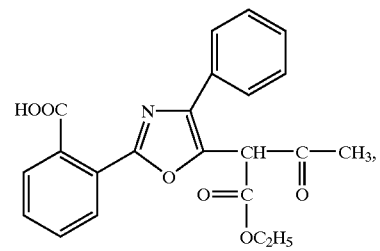

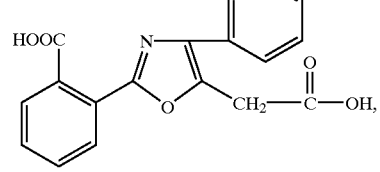

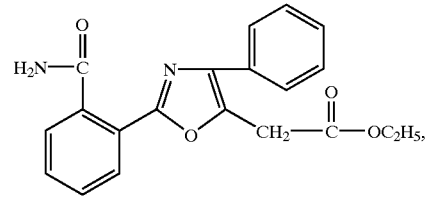

and

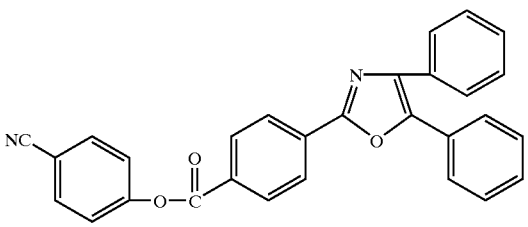

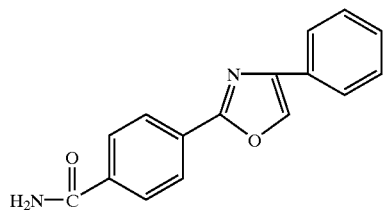

are excluded, or its salt.

(14) an oxazole derivative or its salt according to the above (13) wherein $R^2$ is hydrogen or an optionally substituted non-aromatic hydrocarbon group except for a non-aromatic hydrocarbon group which is substituted by an optionally esterified carboxyl group, and $R^3$ is a group represented by the formula: —$OR^5$.

(15) an oxazole derivative represented by formula (I-3):

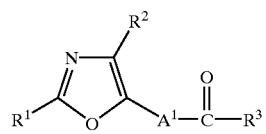

(I-3)

wherein $R^1$ is an aromatic hydrocarbon group or an aromatic heterocyclic group, each of which may be substituted; $R^2$ is hydrogen or an optionally substituted hydrocarbon group; $A^1$ is an aromatic hydrocarbon group or thienyl group, each of which may be substituted; $R^3$ is a group represented by the formula: —$OR^5$ wherein $R^5$ is hydrogen or an optionally substituted hydrocarbon group, or —$NR^6R^7$ wherein $R^6$ and $R^7$ are same or different and each is hydrogen or an optionally substituted hydrocarbon group, or $R^6$ and $R^7$ may be taken together with an adjacent nitrogen atom to form a ring, provided that compounds represented by the formulae:

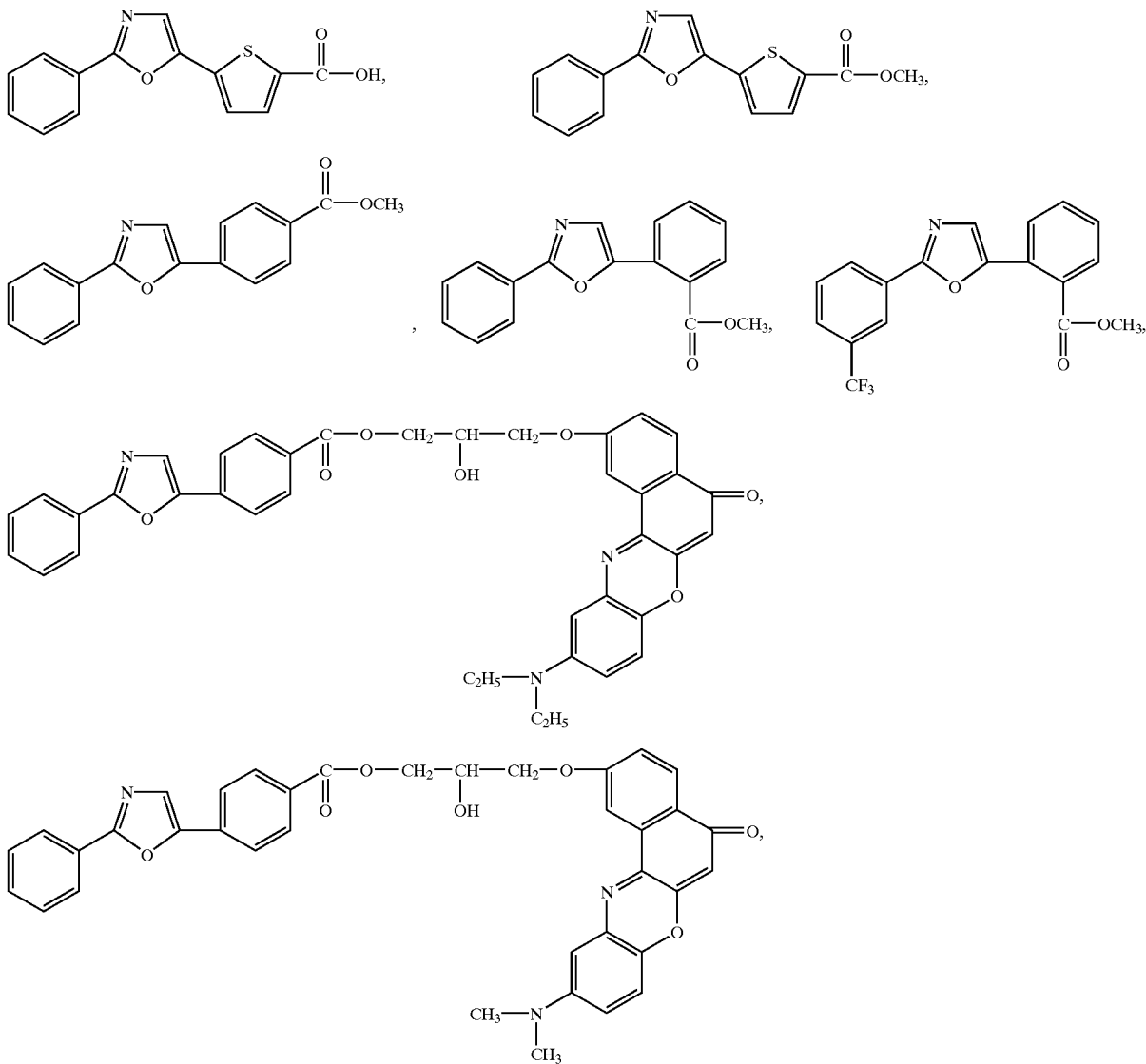

-continued
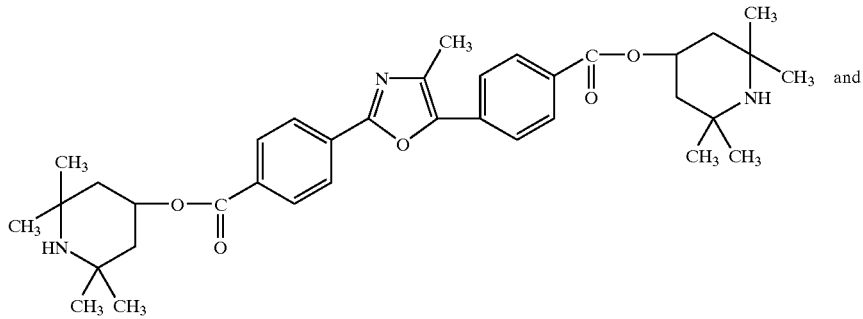
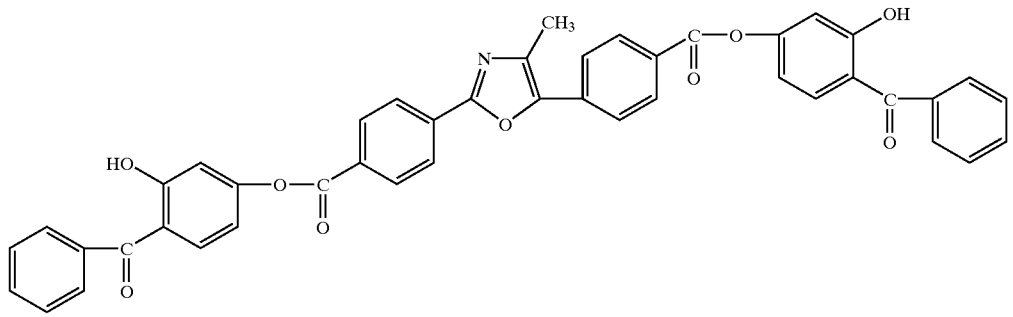
are excluded, or its salt.
(16) an oxazole derivative according to the above (15) wherein $A^1$ is a phenyl group having a —$COR^3$ group in a meta- or para-position, provided that compounds represented by the formulae:
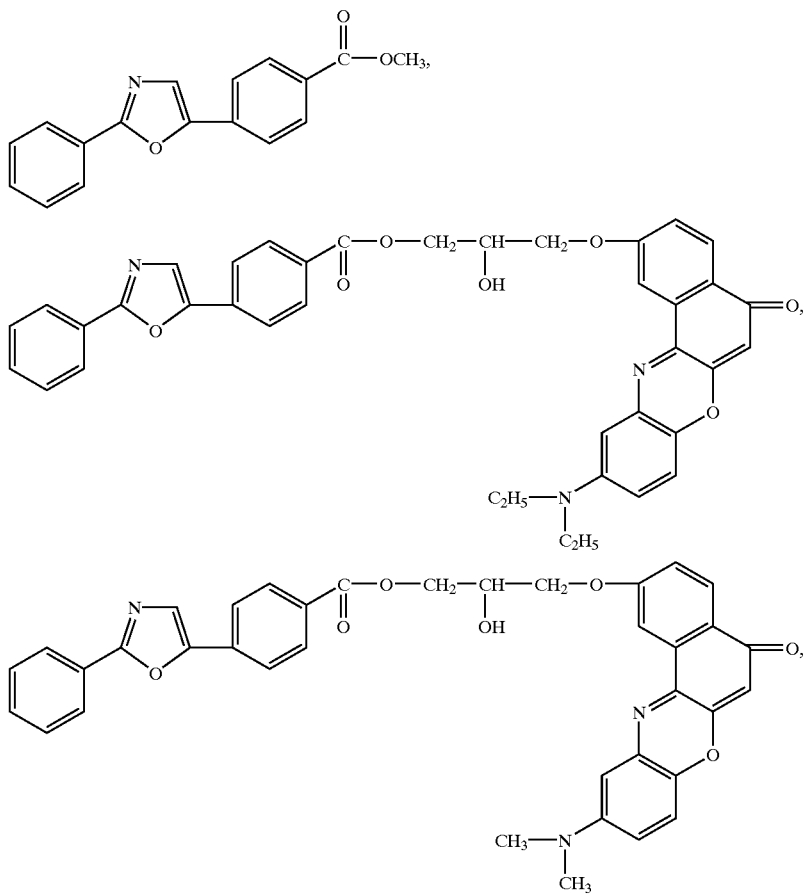

-continued

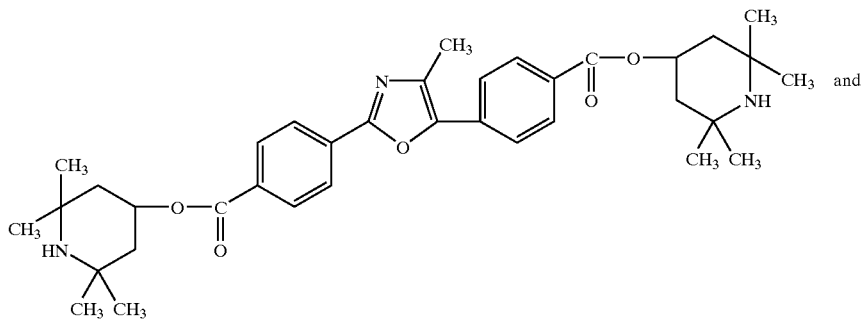

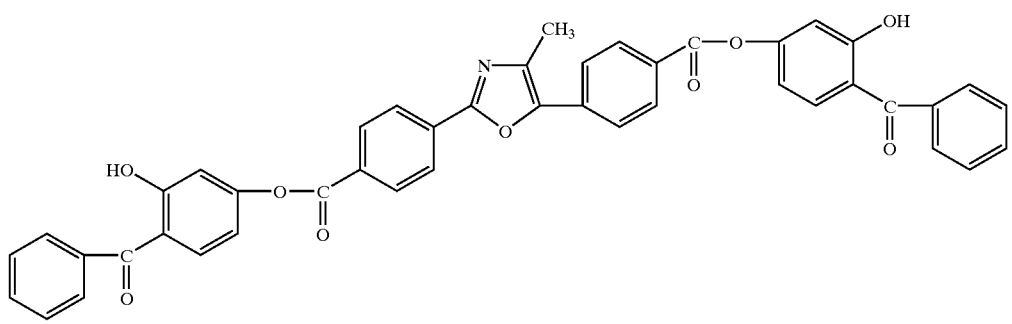

are excluded, or its salt.

(17) an oxazole derivative or its salt according to the above (16) wherein $R^3$ is OH.

(18) an imidazole derivative represented by formula (I-4):

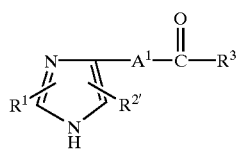
(I-4)

wherein $R^1$ is an aromatic hydrocarbon group or aromatic heterocyclic group, each of which may be substituted; $R^{2'}$ is hydrogen or an optionally substituted non-aromatic hydrocarbon group; $A^1$ is an aromatic hydrocarbon group or thienyl group, each of which may be substituted; $R^3$ is a group represented by the formula: $-OR^5$ wherein $R^5$ is hydrogen or an optionally substituted hydrocarbon group, or $-NR^6R^7$ wherein $R^6$ and $R^7$ are same or different and each is hydrogen or an optionally substituted hydrocarbon group, or $R^6$ and $R^7$ may be taken together with an adjacent nitrogen atom to form a ring, provided that a compound represented by the formula:

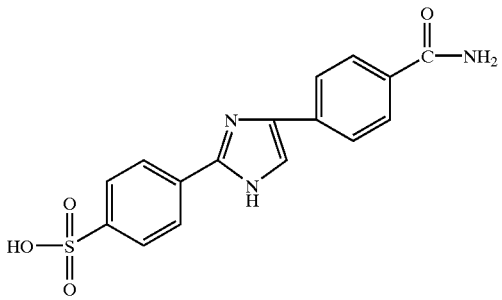

is excluded, or its salt.

(19) an imidazole derivative or its salt according to the above (18) wherein $R^1$ is an optionally substituted aromatic hydrocarbon group except for an aromatic hydrocarbon group substituted by sulfo group.

(20) an imidazole derivative represented by formula (I-5):

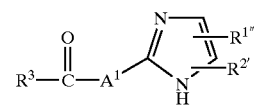
(I-5)

wherein $R^{1''}$ is an optionally substituted aromatic hydrocarbon group; $R^{2'}$ is hydrogen or an optionally substituted non-aromatic hydrocarbon group; $A^1$ is an aromatic hydrocarbon group or thienyl group, each of which may be substituted; $R^3$ is a group represented by the formula: $-OR^5$ wherein $R^5$ is hydrogen or an optionally substituted hydrocarbon group, or $-NR^6R^7$ wherein $R^6$ and $R^7$ are same or different and each is hydrogen or an optionally substituted hydrocarbon group, or $R^6$ and $R^7$ may be taken together with an adjacent nitrogen atom to form a ring, provided that compounds represented by the formulae:

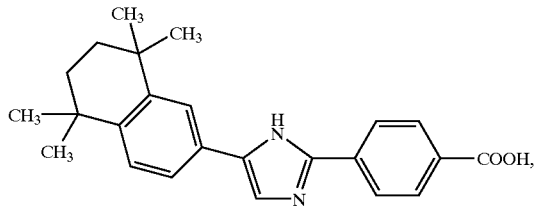

are excluded, or it is salt.

(21) an imidazole derivative according to the above (20) wherein $R^{1''}$ is an optionally substituted aromatic hydrocarbon, and said aromatic hydrocarbon group does not form a condensed ring, provided that a compound represented by the formula:

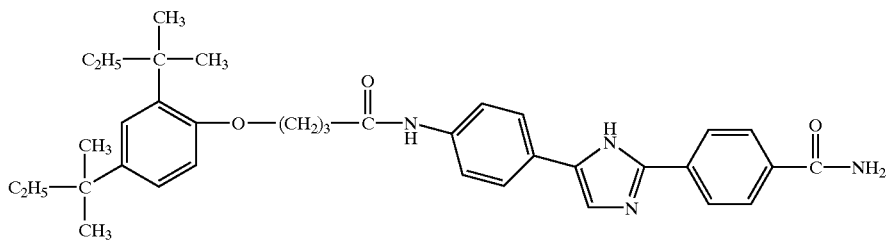

is excluded, or its salt.

(22) an imidazole derivative or its salt according to the above (21) wherein $R^3$ is a group represented by the formula —$OR^5$.

(23) a thiazole derivative represented by formula (I-6):

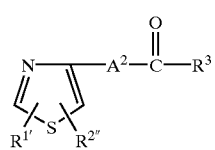

(I-6)

wherein $R^{1'}$ is an optionally substituted aromatic hydrocarbon group except for an aromatic hydrocarbon group substituted by a group having an intervening hetero atom; $R^{2''}$ is hydrogen or an alkyl group; $A^2$ is an optionally substituted aromatic hydrocarbon group except for an aromatic hydrocarbon substituted by a group having an intervening hetero atom; $R^3$ is a group represented by the formula: —$OR^5$

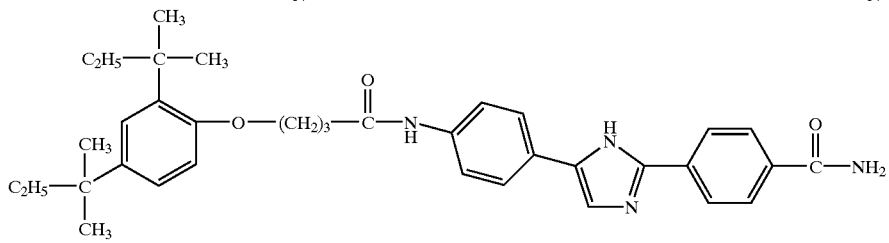

wherein $R^5$ is hydrogen or an optionally substituted hydrocarbon group, or —$NR^6R^7$ wherein $R^6$ and $R^7$ are same or different and each is hydrogen or an optionally substituted hydrocarbon group, or $R^6$ and $R^7$ may be taken together with an adjacent nitrogen atom to form a ring, provided that compounds represented by the formulae:

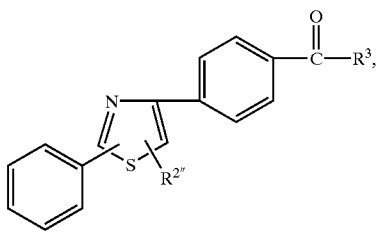

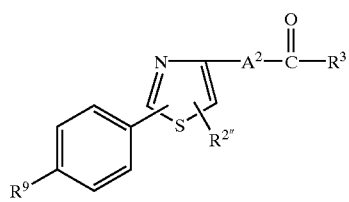

wherein $R^9$ is methoxy group, methyl group, chlorine, t-butyl group or trifluoromethyl group and,

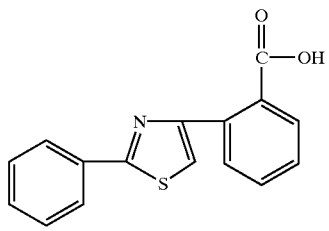

and its HBr salt are excluded, or its salt.

(24) a thiazole derivative or its salt according to the above (23) wherein $R^{1'}$ is an aromatic hydrocarbon group having at least two substituents.

(25) a thiazole derivative or its salt according to the above (23) wherein $R^{1'}$ is phenyl group having a substituent in an ortho- or meta-position.

(26) a thiazole derivative represented by formula (I-7):

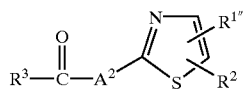

(I-7)

wherein $R^{1''}$ is an optionally substituted aromatic hydrocarbon group; $R^2$ is hydrogen or an optionally substituted hydrocarbon group; $A^2$ is an optionally substituted aromatic hydrocarbon group except for an aromatic hydrocarbon group substituted by a group having an intervening hetero atom; $R^3$ is a group represented by the formula: $-OR^5$ wherein $R^5$ is hydrogen or an optionally substituted hydrocarbon group, or $-NR^6R^7$ wherein $R^6$ and $R^7$ are same or different and each is hydrogen or an optionally substituted hydrocarbon group, or $R^6$ and $R^7$ may be taken together with an adjacent nitrogen atom to form a ring, provided that compounds represented by the formulae:

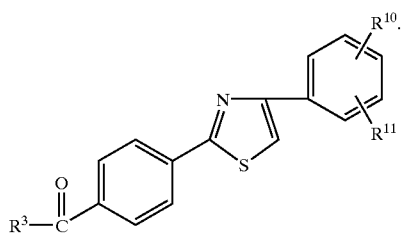

wherein the combination of the definitions is any of the following: both of $R^{10}$ and $R^{11}$ are hydrogen and $R^3$ is hydroxyl group or methoxy group; $R^{10}$ is chlorine substituting at 2- or 4-position, $R^{11}$ is hydrogen or $R^3$ is hydroxyl group or methoxy group; $R^{10}$ is chlorine substituting at 2- or 3-position, $R^{11}$ is chlorine substituting at 4-position, and $R^3$ is hydroxyl group or methoxy group; $R^{10}$ is fluorine substituting at 4-position, $R^{11}$ is hydrogen and $R^3$ is hydroxyl group or methoxy group; $R^{10}$ is methoxy group substituting at 4-position, $R^{11}$ is hydrogen and $R^3$ is hydroxyl group or methoxy group; $R^{10}$ is $CF_3$ group substituting at 3-position, $R^{11}$ is hydrogen and $R^3$ is hydroxyl group or methoxy group,

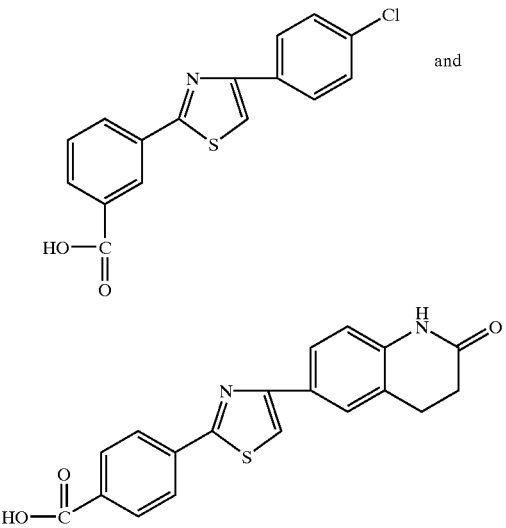

are excluded, or its salt.

(27) a thiazole derivative or its salt according to the above (26) wherein $R^{1''}$ is an aromatic hydrocarbon group having at least two substituents.

(28) a thiazole derivative or its salt according to the above (27) wherein $A^2$ is phenyl group having a substituent —COR3 in an ortho-position.

(29) a thiazole derivative or its salt according to the above (26) wherein $R^2$ is an optionally substituted hydrocarbon group.

(30) a thiazole derivative represented by formula (I-8):

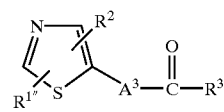

(I-8)

wherein $R^{1''}$ is an optionally substituted aromatic hydrocarbon group; $R^2$ is hydrogen or an optionally substituted hydrocarbon group; $A^3$ is an optionally substituted aromatic hydrocarbon group; $R^3$ is a group represented by the formula: $-OR^5$ wherein $R^5$ is hydrogen or an optionally substituted hydrocarbon group, or $-NR^6R^7$ wherein $R^6$ and $R^7$ are same or different and each is hydrogen or an optionally substituted hydrocarbon group, or $R^6$ and $R^7$ may be taken together with an adjacent nitrogen atom to form a ring, provided that a compound represented by the formula:

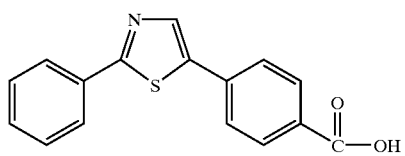

is excluded, or its salt.

(31) a thiazole derivative or its salt according to the above (30) wherein $R^{1''}$ is a substituted aromatic hydrocarbon group.

(32) at least one compound selected from the group consisting of:
  i) 4-[4-(4-chlorophenyl)-2-oxazolyl]benzoic acid,
  ii) 4-[4-4-trifuoromethylphenyl)-2-oxazolyl]benzoic acid,
  iii) 4-[4-(4-trifuoromethylphenyl)-2-thiazolyl]benzoic acid, iv) 4-[4-(4-trifluoromethoxyphenyl)-2-thiazolyl]benzoic acid,
v) 3-[4-(4-isopropylphenyl)-2-thiazolyl]benzoic acid,
vi) 3-[4-(4-ethoxyphenyl)-2-thiazolyl]benzoic acid,
vii) 4-[2-(4-trifluoromethylphenyl)-5-oxazolyl]benzoic acid,
viii) 4-[2-(4-trifluoromethylphenyl)-5-thiazolyl]benzoic acid,
ix) 3-[4-(2,5-dimethyl-3-furyl)-2-thiazolyl]benzoic acid and,
x) 3-[4-(2,5-dimethyl-3-thienyl)-2-thiazolyl]benzoic acid, or its salt.

(33) a method for regulating a retinoid-related receptor function comprising administering a 1,3-azole derivative represented by formula (I):

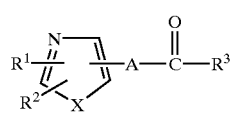
(I)

wherein $R^1$ is an aromatic hydrocarbon group or an aromatic heterocyclic group, each of which may be substituted; $R^2$ is hydrogen or an optionally substituted hydrocarbon group; X is O, S or a group represented by the formula: —$NR^4$— wherein $R^4$ is hydrogen or an optionally substituted alkyl group; A is an optionally substituted aromatic hydrocarbon group or an aromatic heterocyclic group, each of which may be substituted; $R^3$ is a group represented by the formula: —$OR^5$— wherein $R^5$ is hydrogen or an optionally substituted hydrocarbon group, or —$NR^6R^7$ wherein $R^6$ and $R^7$ are same or different and each is hydrogen or an optionally substituted hydrocarbon group, or $R^6$ and $R^7$ may be taken together with an adjacent nitrogen atom to form, a ring, provided that compounds represented by the formulae:

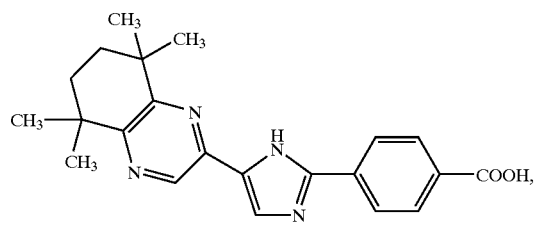
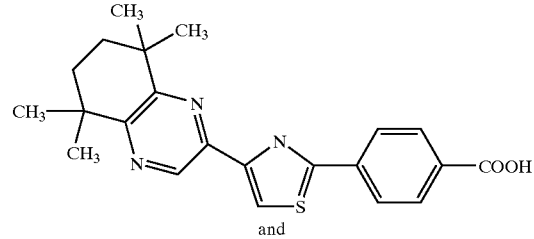
and
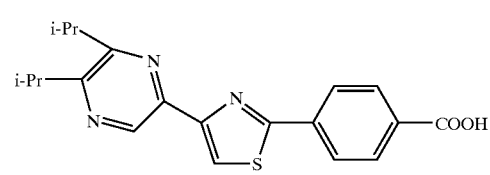

are excluded, or its salt.

(34) use of a 1,3-azole derivative represented by formula (I):

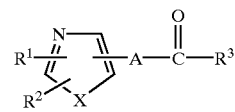
(I)

wherein $R^1$ is an aromatic hydrocarbon group or an aromatic heterocyclic group, each of which may be substituted; $R^2$ is hydrogen or an optionally substituted hydrocarbon group; X is O, S or a group represented by the formula: —$NR^4$— wherein $R^4$ is hydrogen or an optionally substituted alkyl group; A is an aromatic hydrocarbon group or an aromatic heterocyclic group, each of which may be substituted; $R^3$ is a group represented by the formula: —$OR^5$ wherein $R^5$ is hydrogen or an optionally substituted hydrocarbon group, or —$NR^6R^7$ wherein $R^6$ and $R^7$ are same or different and each is hydrogen or an optionally substituted hydrocarbon group, or $R^6$ and $R^7$ may be taken together with an adjacent nitrogen atom to form a ring, provided that compounds represented by the formulae:

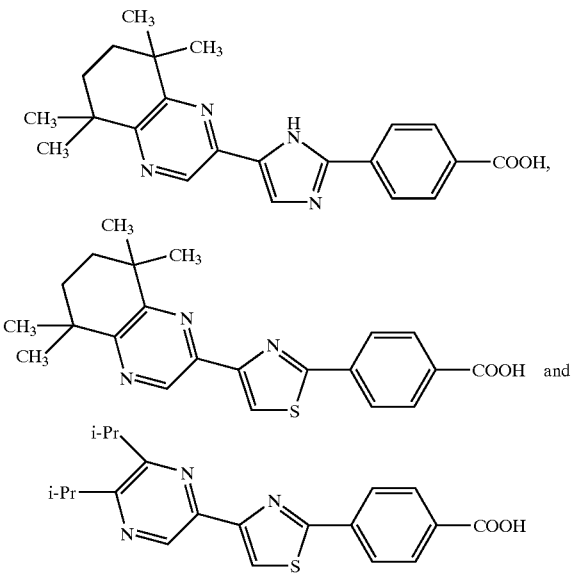

are excluded, or its salt for producing a pharmaceutical for regulating a retinoid-related receptor function.

BEST MODE FOR CARRYING OUT THE INVENTION

In the formula (I), $R^1$ and A are an optionally substituted aromatic hydrocarbon group or an aromatic heterocyclic group, each of which may be substituted.

Examples of the aromatic hydrocarbon group in the optionally substituted aromatic hydrocarbon group for $R^1$ and A include an aryl group having 6 to 14 carbon atoms, such as phenyl, naphthyl, anthryl, phenanthryl, acenaphthylenyl, azulenyl, biphenylyl and the like, with phenyl, 1-naphthyl and 2-naphthyl being preferred.

Examples of the aromatic heterocyclic group in the optionally substituted aromatic heterocyclic group for $R^1$ and A include a 5 to 7-membered aromatic monocyclic heterocyclic group having as a ring constituting atoms, in addition to carbon atoms, 1 to 4 hetero atoms selected from oxygen, sulfur and nitrogen atoms or an aromatic condensed heterocyclic group.

Concrete examples of the aromatic heterocyclic group include an aromatic monocyclic heterocyclic group such as furyl, thienyl, pyrrolyl, oxazolyl, isoxazolyl, thiazolyl, isothiazolyl, imidazolyl, pyrazolyl, 1,2,3-oxadiazolyl, 1,2,4-oxadiazolyl, 1,3,4-oxadiazolyl, furazanyl, 1,2,3-thiadiazolyl, 1,2,4-thiadiazolyl, 1,3,4-thiadiazolyl, 1,2,3-triazolyl, 1,2,4-triazolyl, tetrazolyl, pyridyl, pyrimidinyl, pyridazinyl, pyrazinyl and triazinyl; a bicyclic or tricyclic aromatic condensed heterocyclic group such as benzofuranyl, isobenzofuranyl, benzo[b]thienyl, indolyl, isoindolyl, 1H-indazolyl, benzimidazolyl, benzoxazolyl, benzothiazolyl, 1H-benzotriazolyl, quinolyl, isoquinolyl, cinnolyl, quinazolyl, quinoxalinyl, phthalazinyl, naphthylidinyl, purinyl, pteridinyl, carbazolyl, α-carbonylyl, β-carbonylyl, γ-carbonylyl, acridinyl, phenoxazinyl, phenothiazinyl, phenazinyl, phenoxathiynyl, thianthrenyl, indolydinyl, pyrrolo[1,2-b]pyridazinyl, pyrazolo[1,5-a]pyridyl, imidazo[1,2-a]pyridyl, imidazo[1,5-a]pyridyl, imidazo[1,2-b]pyridazinyl, imidazo[1,2-a]pyrimidinyl, 1,2,4-triazolo]4,3-a]pyridyl and 1,2,4,-triazolo]4,3-b]pyridazinyl. Among these, regarding $R^1$, an aromatice heterocyclic group which does not contain a nitrogen atome is preferable, and a thienyl group and a furyl group are more preferable. Regarding A, an aromatic monocyclic heterocyclic group is preferable, and a pyridyl group and a thienyl group are more perferable.

Examples of the substituent in the above aromatic hydrocarbon group and aromatic heterocyclic group include optionally halogenated alkyl group having 1 to 6 carbon atoms, alkenyl group having 2 to 6 carbon atoms, alkynyl g up having 2 to 6 carbon atoms, cycloalkyl group having 3 to 7 carbon atoms, cycloalkenyl group having 3 to 7 carbon atoms, cycloalkynyl group having 3 to 7 carbon atoms, aryl group having 6 to 14 carbon atoms (e.g., phenyl, naphthyl, etc.), 5- to 6-membered heterocyclic group (e.g., thienyl, furyl, pyridyl, oxazolyl, thiazolyl, etc.), 5- to 6-membered non-aromatic heterocyclic group (e.g., tetrahydrofuryl, morpholinyl, thiomorpholinyl, piperidinyl, pyrrolidinyl, piperazinyl, etc.), aralkyl group having 7 to 19 carbon atoms (benzyl, benrzhydryl, trityl, etc.), amino group optionally mono- or di-substituted by an alkyl having 1 to 4 carbon atoms or an acyl having 2 to 8 carbon atoms (e.g., alkanoyl having 2 to 8 carbon atoms), amidino group, an acyl group having 2 to 8 carbon atoms (e.g., alkanoyl having 2 to 8 carbon atoms), carbamoyl group optionally mono- or di-substituted by an alkyl having 1 to 4 carbon atoms, sulfamoyl group optionally mono- or di-substituted by an alkyl having 1 to 4 carbon atoms, an optionally esterified carboxyl group (e.g., alkoxycarbonyl group having 2 to 8 carbon atoms), hydroxyl group, optionally halogenated alkoxy group having 1 to 6 carbon atoms, alkenyloxy group having 2 to 5 carbon atoms, cycloalkyloxy group having 3 to 7 carbon atoms, aralkyloxy group having 7 to 9 carbon atoms, aryloxy group having 6 to 14 carbon atoms (e.g., phenoxy, naphthyloxy, etc.), thiol group, alkylthio group having 1 to 6 carbon atoms, aralkylthio group having 7 to 19 carbon atoms (e.g., benzylthio, etc.), arylthio group having 6 to 14 carbon atoms (e.g., phenylthio, naphthylthio, etc.), sulfo group, cyano group, azido group, nitro group, nitroso group, halogen atom (e.g., fluorine, chlorine, bromine, iodine, etc.) and the like. Among these, regarding the substituent on $R^1$, a substituent which does not form a condensed ring is preferable, and an alkyl group having 1 to 6 carbon atoms, a halogen atom or a halogen atom-containing substituent is more preferable. Regarding t sub-stituent on A, a substituent which does not bind via a hetero atom is preferable.

$R^3$ is a group represented by the formula: —$OR^5$ wherein $R^5$ is hydrogen or an optionally substituted hydrocarbon group, or —$NR^6R^7$ wherein $R^6$ and $R^7$ are same or different and each is hydrogen or an optionally substituted hydrocarbon group, or $R^6$ and $R^7$ may be taken together with an adjacent nitrogen atom to form a ring.

$R^2$ is hydrogen or an optionally substituted hydrocarbon group in the same manner as $R^5$. Examples of the optionally substituted hydrocarbon group in $R^2$ and $R^5$ include a hydrocarbon group having 1 to 24 carbon atoms, such as an aliphatic hydrocarbon group having 1 to 14 carbon atoms, an alicyclic hydrocarbon group having 3 to 10 carbon atoms, an alicyclic hydrocarbon group having 3 to 10 carbon atoms—an aliphatic hydrocarbon having 1 to 14 carbon atoms, an aromatic aliphatic hydrocarbon group having 7 to 19 carbon atoms and an aromatic hydrocarbon group having 6 to 14 carbon atoms. Among these, regarding $R^2$, an aliphatic hydrocarbon group having 1 to 14 carbon atoms, an alicyclic hydrocarbon group having 3 to 10 carbon atoms and an aromatic hydrocarbon group having 6 to 14 carbon atoms are preferably used, especially an alkyl group having 1 to 8 carbon atoms is preferably used. Regarding $R^5$, an aliphatic hydrocarbon having 1 to 14 carbon atoms an dan aromatic aliphatic hydrocarbon group having 7 to 19 carbon atoms are preferably used, especially an alkyl group having 1 to 8 carbon atoms and an aralkyl-group having 7 to 19 carbon atoms are preferably used.

Examples of an aliphatic hydrocarbon group having 1 to 14 carbon atoms include an alkyl group having 1 to 8 carbon atoms such as methyl, ethyl, propyl, isopropyl, butyl, isobutyl, sec.-butyl, t.-butyl, pentyl, isopentyl, neopentyl, hexyl, isohexyl, heptyl and octyl, an alkenyl group having 2 to 8 carbon atoms such as ethenyl, 1-propenyl, 2-propenyl, 1-butenyl, 2-butenyl, 3-butenyl, 2-methyl-1-propenyl, 1-pentenyl, 2-pentenyl, 3-pentenyl, 4-pentenyl, 3-methyl-2-butenyl, 1-hexenyl, 3-hexenyl, 2,4-hexadienyl, 5-hexenyl, 1-heptenyl and 1-octenyl; an alkynyl group having 2 to 8 carbon atoms such as ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 3-hexynyl, 2,4-hexadiynyl, 5-hexynyl, 1-heptynyl and 1-octynyl.

Examples of an alicyclic hydrocarbon having 3 to 10 carbon atoms include a cycloalkyl group having 3 to 7 carbon atoms such as cyclopropyl, cyclobutyl, cyclopentyl, cyclohexyl and cycloheptyl; a cycloalkenyl group having 5 to 7 carbon atoms such as 1-cyclopentenyl, 2-cyclopentenyl, 3-cyclopentenyl, 1-cyclohexenyl, 2-cyclohexenyl, 3-cyclohexenyl, 1-cycloheptenyl, 2-cycloheptenyl, 3-cycloheptenyl and 2,4-cycloheptadienyl.

Examples of an alicyclic hydrocarbon group having 3 to 10 carbon atoms—aliphatic hydrocarbon having 1 to 14 carbon atoms include a cycloalkyl having 3 to 7 carbon atoms—alkyl group having 1 to 14 carbon atoms, a cycloalkenyl having 5 to 7 carbon atoms—alkyl group having 1 to 14 carbon atoms, etc. Concrete examples include cyclopropylmethyl, cyclopropylethyl, cyclobutylmethyl, cyclopentylethyl, cyclohexylmethyl, cyclohexylmethyl, cyclohexylpropyl, cycloheptylethyl, cycloheptylethyl, 2-cyclopentenylmethyl, 3-cyclopentenylmethyl, 2-cyclohexenylmethyl, 3-cyclohexenylmethyl, etc.

Concrete examples of an aromatic aliphatic hydrocarbon group having 7 to 19 carbon atoms include an aralkyl group having 7 to 19 carbon atoms such as benzyl, phenethyl, 1-phenylethyl, 1-phenylpropyl, 2-phenylpropyl, 3-phenylpropyl, α-naphthylmethyl, α-naphthylethyl, β-naphthylmethyl and β-naphthylethyl; an arylalkenyl group having 8 to 13 carbon atoms such as styryl and 2-(2-naphthylvinyl).

Examples of an aromatic hydrocarbon having 6 to 14 carbon atoms include phenyl, naphthyl, anthryl, phenanthryl, acenaphthylenyl, biphenylyl, etc.

The substituent in the above hydrocarbon groups is exemplified by that similar to the substituent on the aromatic hydrocarbon and the aromatic heterocyclic groups defined for $R^1$ and A. The substituent in $R^5$ is preferably a halogen atom and an alkoxy group having 1 to 6 carbon atoms.

$R^4$ is hydrogen or an optionally substituted alkyl group, with hydrogen being particularly preferred. Examples of the alkyl group in an optionally substituted alkyl group include a straight-chain or branched alkyl group having, 1 to 16 carbon atoms. Preferred examples include a straight-chain or branched alkyl group having 1 to 12 carbon atoms, such as methyl, ethyl, propyl, isopropyl, butyl, isobutyl, sec.-butyl, t.-butyl, pentyl, isopentyl, neopentyl, 1-ethylpropyl, hexyl, isohexyl, 1,1-dimethylbutyl, 2,2-dimethylbutyl, 3,3-dimethylbutyl, 2-ethylbutyl, heptyl, octyl, nonyl, decyl, undecyl and dodecyl.

Examples of a substituent on such alkyl group include an alkenyl group having 2 to 6 carbon atoms, a cycloalkyl group having 3 to 7 carbon atoms, an aryl group having 6 to 14 carbon atoms (e.g., phenyl, naphthyl, etc.), a 5- to 6-membered aromatic heterocyclic group (e.g., thienyl, furyl, pyridyl, oxazolyl, thiazolyl, etc.), a 5- to 6-membered non-aromatic heterocyclic group (e.g., tetrahydrofuryl, morpholinyl, thiomorpholinyl, piperidinyl, pyrrolidinyl, piperazinyl, etc.), an aralkyl group having 7 to 19 carbon atoms (benzyl, benzhydryl, trityl, etc.), amino group optionally mono- or di-substituted by an alkyl having 1 to 4 carbon atoms or an acyl having 2 to 8 carbon atoms (e.g., alkanoyl having 2 to 8 carbon atoms), amidino group, an acyl group having 2 to 8 carbon atoms (e.g., alkanoyl having 2 to 8 carbon atoms), carbamoyl group optionally mono- or di-substituted by an alkyl group having 1 to 4 carbon atoms, sulfamoyl group optionally mono- or di-substituted by an alkyl having 1 to 4 carbon atoms, an optionally esterified carboxyl group (e.g., alkoxycarbonyl group having 2 to 8 carbon atoms), hydroxyl group, an alkoxy group having 1 to 6 carbon atoms, an alkenyloxy group having 2 to 5 carbon atoms, a cycloalkyloxy group having 3 to 7 carbon atoms, an aralkyloxy group having 7 to 9 carbon atoms, an aryloxy group having 6 to 14 carbon atoms (e.g., phenoxy, naphthyloxy, etc.), thiol group, an alkylthio group having 1 to 6 carbon atoms, an aralkylthio group having 7 to 19 carbon atoms (e.g., benzylthio, etc.), an arylthio, group having 6 to 14 carbon atoms (e.g., phenylthio, naphthylthio, etc.), sulfo group, cyano group, azido group, nitro group, nitroso group, a halogen atom (e.g., fluorine, chlorine, bromine, iodine, etc.).

As described above, $R^6$ and $R^7$ are hydrogen or an optionally substituted hydrocarbon group, respectively. The optionally substituted hydrocarbon group defined for $R^6$ and $R^7$ is exemplified by that similar to the optionally substituted hydrocarbon-group defined for $R^2$ and $R^5$.

Examples of a N-containing heterocyclic group formed by $R^6$ and $R^7$ together with an adjacent nitrogen atom include a 5- to 7-membered ring. Concrete examples include 1-pyrrolidinyl, piperidino, morpholino, thiomorpholino, 1-piperazinyl, hexamethyleneimin-1-yl, oxazolidin-3-yl, thiazolidin-3-yl, imidazolidin-3-yl, 2-oxoimidazolidin-1-yl, 2,4-dioxoimidazolidin-3-yl, 2,4-dioxooxazolidin-3-yl, 2,4-dioxothiazolidin-3-yl.

A compound represented by formula (I) includes, for instance, compounds represented by the following formulae:

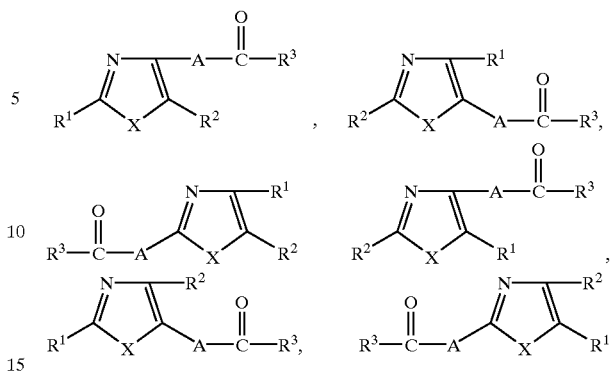

wherein each, symbol has the same meanings as defined above.

Among the compound represented by formula (I), preferred is a compound wherein $R^1$ is phenyl, thienyl, furyl or pyridyl (preferably phenyl or thienyl, more preferably phenyl), each of which may have 1 to 5 (preferably 1 to 3, more preferably 1 to 2) substituents selected from a halogen atom, an optionally halogenated alkyl group having 1 to 6 carbon atoms and an optionally halogenated alkoxy group having 1 to 6 carbon atoms, $R^2$ is hydrogen atom, X is O or S, A is phenyl or thienyl (preferably phenyl), $R^3$ is a group represented by the formula: $-OR^5$ wherein $R^5$ is hydrogen or an alkyl group having 1 to 6 carbon atoms (preferably hydrogen); and especially preferred is at least one compound selected from:

i) 4-[4-(4-chlorophenyl)-2-oxazolyl]benzoic acid, ii) 4-[4-(4-trifluoromethylphenyl)-2-oxazolyl]benzoic acid, iii) 4-[4-(4-trifluoromethylphenyl)-2-thiazolyl]benzoic acid, iv) 4-[4-(4-trifluoromethoxyphenyl)-2-thiazolyl]benzoic acid, v) 3-[4-(4-isopropylphenyl)-2-thiazolyl]benzoic acid, vi) 3-[4-(4-ethoxyphenyl)-2-thiazolyl]benzoic acid, vii) 4-[2-(4-trifluoromethylphenyl)-5-oxazolyl]benzoic acid, viii) 4-[2-(4-trifluoromethylphenyl)-5-thiazolyl]benzoic acid, ix) 3-[4-(2,5-dimethyl-3-furyl)-2-thiazolyl]benzoic acid, and x) 3-[4-(2,5-dichloromethyl-3-thienyl)-2-thiazolyl]benzoic acid, or its salt.

Among the compounds represented by formula (I), the followings are novel compounds:

an oxazole derivative represented by formula (I-1):

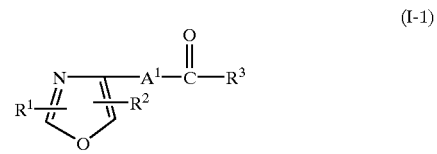

(I-1)

wherein $R^1$ is an aromatic hydrocarbon group or an aromatic heterocyclic group, each of which may be substituted; $R^2$ is hydrogen or an optionally substituted hydrocarbon group; $A^1$ is an aromatic hydrocarbon group or thienyl group, each of which may be substituted; R³ is a group represented by the formula: —OR⁵ wherein R⁵ is hydrogen or an optionally substituted hydrocarbon group, or —NR⁶R⁷ wherein R⁶ and R⁷ are same or different and each is hydrogen or an optionally substituted hydrocarbon group, or R⁶ and R⁷ may be taken together with an adjacent nitrogen atom to form a ring, provided that compounds represented by the formula:

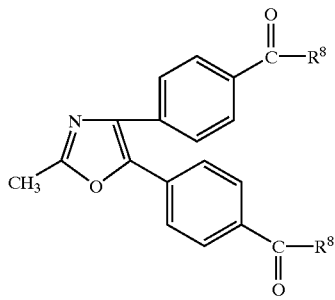

wherein both R⁸s are NH₂, OH, phenoxy, OCH₃,

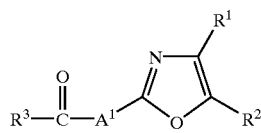

are excluded, or its salt;

an oxazole derivative represented by formula (I-2):

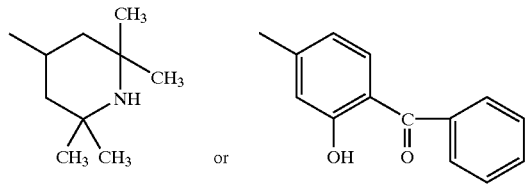
(I-2)

wherein R¹ is an aromatic hydrocarbon group or an aromatic heterocyclic group, each of which may be substituted; R² is hydrogen or an optionally substituted hydrocarbon group; A¹ is an aromatic hydrocarbon group or thienyl group, each of which may be substituted; R³ is a group represented by the formula: —OR⁵ wherein R⁵ is hydrogen or an optionally substituted hydrocarbon group, or —NR⁶R⁷ wherein R⁶ and R⁷ are same or different and each is hydrogen or an optionally, substituted hydrocarbon group, or R⁶ and R⁷ may be taken together with an adjacent nitrogen atom to form a ring, provided that compounds represented by the formulae:

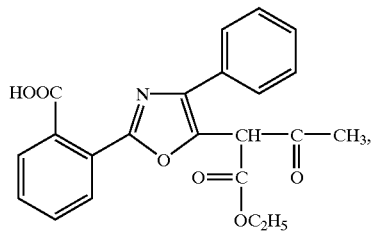

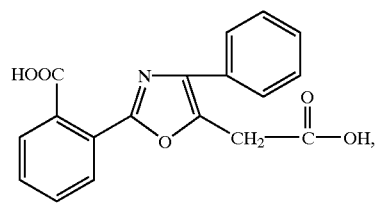

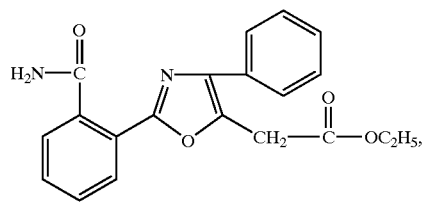

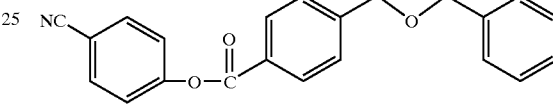

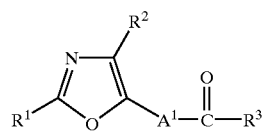

are excluded, or its salt;

an oxazole derivative represented by formula (I-3):

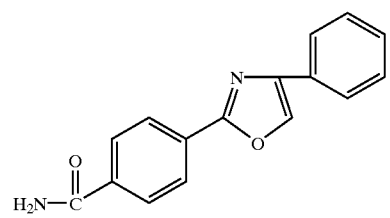
(I-3)

wherein R¹ is an aromatic hydrocarbon group or aromatic heterocyclic group, each of which may be substituted; R² is hydrogen or an optionally substituted hydrocarbon group; A¹ is an aromatic hydrocarbon group or thienyl group, each of which may be substituted; R³ is a group represented by the formula: —OR⁵ wherein R⁵ is hydrogen or an optionally substituted hydrocarbon group, or —NR⁶R⁷ wherein R⁶ and R⁷ are same or different and each is hydrogen or an optionally substituted hydrocarbon group, or R⁶ and R⁷ may be taken together with an adjacent nitrogen atom to form a ring, provided that compounds represented by the formulae:

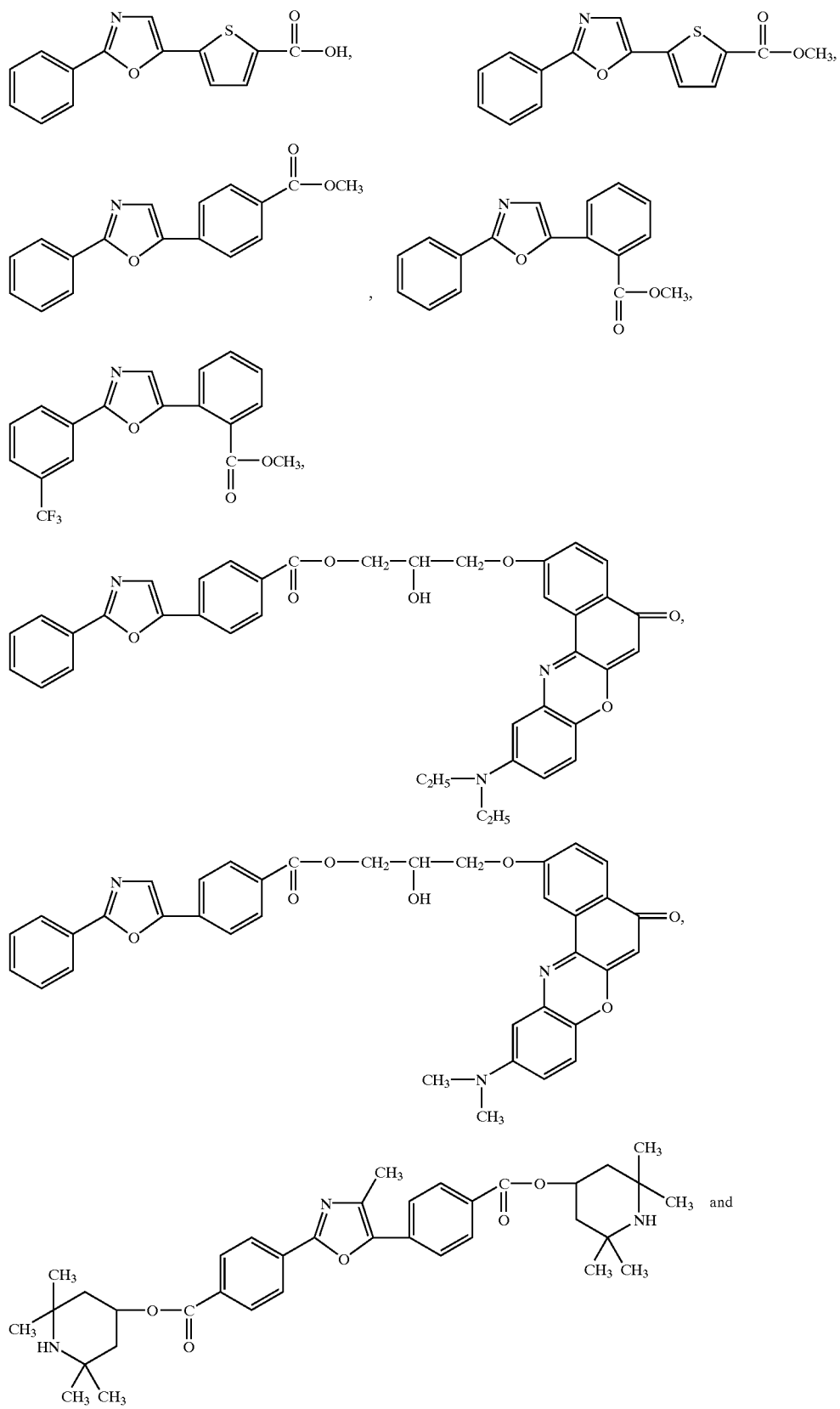

-continued

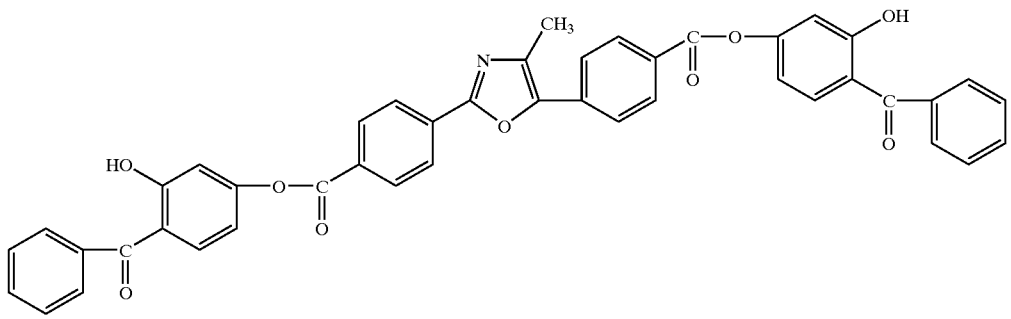

are excluded, or its salt;

an imidazole derivative represented by formula (I-4):

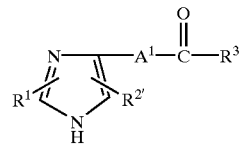
(I-4)

wherein $R^1$ is an aromatic hydrocarbon group or aromatic heterocyclic group, each of which may be substituted; $R^{2'}$ is hydrogen or an optionally substituted non-aromatic hydrocarbon group; $A^1$ is an aromatic hydrocarbon group or thienyl group, each of which may be substituted; $R^3$ is a group represented by the formula: —$OR^5$ wherein $R^5$ is hydrogen or an optionally substituted hydrocarbon group, or —$NR^6R^7$ wherein $R^6$ and $R^7$ are same or different and each is hydrogen or an optionally substituted hydrocarbon group, or $R^6$ and $R^7$ may be taken together with an adjacent nitrogen atom to form a ring, provided that a compound represented by the formula:

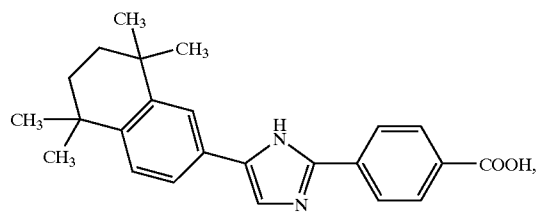

is excluded, or its salt;

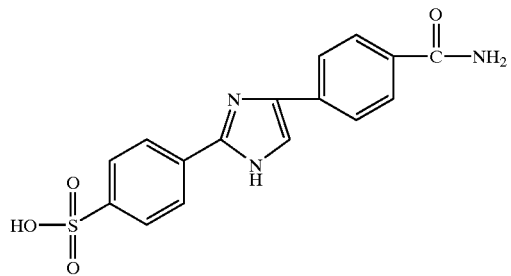

an imidazole derivative represented by formula (I-5):

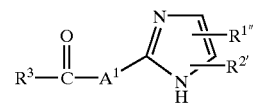
(I-5)

wherein $R^{1''}$ is an optionally substituted aromatic hydrocarbon group; $R^{2'}$ is hydrogen or an optionally substituted non-aromatic hydrocarbon group; $A^1$ is an aromatic hydrocarbon group or thienyl group, each of which may be substituted; $R^3$ is a group represented by the formula: —$OR^5$ wherein $R^5$ is hydrogen or an optionally substituted hydrocarbon group, or —$NR^6R^7$ wherein $R^6$ and $R^7$ are same or different and each is hydrogen or an optionally substituted hydrocarbon group, or $R^6$ and $R^7$ may be taken together with an adjacent nitrogen atom to form a ring, provided that compounds represented by the formulae:

-continued

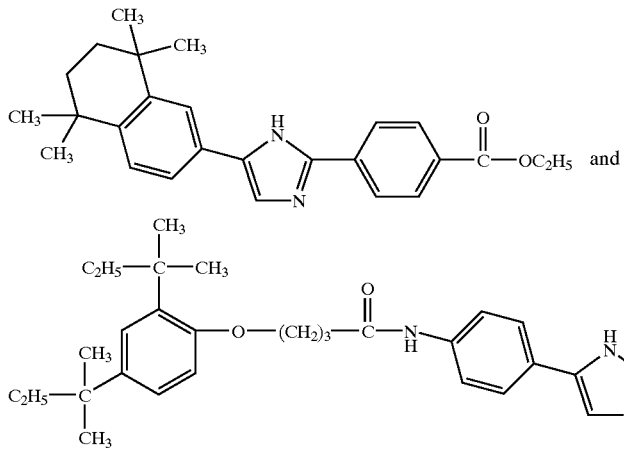

are excluded, or its salt;

a thiazole derivative represented by formula (I-6):

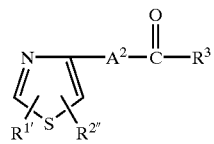
(I-6)

wherein $R^{1'}$ is an optionally substituted aromatic hydrocarbon group except for an aromatic hydrocarbon group substituted by a group having an intervening hetero atom; $R^{2''}$ is hydrogen or an alkyl group; $A^2$ is an optionally substituted aromatic hydrocarbon group except for an aromatic hydrocarbon group substituted by a group having an intervening hetero atom; $R^3$ is a group represented by the formula: $-OR^5$ wherein $R^5$ is hydrogen or an optionally substituted hydrocarbon, group, or $-NR^6R^7$ wherein $R^6$ and $R^7$ are same or different and each is hydrogen or an optionally substituted hydrocarbon group, or $R^6$ and $R^7$ may be taken together with an adjacent nitrogen atom to form a ring, provided that compounds represented by the formulae:

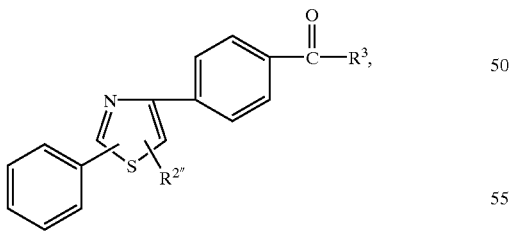

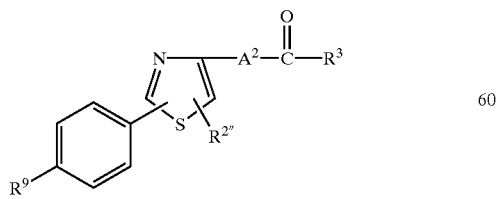

wherein $R^9$ is methoxy group, methyl group, chlorine, t-butyl group or trifluoromethyl group and,

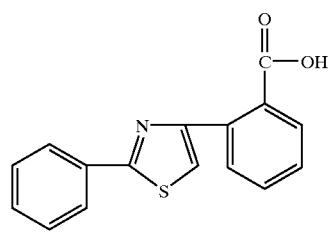

and its HBr salt are excluded, or its salt;

a thiazole derivative represented by formula (I-7):

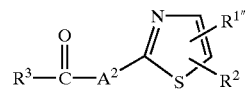
(I-7)

wherein $R^{1''}$ is an optionally substituted aromatic hydrocarbon group; $R^2$ is hydrogen or an optionally substituted hydrocarbon group; $A^2$ is an optionally substituted aromatic hydrocarbon group except for an aromatic hydrocarbon group substituted by a group having an intervening hetero atom; $R^3$ is a group represented by the formula: $-OR^5$ wherein $R^5$ is hydrogen or an optionally substituted hydrocarbon group, or $-NR^6R^7$ wherein $R^6$ and $R^7$ are same or different and each is hydrogen or an optionally substituted hydrocarbon group, or $R^6$ and $R^7$ may be taken together with an adjacent nitrogen atom to form a ring, provided that compounds represented by the formulae:

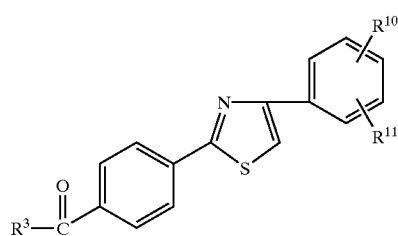

wherein the combination of the definitions is any of the following: both of $R^{10}$ and $R^{11}$ are hydrogen atoms and $R^3$ is hydroxyl group or methoxy group; $R^{10}$ is chlorine substituting at 2- or 4-position, $R^{11}$ is hydrogen or $R^3$ is hydroxyl group or methoxy group;, $R^{10}$ is chlorine substituting at 2- or 3-position, $R^{11}$ is chlorine substituting at 4-position and $R^3$ is hydroxyl group or methoxy group; $R^{10}$ is fluorine substituting at 4-position, $R^{11}$ is hydrogen and $R^3$ is hydroxyl group or methoxy group; $R^{10}$ is a methoxy group substituting at 4-position, $R^{11}$ is hydrogen and $R^3$ is hydroxyl group or methoxy group; $R^{10}$ is a $CF_3$ group substituting at 3-position, $R^{11}$ is hydrogen and $R^3$ is hydroxyl group or methoxy group,

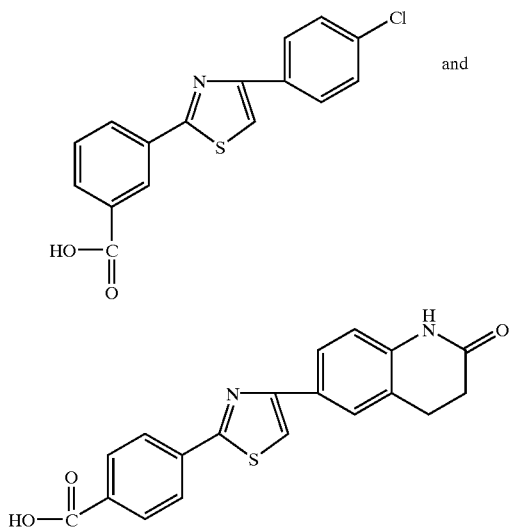

and are excluded, or its salt; and
a thiazole derivative represented by formula (I-8):

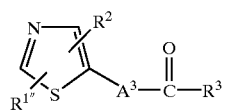
(I-8)

wherein $R^{1''}$ is an optionally substituted aromatic hydrocarbon group; $R^2$ is hydrogen or an optionally substituted hydrocarbon group; $A^3$ is an optionally substituted aromatic hydrocarbon group; $R^3$ is a group represented by the formula: $-OR^5$ wherein $R^5$ is hydrogen or an optionally substituted hydrocarbon group, or $-NR^6R^7$ wherein $R^6$ and $R^7$ are same or different and each is hydrogen or an optionally substituted hydrocarbon group, or $R^6$ and $R^7$ may be taken together with an adjacent nitrogen atom to form a ring, provided that a compound represented by the formula:

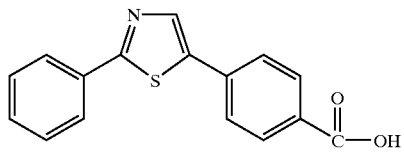

is excluded, or its salt.

A compound represented by formula (I-1) is preferably an oxazole derivative represented by the formula:

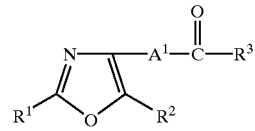

or its salt.

A compound represented by formula (I-2) is preferably an oxazole derivative wherein $R^2$ is hydrogen or an optionally substituted non-aromatic hydrocarbon group except for a non-aromatic hydrocarbon group which is substituted by an optionally esterified carboxyl group and $R^3$ is a group represented by the formula: $-OR^5$ or its salt A compound represented by formula (I-3) is preferably an oxazole derivative wherein $A^1$ is a phenyl group having a $-COR^3$ group in a meta- or para-position, provided that compounds represented by the formulae:

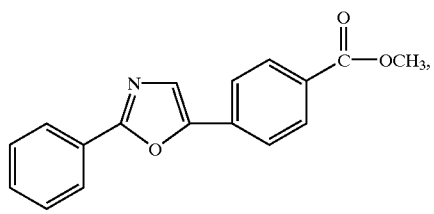

-continued

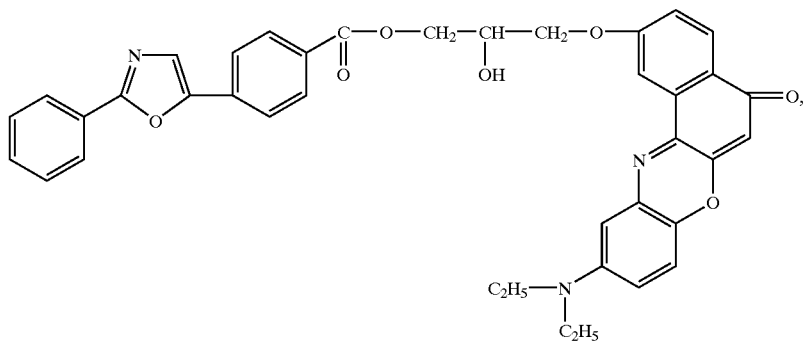

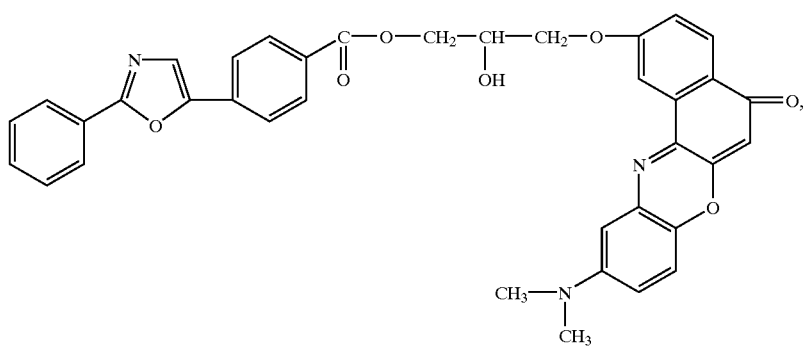

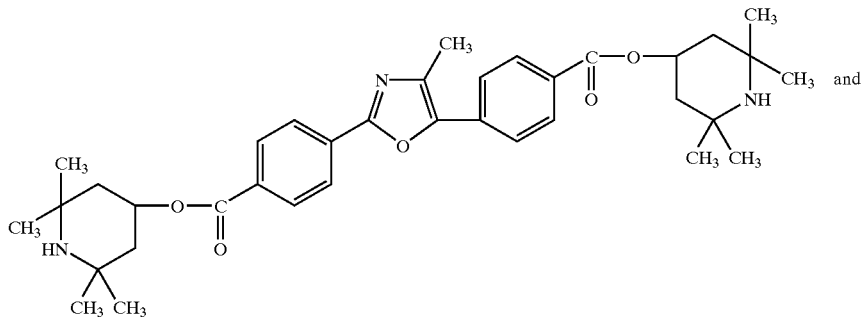

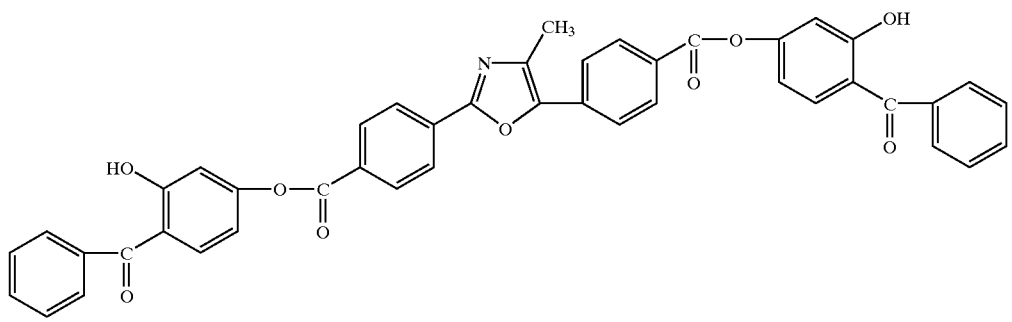

are excluded, or its salt; and more preferably an oxazole derivative wherein $R^3$ is OH, or its salt.

A compound represented by formula (I-4) is preferably an imidazole derivative wherein $R^1$ is an optionally substituted aromatic hydrocarbon group except for an aromatic hydrocarbon group substituted by a sulfo group, or its salt.

A compound represented by formula (I-5) is preferably an imidazole derivative wherein $R^{1''}$ is an optionally substituted aromatic hydrocarbon, and said aromatic hydrocarbon group does not form a condensed ring, provided that a compound represented by the formula:

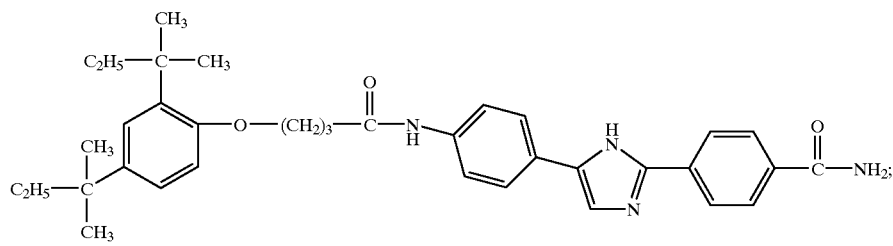

is excluded, or its salt; and more preferably an imidazole derivative wherein $R^3$ is a group represented by the formula: $-OR^5$.

A compound represented by formula (I-6) is preferably a thiazole derivative wherein $R^{1'}$ is an aromatic hydrocarbon group having at least two substituents, or its salt; or a thiazole derivative wherein $R^{1'}$ is phenyl group having a substituent in an ortho- or meta-position, or its salt.

A compound represented by formula (I-7) is preferably a thiazole derivative wherein $R^2$ is an optionally substituted hydrocarbon group, or its salt; or a thiazole derivative wherein $R^{1''}$ is an aromatic hydrocarbon group having at least two substituents, or its salt; and more preferably a thiazole derivative wherein $A^2$ is phenyl group having a substituent $-COR^3$ group in an ortho-position, or its salt.

A compound represented by formula (I-8) is preferably a thiazole derivative wherein $R^{1''}$ is a substituted aromatic hydrocarbon group, or its salt.

A salt of a compound represented by formula (I) is preferably a pharmacologically acceptable salt, and exemplified by a salt with an inorganic base, a salt with an organic base, a salt with an inorganic acid, a salt with an organic acid, and a salt with a basic or acidic amino acid.

Examples of a preferred salt with an inorganic base include an alkaline metal salt such as a sodium salt and a potassium salt; an alkaline earth metal salt such as a calcium salt and a magnesium salt; as well as an aluminum salt and an ammonium salt.

Examples of a preferred salt with an organic base include a salt with trimethylamine, triethylamine, pyridine, picoline, ethanolamine, diethanolamine, triethanolamine, dicyclohexylamine, N,N-dibenzylethylenediamine and the like.

Examples of a preferred salt with an inorganic acid include a salt with hydrochloric acid, hydrobromic acid, nitric acid, sulfuric acid, phosphoric acid and, the like.

Examples of a preferred salt with an organic include a salt, with formic acid, acetic acid, trifluoroaceticd acid, fumaric acid, oxalic acid, tartaric acid, maleic acid, citric acid, succinic acid, malic acid, methanesulfonic acid, benzenesulfonic acid, p-toluenesulfonic acid and the like.

Examples of a preferred salt with a basic amino acid include a salt with arginine, lysine, ornithine and the like, while examples of a preferred salt with an acidic amino acid include a salt with aspartic acid, glutamic acid and the like.

Among the above salts, preferred are a sodium salt, a potassium salt, a hydrochloride and the like.

A compound represented by formula (I) or its salt (hereinafter simply abbreviated as Compound (I)) can be formulated in accordance with a known method, if necessary by admixing with a pharmacologically acceptable carrier, into a pharmaceutical composition of the invention, which can be safely administered to a mammal (e.g., human, cattle, horse, pig, monkey, dog, rabbit, cat, rat, mouse, etc.).

As the pharmacologically acceptable carrier, various organic and inorganic carriers commonly used as a pharmaceutical material are employed. These are incorporated as an excipient, a lubricant, a binder and a disintegrant for a solid dosage form; and a solvent, a solubilizer, an osmotic agent, a buffering agent and a soothing agent for a liquid dosage form. A pharmaceutical additive such as a preservative, an antioxidant, a colorant and a sweetener, may also be employed if necessary.

Preferred examples of the excipient include lactose, sugar, D-mannitol, D-sorbitol, starch, gelatinized starch, crystalline cellulose, low-substituted hydroxypropyl cellulose, sodium carboxymethyl cellulose, gum arabic, dextrin, pullulan, light anhydrous silicic acid, synthetic aluminum silicate, and magnesium aluminate metasilicate.

Preferred examples of the lubricant include magnesium stearate, calcium stearate, talc, colloidal silica.

Preferred examples of the binder include gelatinized starch, sucrose, gelatin, gum arabic, methyl cellulose, carboxymethyl cellulose, sodium carboxymethyl cellulose, crystalline cellulose, sugar, D-mannitol, trehalose, dextrin, pullulan, hydroxypropyl cellulose, hydroxypropylmethyl cellulose, polyvinylpyrrolidone.

Preferred examples of the disintegrant include lactose, sugar, starch, carboxymethyl cellulose, calcium carboxymethyl cellulose, crosscarmelose sodium, sodium carboxymethyl starch, light anhydrous silicic acid, low-substituted hydroxypropyl cellulose.

Preferred examples of the solvent include water for injection, physiological saline, Ringer's solution, an alcohol, propylene glycol, polyethylene glycol, sesame oil, corn oil, olive oil, and cottonseed oil. include polyethylene glycol, propylene glycol, D-mannitol, trehalose, benzyl benzoate, ethanol, tris-aminomethane, cholesterol, triethanolamine, sodium carbonate, sodium citrate, sodium. salicylate, sodium acetate.

Preferred examples of the suspending agent include a surfactant such as stearyltriethanolamine, sodium laurylsulfate, laurylaminopbropionic acid, lecithin, benzalkonium chloride, benzethonium chloride and glycerin monostearate; a hydrophilic polymer such as polyvinylalcohol, polyvinylpyrrolidone, sodium carboxymethyl cellulose, methyl cellulose, hydroxymethyl cellulose, hydroxyethyl cellulose and hydroxypropyl cellulose; polysolvate and polyoxyethylene hardened castor oil.

Preferred examples of the osmotic agent include sodium chloride, glycerin, D-mannitol, D-sorbitol, glucose.

Preferred examples of the buffering agent include a buffer solution of phosphate, acetate, carbonate, citrate.

Preferred examples of the soothing agent include benzyl alcohol.

Preferred examples of the preservative include p-oxybenzoate, chlorobutanol, benzyl alcohol, phenethyl alcohol, dehydroacetic acid, sorbic acid.

Preferred examples of the antioxidant include sulfite, ascorbate.

Preferred examples of the colorant include a water-soluble edible tar dye (e.g., edible red No.2 and No.3, edible yellow No.4 and No.5, edible blue No.1 and No.2), a water-insoluble lake dye (e.g., an aluminum salt of the above water-soluble edible tar dye), a naturally-occurring dye (e.g., β-carotene, chlorophyll, iron oxide red) and the like.

Preferred examples of the sweetener include saccharin sodium, dipotassium glycyrrhizinate, aspartame, and stevia.

A pharmaceutical composition of the invention can be safely administered as an oral preparation such as tablets, capsules (including soft capsules and microcapsules), granules, powders, syrups, emulsions and suspensions; and as a parenteral preparation such as injections (e.g., subcutaneous injections, intravenous injections, intramuscular injections, intraperitoneal injections), drip infusions, external application forms (e.g., nasal preparations, percutaneous preparations, ointments), suppositories (e.g., rectal suppositories, vaginal suppositories), pellets and drip infusions.

A pharmaceutical composition of the invention can be prepared by a conventional, method in the field of pharmaceutical techniques, for example, by a method described in Japanese Pharmacopoeia. A typical method for preparing a pharmaceutical composition is detailed below.

For example, an oral preparation is prepared by adding to an active ingredient, for example, an excipient, a disintegrant, a binder or a lubricant, and compression molding, if necessary followed by coating using a coating base by a per se known method for the purpose of taste masking, enteric coating or sustained release.

Examples of the coating base include a sugar coating base, a water-soluble film coating base, an enteric film coating base, a sustained release film coating base.

As the sugar coating base, a sugar is employed. Further, one or at least two species selected from talc, precipitated calcium carbonate, gelatin, gum arabic, pullulan, carnauba was can be used in combination.

Examples of the water-soluble film coating base include a cellulose polymer such as hydroxypropyl cellulose, hydroxypropylmethyl cellulose, hydroxyethyl cellulose and methylhydroxyethyl cellulose; a synthetic polymer such as polyvinyl acetal diethylaminoacetate, aminoalkylmethacrylate copolymer E [EUDRAGIT E (trade name), Rohm Pharma] and polyvinyl pyrrolidone; a polysaccharide such as pullulan.

Examples of the enteric film coating base, include a cellulose polymer such as hydroxypropylmethyl cellulose phthalate, hydroxypropylmethyl cellulose acetate succinate, carboxymethylethyl cellulose and cellulose acetate phthalate; an acrylic acid polymer such as methacrylic acid copolymer L [EUDRAGIT L (trade name), Rohm Pharma], methacrylic acid copolymer LD [EUDRAGIT L-30D55 (trade name), Rohm Pharma], methacrylic acid copolymer S [EUDRAGIT S (trade name), Rohm Pharma]; and a naturally-occurring material such as shellac.

Examples of the sustained release film coating base include a cellulose polymer such as ethyl cellulose; and an acrylic acid polymer such as an aminoalkylmethacrylate copolymer RS [EUDRAGIT RS (trade name), Rohm Pharma], ethyl acrylate-methyl methacrylate copolymer suspension [EUDRAGIT NE (trade name), Rohm Pharma].

Two or more of these coating bases described above may be used as being admixed at a suitable ratio. At the time of coating, a shading agent such as titanium oxide and red ferric oxide may be used.

Injections can be prepared by dissolving, suspending or emulsifying an active ingredient in an aqueous solvent (e.g. distilled water, physiological saline, Ringer's solution) or in an oily solvent (e.g., vegetable oil such as olive oil, sesame oil, cottonseed oil and corn oil; propylene glycol) together with a dispersant (e.g. polysorbate 80, polyoxyethylene hardened castor oil 60), polyethylene glycol, carboxymethyl cellulose, sodium alginate), a preservative (e.g., methylparaben, propylparaben, benzylalcohol, chlorobutanol, phenol), an osmotic agent (e.g., sodium chloride, glycerin, D-mannitol, D-sorbitol, glucose). In this case, additives such as solubilizers (e.g., sodium salicylate, sodium acetate), a stabilizer (e.g., human serum albumin) and a soothing agent (e.g., benzyl alcohol) can be used, if necessary.

Compound (I) has a retinoid-related receptor function regulating effect (e.g., retinoid-related receptor function activating effect, retinoid-related receptor function suppressing effect; preferably retinoid-related receptor function activating effect). A retinoid-related receptor used herein means a DNA-binding transcription factor, included in intranuclear receptors, whose ligand is a signal molecule such as an lipid-soluble vitamin, and may be a monomer receptor, a homodimer receptor or a heterodimer receptor. Examples of the monomer receptor include a retinoid O receptor (hereinafter sometimes abbreviated as ROR) α (GenBank Accession No.L14611), ROR β (GenBank Accession No.L14160), ROR γ (GenBank Accession No.U16997); Rev-erb α (GenBank Accession No.M24898); Rev-erb β (GenBank Accession No.L31785); ERR α (Gen Bank Accession No.X51416), ERR β (GenBank Accession No.X51417); Ftz-FI α (GenBank Accession No.S65876), Ftz-FI β (GenBank Accession No.M81385); TIx (GenBank Accession No.S77482);. GCNF (GenBank Accession No.U14666).

Examples of the homodimer receptor include a, homodimer formed from a retinoid X receptor (hereinafter sometimes abbreviated as RXR) α (GenBank Accession No.X52773), RXR β (GenBank Accession No.M84820), RXR γ (GenBank Accession No.U38480); COUPα (GenBank Accession No.X12795), COUPβ (GenBank Accession No.M64497), COUPγ (GenBank Accession No.X12794); TR2α (GenBank-Accession No.M29960), TR2β (GenBank Accession No.L27586); or HNF4α (GenBank Accession No.X76930), HNF4γ (GenBank Accession No.Z49826) and the like.

Examples of the heterodimer receptor include a heterodimer formed from a retinoid X receptor described above (RXRα, RXRβ or RXRγ) and one receptor selected from a retinoid A receptor (hereinafter sometimes abbreviated as RAR) α (GenBank Accession No.X06614), RAR β (GenBank Accession No.Y00291), RAR γ (GenBank Accession No.M24857); a thyroidal hormone receptor (hereinafter sometimes abbreviated as TR) α (GenBank Accession No.M24748), TRβ (GenBank Accession No.M26747); vitamin D receptor (VDR) (GenBank Accession No.J03258); peroxisome proliferator-activated receptor (hereinafter sometimes abbreviated as PPAR) α (GenBank Accession No.L02932), RPARβ (PPARδ) (GenBank Accession No.U10375), PRARγ (GenBank Accession No.L40904); LXRα (GenBank Accession No.U22662), LXRβ (GenBank Accession No.U14534); FXR (GenBank Accession No.U18374); MB67 (GenBank Accession No.L29263); ONR (GenBank Accession No.X75163); and NURα (GenBank Accession No.L13740), NURβ (GenBank Accession No.X75918), NURγ (GenBank Accession No.U12767).

A retinoid-related receptor function regulation employed here means activation or suppression of the function of a retinoid-related receptor. Activation of the function of a retinoid-related receptor means activation of the transcriptional system of a retinoid-related receptor, and a substance capable of such activation can be useful as a retinoid-related receptor ligand, a retinoid-related receptor ligand modulator, a retinoid-related receptor agonist, a modulator of a co-activator of a retinoid-related receptor, and may be any substance which gives a response similar to that generated as a result of the effect of a ligand on a retinoid-related receptor.

On the other hand, a suppression of the function of a retinoid-related receptor means a suppression of the transcriptional system of a retinoid-related receptor, and a substance capable of such suppression can be useful as a retinoid-related receptor antagonist, and may be any substance capable of suppressing a response generated as a result of the effect of a ligand on a retinoid-related receptor.

Compound (I) possesses an excellent function-activating effect especially on retinoid X receptors (RXRα,RXRβ, RXRγ) and peroxisome proliferator-activated receptors (PPARα, PPARβ(PPARδ), PPARγ) among the above retinoid-related receptors, and possesses an excellent function-activating effect on a peroxisome proliferator-activated receptor in a heterodimer receptor formed from a retinoid X receptor and a peroxisome proliferator-activated receptor, preferably a heterodimer receptor formed from RXRα and PPARγ. Accordingly, compound (I) can be used as a peroxisome proliferator-activated receptor ligand or a retinoid X receptor function-activating agent.

A pharmaceutical composition of the invention exhibits almost no side effects such as a body weight increase, and has a hypoglycemic effect, a hypolipidemic effect, a hypoinsulinnemic effect, an insulin sensitivity enhancing effect and an insulin resistance improving effect, thus can be employed as an agent for preventing or treating a retinoid-related receptor-mediating disease, more specifically as an agent for preventing or treating diabetes (e.g., insulin-dependent diabetes, non-insulin-dependent diabetes, gestational diabetes), an agent for preventing or treating hyperlipidemia (e.g., hypertriglyceridemia, hypercholesterolemia, hypo-HDL-cholesterolemia), an anti-obesity agent, anagent for preventing or treating obesity, an insulin sensitivity enhancing agent, an insulin resistance improving agent, an agent for preventing or treating impaired glucose tolerance (IGT), and an agent for preventing transition from impaired glucose tolerance to diabetes.

Further, a pharmaceutical composition of the invention can be used as an agent for preventing or treating diabetic complications (e.g., neuropathy, nephropathy, retinopathy, cataract, macroangiopathy, osteopenia), obesity, osteoporosis, cachexia (e.g., carcinomatous cachexia, tuberculous cachexia, diabetic cachexia, hemopathic cachexia, endocrinopathic cachexia, infectious cachexia or cachexia induced by acquired immunodeficiency syndrome), fatty liver, hypertension, polycystic ovary syndrome, renal diseases (e.g., diabetic nephropathy, glomerular nephritis, glomerulosclerosis, nephrotic syndrome, hypertensive nephrosclerosis, terminal renal disorder), muscular dystrophy, myocardiac infarction, angina pectoris, cerebral infarction, insulin resistant syndrome, syndrome X, hyperinsulinemia-induced sensory disorder, tumor (e.g., leukemia, breast cancer, prostate cancer, skin cancer), arteriosclerosis (e.g., atherosclerosis) and as a pharmaceutical for controlling appetite or food intake.

A compound represented by formula (I) or its salt includes a novel compound such as compounds represented by any of formulae (I-1) to (I-8) or their salts. Such novel compound is employed as a pharmaceutical for treating or preventing inflammatory disease (e.g., chronic rheumatoid arthritis, spondylitis deformans, osteoarthritis, lumbago, gout, postoperative wound inflammation and swelling, neualgia, laryngopharyngitis, cystitis, hepatitis, pneumonia, pancreatitis) as well as the above diseases.

While the dose of a pharmaceutical composition of the invention may vary depending on an administration subject, an administration route, a target disease and a clinical condition, a compound of the invention as an active ingredient may be administered to an adult orally at a single dose usually of 0.05 to 100 mg/kg body weight, preferably 0.1 to 10 mg/kg body weight. This dose is administered preferably once to three times a day.

On the other hand, on the occasion of a parenteral administration, administration is conducted not more than once a day. A daily dose may be the same as on the occasion of an oral administration.

A pharmaceutical composition of the invention ca be used concomitantly with a drug such as an agent for treating diabetes, an agent for treating diabetic complications, an antihyperlipdemic agent, a hypotensive agent, an anti-obesity agent, a diuretic, a chemotherapeutic agent, an immunotherapeutic agent (hereinafter abbreviated as a concomitant agent). In such case, the timing of administering a pharmaceutical composition of the invention and a concomitant agent are not particularly limited, and these may be given simultaneously or at staggered times. The dose of a concomitant agent may be selected appropriately based on the clinical dose. The ratio of compound (I) employed in a pharmaceutical composition of the invention and a concomitant agent may vary depending on an administration subject, an administration route, a target disease, a clinical condition and a combination. For example, when the administration subject is a human, the concomitant agent can be used in an amount of 0.01 to 100 parts by weight of one part by weight of compound (I).

Examples of an agent for treating diabetes include an insulin preparation (e.g., an animal insulin preparation extracted from a bovine or porcine pancreas; a human insulin preparation synthesized by a genetic engineering technique using $E.coli$ or yeast), an insulin sensitivity-enhancing agent (e.g., pioglitazone hydrochloride, troglitazone, rosiglitazone), an α-glucosidase inhibitor (e.g., voglibose, acarbose, miglitol, emiglitol), a biguanide (e.g., phenformin, metformin, buformin), or a sulfonylurea (e.g., tolbutamide, glibenclamide, glicazide, chlorpropamide, tolazamide, acetohexamide, glyclopyramide, glimepiride), or other insulin secretagogues (e.g., repaglinide, senaglinide, mitiglinide, GLP-1).

Examples of the agent for treating diabetic complications include an aldose reductase inhibitor (e.g., tolrestat, epalrestat, zenarestat, zopolrestat, minalrestat, fidarestat, SK-860, CT-112), a neurotrophic factor (e.g., NGF, NT-3, BDNF), an active oxygen scavenger (e.g., thioctic acid), a cerebral vasodilator (e.g., tiapuride, mexiletine).

Examples of the antihyperlipidemic agent include a statin compound which is a cholesterol synthesis inhibitor (e.g., pravastatin, simvastatin, lovastatin, atorvastatin, fluvastatin, cerivastatin), a squalene synthesis inhibitor or a fibrate compound (e.g., bezafibrate, clofibrate, simfibrate, clinofibrate) having a triglyceride lowering action.

Examples of the hypotensive agent include an angiotensin converting enzyme inhibitor (e.g., captopril, enalapril, delapril) or an angiotensin II antagonist (e.g., losartan, candesartantcilexetil, eprosartan, valsartan, telmisartan, irbesartan, tasosartan).

Examples of the anti-obesity agent include an anti-obesity agent central acting on the central nervous system (e.g., dexfenflutramine, fenfluramine, phentermine, sibutramine, amfepramone, dexamphetamine, mazindol, phenylpropanolamine, clobenzorex), a pancreatic lipase inhibitor (e.g., orlistat), β3 agonist: (e.g., CL-316243, SR-58611-A, UL-TG-307, SB-226552, AJ-9677, BMS-196085), an anorectic peptide (e.g., leptin, CNTF (ciliary neurotrophic factor)), cholecystokinin agonist (e.g., lintitript, FPL-15849).

Examples of the diuretic include a xanthine derivative (e.g., theobromine sodium salicylate, theobromine calcium salicylate), a thiazide preparation (e.g., ethiazide, cyclopenthiazide, trichlormethiazide, hydrochlorothiazide, hydroflumethiazide, pentylhydrochlorothiazide, penflutizide, polythiazide, methyclothiazide), an anti-aldosterone preparation (e.g., spironolactone, triamterene), a carbonate dehydratase inhibitor (e.g., acetazolamide), a chlorobenzensulfonamide preparation (e.g., chlorthalidone, mefruside, indapamide), azosemide, isosorbide, ethacrynic acid, piretanide, bumetanide, furosemide.

Examples of the chemotherapeutic agent include an alkylating agent (e.g., cyclophosphamide, ifosamide), a metabolism antagonist (e.g., methotrexate, 5-fluorouracil), an anticancer antibiotic (e.g., mitomycin, adriamycin), a plant-derived anticancer agent (e.g., vincristine, vindesine, taxol), cisplatin, carboplatin, ethopoxide. Among these, a 5-fluorouracil derivative such as Furtulon and Neo-Furtulon is preferred.

Examples of the immunotherapeutic agent include a microbial or bacterial component (e.g., muramyldipeptide derivative, Picibanil), an immunopotentiator polysaccharide (e.g., lentinan, schizophyllan, krestin), a genetically engineered cytokine (e.g., interferon, interleukin (IL)), a colony-stimulating factor (e.g., granulocyte colony-stimulating factor, erythropoietin). Among these, IL-1, IL-2 and IL-12 are preferred.

Further, an agent whose effect of ameliorating cachexia has been confirmed in animal models or clinically, namely a cyclooxygenase inhibitor (e.g., indomethacin) (Cancer Research, vol. 49, pp.5935–5939, 1989), a progesterone derivative (e.g., megestrol acetate) (Journal of Clinical Oncology, vol. 12, pp. 213–225, 1994), a glucocorticoid (e.g. dexamethasone), a metoclopramide pharmaceutical, a tetrahydrocannabinol pharmaceutical (the above references are applied to both), a fat metabolism ameliorating agent (e.g., eicosapentanoic acid) (British Journal of Cancer, vol. 68, pp. 314–318, 1993), a growth hormone, IGF-1, and an antibody to the cachexia-inducing factor TNF-α, LIF, IL-6 or oncostatin M, can also be used in combination with a pharmaceutical composition of the invention.

Compound (I) employed in a pharmaceutical composition of the invention can be produced by any of the following methods:

Method A

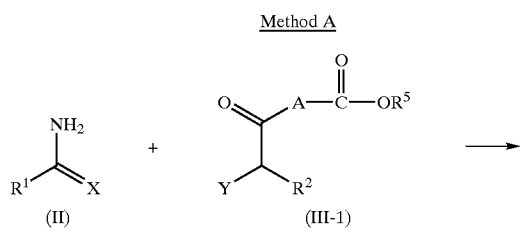
(II)  (III-1)

-continued

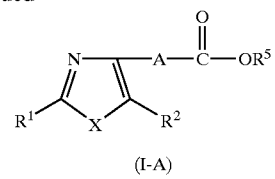
(I-A)

wherein Y is a halogen atom, and other symbols have the same meanings as above.

Examples of the halogen atom for Y include chlorine and bromine.

Compound (II) and compound (III-I) are subjected to a condensation reaction to produce a desired compound (I-A). This reaction is performed without a solvent or in a solvent which does not affect the reaction. Examples of the solvent which does not affect the reaction include an alcohol such as methanol and ethanol; an aromatic hydrocarbon such as toluene and xylene; tetrahydrofuran, pyridine, N,N-dimethylformamide, dimethyl sulfoxide, acetic acid. Two or more of these solvents may be used as a mixture in a suitable ratio. This reaction may be performed in the presence of a base as an acid-removing agent. Examples of such base include an organic amine such as triethylamine, N-methylmorpholine and N,N-dimethylaniline; sodium hydrogen carbonate, potassium carbonate, sodium carbonate, potassium acetate, sodium acetate. The amount of the base used is 1 to 5 molar equivalent relative to compound (II). The reaction temperature is usually about 0 to 200° C., preferably 30 to 150° C. The reaction time is usually 0.5 to 20 hours. The desired compound (I-A) thus obtained can be isolated and purified by a known isolation and purification method such as concentration, concentration under reduced pressure, solvent extraction, crystallization, recrystallization, partition and chromatography.

Method B

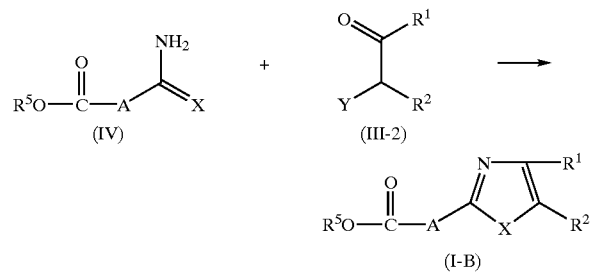
(IV)  (III-2)
(I-B)

wherein each symbol has the same meanings as above.

Compound (IV) and compound (III-2) are subjected to a condensation reaction to produce a desired compound (I-B). This reaction may be performed by a similar method to Method A. The desired compound (I-B) thus obtained can be isolated and purified by a known isolation and purification method such as concentration, concentration under reduced pressure, solvent extraction, crystallization, recrystallization, partition and chromatography.

Method C

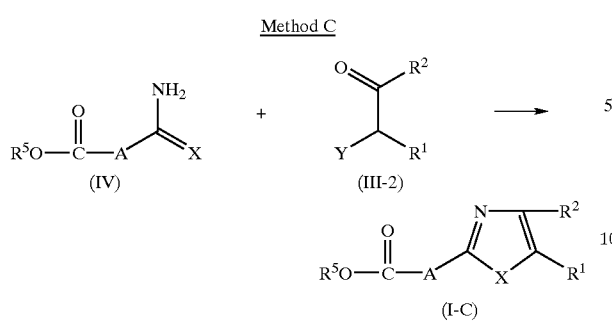

wherein each symbol has the same meanings as above.

Compound (IV) and compound (III-3) are subjected to a condensation reaction to produce a desired compound (I-C). This reaction may be performed by a similar method to Method A. The desired compound (I-C) thus obtained can be isolated and purified by a known isolation and purification method such as concentration, concentration under reduced pressure, solvent extraction, crystallization, recrystallization, partition and chromatography.

Method D

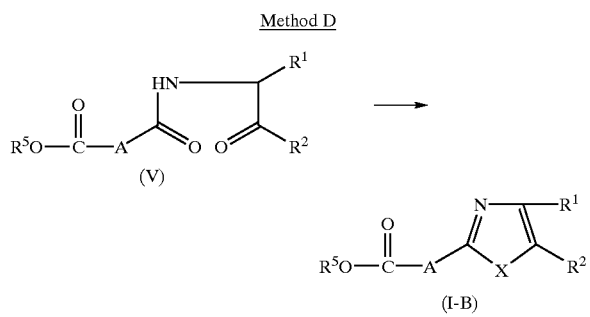

wherein each symbol has the same meanings as above.

Compound (V) is subjected to a cyclization reaction to produce a desired compound (I-B). This reaction is performed in a solvent which does not affect the reaction. Examples of the solvent which does not affect the reaction include an alcohol such as methanol and ethanol; an aromatic hydrocarbon such as toluene and xylene; an ether such as tetrahydrofuran; an organic amine such as pyridine; an amide such as N,N-dimethylformamide; a sulfoxide such as dimethyl sulfoxide; an organic carboxylic acid such as acetic acid. Two or more of these solvents may be used as a mixture in a suitable ratio.

When X is O in compound (V), this reaction is performed in the presence of a dehydrating agent. Examples of such dehydrating agent include sulfuric acid, acetic anhydride, phosphorus pentoxide, phosphorus oxychloride. While the amount of the dehydrating agent used is usually 1 to 50 molar equivalents relative to compound (V), a larger amount may also be employed in some cases.

When X is S, the reaction is performed in the presence of a sulfurizing agent. Examples of such sulfurizing agent include phosphorus pentasulfide, Lawesson's reagent, Davy reagent. The amount of the sulfurizing agent used is usually about 1 to 50 molar equivalents relative to compound (V).

When X represents $NR^4$, the reaction is performed in the presence of an amine ($H_2NR^4$). While the amount of the amine used is usually 1 to 50 molar equivalents relative to compound (V), a larger amount may also be employed in some cases. The reaction temperature is usually about 0 to 200° C., preferably 30 to 150° C. The reaction time is usually 0.5 to 20 hours. The desired compound (I-B) thus obtained can be isolated and purified by a known isolation and purification method such as concentration, concentration under reduced pressure, solvent extraction, crystallization, recrystallization, partition and chromatography.

Method E

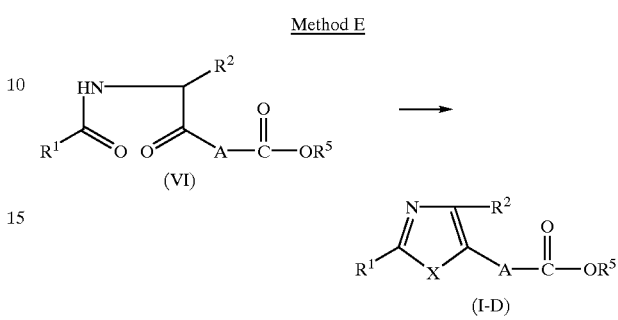

wherein each symbol has the same meanings as above.

Compound (VI) is subjected to a cyclization reaction to produce a desired compound (I-4). This reaction may be performed similarly to Method D. A desired compound (I-4) thus obtained can be isolated and purified by a known isolation and purification method such as concentration, concentration under reduced pressure, solvent extraction, crystallization, recrystallization, partition, chromatography and the like.

Method F

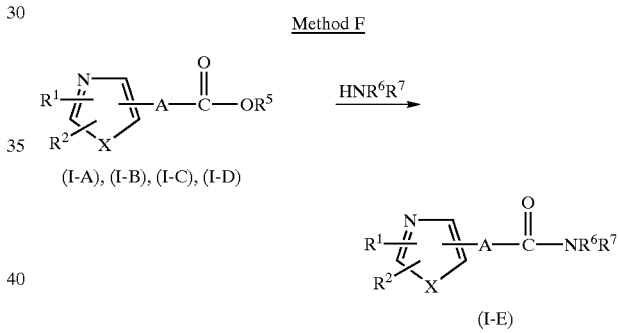

wherein each symbol has the same-meanings as above.

Desired compounds (I-A), (I-B), (I-C) and (I-D) [hereinafter abbreviated as (I-A to D)] is amidated to produce a desired compound (I-E). When $R^5$ represents an alkyl group, the reaction of compound (I-A to D) with an amine derivative ($HNR^6R^7$) is performed in a solvent which does not affect the reaction. Examples of the solvent which does not affect the reaction include an alcohol such as methanol and ethanol; an aromatic hydrocarbon such as toluene and xylene; a tertiary amine such as pyridine; an amide such as N,N-dimethylformamide; a sulfoxide such as dimethyl sulfoxide. Two or more of these solvents may be used as a mixture in a suitable ratio. The reaction temperature is 20 to 200° C., and the reaction is performed for 0.1 to 20 hours. The amount of the amine derivative used is preferably in excess of compound (I-A to D). When $R^5$ is hydrogen atom, used is a method in which compound (I-A to D) and an amine derivative are directly condensed using dicyclohexylcarbodiimide, or a method in which a reactive derivative of compound (I-A to D) such as an acid anhydride, an acid halide (e.g., acid chloride, acid bromide), imidazolide and a mixed acid anhydride (e.g., an anhydrides with methyl carbonate, ethyl carbonate or isobutyl carbonate) is appropriately reacted with an amine derivative.

Among these methods, the most convenient method is one in which an acid halide or a mixed acid anhydride is used. When an acid anhydride is used, the reaction is performed in the presence of a base, in a halogenated hydrocarbon such as chloroform and dichloromethane; an aromatic hydrocarbon such as benzene and toluene; an ester such as ethyl acetate; an ether such as tetrahydrofuran; water; or a mixed solvent thereof. Examples of such base include a tertiary amine such as triethylamine, N-methylmorpholine and N,N-dimethylaniline; and an inorganic base such as sodium hydrogen carbonate, potassium carbonate and sodium carbonate. The amount of the amine derivative used is 1 to 1.5 molar equivalents relative to compound (I-A to D). The reaction temperature is −30 to 100° C. The reaction time is usually 0.5 to 20 hours.

When a mixed acid anhydride is used, compound (I-A to D) is reacted with a chlorocarbonate (e.g., methyl chlorocarbonate, ethyl chlorocarbonate or isobutyl chlorocarbonate) in the presence of a base (e.g., triethylamine, N-methylmorpholine, N,N-dimethylaniline, sodium hydrogen carbonate, potassium carbonate, sodium carbonate), and then reacted with an amine derivative. The amount of the amine derivative used is 1 to 1.5 molar equivalents relative to compound (I-A to D). This reaction is performed in a halogenated hydrocarbon such as chloroform and dichloromethane; an aromatic hydrocarbon such as benzene and toluene; an ester such as ethyl acetate; an ether such as tetrahydrofuran; water; or a mixture thereof. The reaction temperature is −30 to 50° C. The reaction time is 0.5 to 20 hours. The desired compound (I-E) thus obtained can be isolated and purified by a known isolation and purification method such as concentration, concentration under reduced pressure, solvent extraction, crystallization, recrystallization, partition and chromatography.

Starting materials (III-1), (III-2) and (III-3) in Methods A, B and C may be prepared for example by the following Method G:

Method G

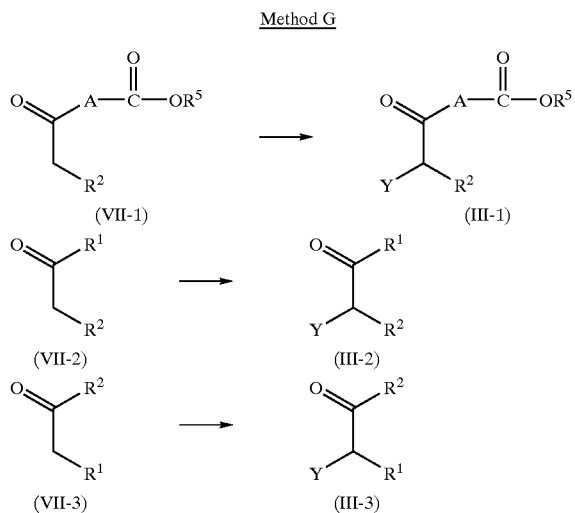

wherein each symbol has the same meanings as above.

Compounds (VII-1), (VII-2) and (VII-3) are halogenated to produce corresponding compounds (III-1), (III-2) and (III-3). This reaction can be performed by a per se known method. This reaction is performed in the presence of a halogenating agent in a solvent which does not affect the reaction. Examples of the halogenating agent include chlorine, bromine, N-chlorosuccinimide, N-bromosuccinimide. The amount of such halogenating agent used is usually about 1 to 2 molar equivalents relative to compound (VII-1), (VII-2) or (VII-3). Examples of the solvent which does not affect the reaction include an alcohol such as methanol and ethanol; an aromatic hydrocarbon such as toluene and xylene; a halogenated hydrocarbon such as dichloromethane and chloroform; an ether such as diethyl ether and tetrahydrofuran; an amide such as N,N-dimethylformamide; a sulfoxide such as dimethyl sulfoxide; a carboxylic acid such as acetic acid. These solvents may be used as a mixture in a suitable ratio. The reaction temperature is usually −20 to 150° C., preferably 0 to 100° C. The reaction time is usually 0.5 to 20 hours. Compound (III-1), (III-2) or (III-3) thus obtained can be isolated and purified by a known isolation and purification method such as concentration, concentration under reduced pressure, solvent extraction, crystallization, recrystallization, partition and chromatography.

The starting compound (V) in Method D may be prepared for example by the following Method H:

Method H

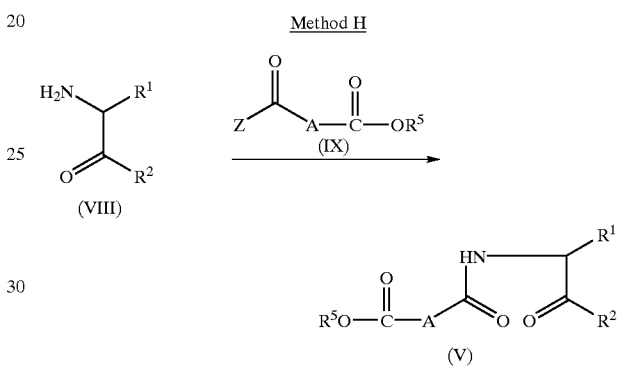

wherein Z is OH or a halogen atom, and other symbols have the same meanings as above. Examples of the halogen atom for Z include chlorine and bromine.

In this reaction, compound (VIII) is acylated with compound (IV) to produce compound (V). This acylation reaction can be performed by a per se known method. For example, used is a method in which compound (VIII) is directly condensed with a carboxylilc acid derivative (IX:Z=OH) fussing a condensing agent such as dicyclohexylcarbodiimide, or a method in which a reactive derivative of the carboxylic acid derivative such as an acid anhydride, an acid halide (acid chloride, acid bromide), imidazolide and a mixed acid anhydride (e.g., an anhydride with methylcarbonate, ethylcarbonate or isobutylcarbonate) is reacted appropriately with compound (VIII). Among these methods, the most convenient method is that in which an acid halide or a mixed acid anhydride is used. When an acid anhydride or a mixed acid anhydride is used, the reaction is performed in the presence of a base in a solvent which does not affect the reaction such as chloroform, dichloromethane, benzene, toluene, ethyl acetate and tetrahydrofuran. Examples of the base include triethylamine, N-methylmorpholine, N,N-dimethylaniline, sodium hydrogen carbonate, potassium carbonate, sodium carbonate. The amount of the acid chloride or the acid anhydride used is 1 to 5 molar equivalents relative to compound (VIII). The reaction temperature is usually −50 to 150° C., preferably −30 to 100° C. The reaction time is usually 0.5 to 20 hours. Compound (V) thus obtained can be isolated and purified by a known isolation and purification method such as concentration, concentration under reduced pressure, solvent extraction, crystallization, recrystallization, partition and chromatography.

The starting compound (VI) in Method E may be produced for example by the following Method I:

Method I

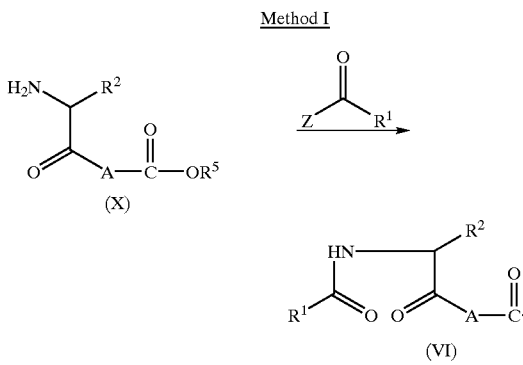

wherein each symbol has the same meanings as above.

Compound (X) is subjected to cyclization to produce compound (I). This reaction may be performed by a similar method to Method H. Compound (VI) thus obtained can be isolated and purified by a known isolation and purification method such as concentration, concentration under reduced pressure, solvent extraction, crystallization, recrystallization, partition and chromatography.

The starting compound (IV) in Method B or C may be produced for example by the following Method J:

Method J

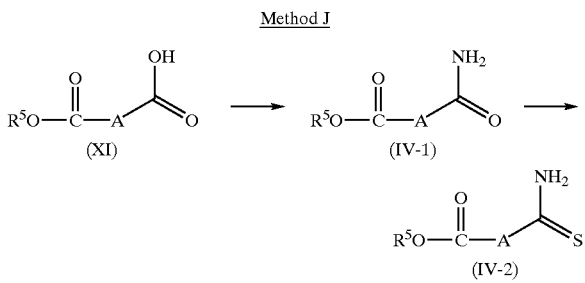

wherein each symbol has the same meanings as above.

Compound (XI) is amidated to produce compound (IV-1). This reaction can be performed by a per se known method. For example, used is a method in which compound (XI) is converted into a reactive derivative such as an acid anhydride, anacid halide (acid chloride, acid bromide), imidazolide or a mixed acid anhydride (e.g., an anhydride with methylcarbonate, ethylcarbonate or isobutylcarbonate), and then reacted appropriately with ammonia. Among these methods, the most convenient method is that in which an acid halide or a mixed acid anhydride is used. When an acid anhydride or a mixed acid anhydride is used, the reaction is performed in the presence of a base in a solvent which does not affect the reaction. Examples of the base include a tertiary amine such as triethylamine, N-methylmorpholine and N,N-dimethylaniline; sodium hydrogen carbonate, potassium carbonate, sodium carbonate. As the solvent, used are a halogenated hydrocarbon such as chloroform and dichloromethane; an aromatic hydrocarbon such as benzene and toluene; an ester such as ethyl acetate; an ether such as tetrahydrofuran. Ammonia may be gaseous or aqueous and is used in an amount usually of about 1 molar equivalent to a large excess. The reaction temperature is usually −50to 150° C., preferably −30 to 100° C. The reaction time is usually 0.5 to 20 hours. Subsequently, compound (IV-1) is thiocarbonylated to produce compound (IV-2). This reaction can be performed by a per se known method. For example, the reaction can be performed in the presence of a sulfurizing agent in a solvent which does not affect the reaction. Examples of such sulfurizing agent include phosphorus pentasulfide, Lawesson's reagent, Davy reagent. The amount of the sulfurizing agent used is usually about 1 to 50 molar equivalents relative to compound (IV-1). Examples of the solvent include an aromatic hydrocarbon such as toluene and xylene; a halogenated hydrocarbon such as dichloromethane and chloroform; an ether such as diethyl ether and tetrahydrofuran; a tertiary amine such as pyridine; an amide such as N,N-dimethylformamide; a sulfoxide such as dimethyl sulfoxide. The reaction temperature is usually 0 to 200° C., preferably about 30 to 150° C. The reaction time is usually 0.5 to 20 hours. Compound (IV-1) or (IV-2) thus obtained can be isolated and purified by a known isolation and purification method such as concentration, concentration under reduced pressure, solvent extraction, crystallization, recrystallization, partition and chromatography.

As hereunder, the present invention is further described by way of Reference Examples, Examples and Experimental Examples. In the following descriptions, % means percent by weight unless otherwise specified, and a genetic engineering procedure was in accordance with a method described in Molecular Cloning [Maniatis et al, Cold Spring Harbor Laboratory, 1989] or a protocol attached to a reagent.

REFERENCE EXAMPLE 1

Human PPAR γ Gene Cloning

A human PPARγ gene was cloned using a heart cDNA (produced by Toyobo Co., Ltd., trade name: QUICK-Clone cDNA) as a template by means of a PCR method employing a primer set shown below which was prepared with reference to the base sequence of PPARγ gene reported by Greene et al (Gene Expr., 1995, Vol.4(4–5), page 281–299).

PAG-U:
5'-GTGGGTACCGAAATGACCATGGTTGACACA-GAG-3' (Sequence ID Number: 1)

PAG-L:
5'-GGGGTCGACCAGGACTCTCTGCTAGTACAA-GTC-3' (Sequence ID Number: 2)

The PCR reaction was performed by Hot Start method using AmpliWax PCR Gem 100 (produced by TAKARA SHUZO CO., LTD.). First, 2 μl of 10×LA PCR Buffer, 3 μl of 2.5 mM dNTP solution, 2.5 μl each of 12.5 μM primer solutions and 10 μl of sterilized distilled water were mixed to obtain a bottom layer solution mixture. 1 μl of human heart cDNA (1 ng/ml) as a template, 3 μl of 10×LA PCR Buffer, 1 μl of 2.5 mM dNTP solution, 0.5 μl of TaKaRa LA Taq DNA polymerase (produced by TAKARA SHUZO CO., LTD.) and 24.5 μl of sterilized distilled water were mixed to obtain a top layer solution mixture.

To the bottom layer solution mixture described above, added was one unit of AmpliWax PCR Gem 100 (produced by TAKARA SHUZO CO., LTD.), which was treated at 70° C. for 5 minutes and then in ice for 5 minutes. Then the top layer solution mixture was added to the mixture to prepare the reaction mixture of PCR. A tube containing the reaction mixture was set on a thermal cycler (produced by Perkin Elmer, USA) and treated at 95° C. for 2 minutes. After repeating the cycle of 95° C. for 15 seconds and 68° C. for 2 minutes a further 35 times, the tube was treated at 72° C. for 8 minutes.

The PCR product thus obtained was subjected to electrophoresis on agarose gel (1%), and 1.4 kb DNA fragment containing PPARγ gene was recovered from the gel, and then inserted into pT7 Blue-T vector (produced by TAKARA SHUZO CO., LTD.) to obtain a plasmid pTBT-hPPARγ.

REFERENCE EXAMPLE 2

Human RXR α Gene Cloning

A human RXRα gene was cloned using a kidney cDNA (produced b Tyobo Co., Ltd., trade name: QUICK-Clone cDNA) as a template by means of a PCR method employing a primer se shown below which was prepared with reference to the base sequence of RXRα gene reported by Mangelsdorf, D. J. et al (Nature, 1990, Vol. 345 (6272), page 224–229).

XRA-U:
   5'-TTAGAATTCGACATGGACACCAAACATTTCC-TG-3' (Sequence ID Number: 3)

XRA-L:
   5'-CCCCTCGAGCTAAGTCATTTGGTGCGGCGC-CTC-3' (Sequence ID Number: 4)

The PCR reaction was performed by Hot Start method using AmpliWax PCR Gem 100 (produced by TAKAEA SHUZO CO., LTD.). First., 2 μl of 10×LA PCR Buffer, 3 μl of 2.5 mM dNTP solution, 2.5 μl each of 12.5 μM primer solutions and 10 μl of sterilized distilled water were mixed to obtain a bottom layer solution mixture. 1 μl of human kidney cDNA (1 ng/ml) as a template, 3 μl of 10×LA PCR Buffer, 1 μl of 2.5 mM dNTP solution, 0.5 μl of TaKaRa LA Taq DNA polymerase (produced by TAKARA SHUZO CO., LTD.) and 24.5 μl of sterilized distilled water-were mixed to obtain a top layer solution mixture.

To the bottom layer solution mixture described above, added was one unit of AmpliWax PCR Gem 100 (produced by TAKARA SHUZO CO., LTD.), which was treated at 70° C. for 5 minutes and then in ice for 5 minutes. Then, the top layer solution mixture was added to the mixture to prepare the reaction mixture of PCR. A tube containing the reaction mixture was set on a thermal cycler (produced by Perkin Elmer, USA) a treated at 95° C. for 2 minutes. After repeating the cycle of 95° C. for 15 seconds and 68° C. for 2 minutes a further 35 times, the tube was treated at 72° C. for 8 minutes.

The PCR product thus obtained was subjected to electrophoresis on agarose gel (1%), and 1.4 kb DNA fragment containing RXRα gene was recovered from the gel, and then inserted into pT7 Blue-T vector (produced by TAKARA SHUZO CO., LTD.) to obtain a plasmid pTBT-hRXRα.

REFERENCE EXAMPLE 3

Construction of Plasmids for Expressing Human PPARγ, RXRα

A 7.8 kb FspI-NotI fragment of plasmid pVgRXR (produce by Invitrogen, USA) was ligated to a 0.9 kb FspI-NotI fragment containing RXRα gene of plasmid pTBT-hRXRα obtained in Reference Example 2 to prepare plasmid pVgRXR2. Then, pVgRXR2 was digested with BstXI and then treated with T4DNA polymerase (produced by TAKARA SHUZO CO., LTD.) to obtain a blunt terminal. Then digestion at KpnI gave a 6.5 kb DNA fragment.

On the other hand, plasmid pTBT-hPPARγ obtained in Reference Example 1 was digested with Sal I and then treated with T4DNA polymerase (produced by TAKARA SHUZO CO., LTD.) to obtain a blunt terminal. Then digestion at KpnI gave a 1.4 kb DNA fragment containing human PPARγ gene.

Both DNA fragments were ligated to construct plasmid pVgRXR2-hPPARγ.

REFERENCE EXAMPLE 4

Construction of Reporter Plasmids

A DNA fragment containing PPAR-responding element (PPRE) of an acyl CoA oxidase was prepared using the following 5'-terminal phosphorylated synthetic DNA.

PPRE-U:
   5'-pTCGACAGGGGACCAGGACAAAGGTCACGT-TCGGGAG-3' (Sequence ID Number: 5)

PPRE-L:
   5'-pTCGACTCCCGAACGTGACCTTTGTCCTGGT-CCCCTG-3' (Sequence ID Number: 6)

First, PPRE-U and PPRE-L were annealed and inserted to Sal I site of plasmid pBlueScript SK+. By determining the base sequence of the inserted fragment, plasmid pBSS-PPRE4 in which 4 PPREs were ligated in tandem was selected.

A HSV thymidine kinase minimum promoter (TK promoter): region was cloned using pRL-TK vector (produced by Promega, USA) as a template by means of a PCR method employing a primer set shown below which was prepared with reference to the base sequence of the promoter region of thymidine kinase reported by Luckow, B et al. (Nucleic Acids Res., 1987, Vol.15(13), p.5490)

TK-U: 5'-CCCAGATCTCCCCAGCGTCTTGTCATTG-3' (Sequence ID Number: 7)

TK-L: 5'-TCACCATGGTCAAGCTTTTAAGCGGGTC-3' (Sequence ID Number: 8)

The PCR reaction was performed by Hot Start method using AmpliWax PCR Gem 100 (TAKARA SHUZO CO., LTD.). First, 2 μl of 10×LA PCR Buffer, 3 μl of 2.5 mM dNTP solution, 2.5 μl each of 12.5 μM primer solutions and 10 μl of sterilized distilled water were mixed to obtain a bottom layer solution mixture. 1 μl of pRL-TK vector (produced by Promega, USA) as a template, 3 μl of 10×LA PCR Buffer, 1 μl of 2.5 mM dNTP solution, 0.5 μl of TaKaRa LA Taq DNA polymerase (produced by TAKARA SHUZO CO., LTD.) and 24.5 μl of sterilized distilled water were mixed to obtain a top layer solution mixture.

To the bottom layer solution mixture described above, added was one unit of AmpliWax PCR Gem 100 (produced by TAKARA SHUZO CO., LTD.), which was treated at 70° C. for 5 minutes and then in ice for 5 minutes. Then, the top layer solution mixture was added to the mixture to prepare the reaction mixture of PCR. A tube containing the reaction mixture was set on a thermal cycler (produced by Perkin Elmer, USA) and treated at 95° C. for 2 minutes. After repeating the cycle of 95° C. for 15 seconds and 68° C. for 2 minutes a further 35 times, the tube was treated at 72° C. for 8 minutes.

The PCR product thus obtained was subjected to electrophoresis on agarose gel (1%), and 140 b DNA fragment containing TK promoter was recovered from the gel, and then inserted into pT7 Blue-T vector (produced by TAKARA SHUZO CO., LTD.). By digesting the plasmid thus obtained with the restriction enzymes Bgl II and NcoI, a fragment containing TK promoter was obtained, which was ligated to the Bgl II-NcoI fragment of plasmid pGL3-Basic vector (produced by Promega, USA) to obtain plasmid pGL3-TK.

A 4.9 kb NheI-XhoI fragment of plasmid pGL3-TK thus obtained was ligated to a 200 b NheI-XhoI fragment of plasmid pBSS-PPRE4 to obtain piasmid pGL3-4ERPP-TK.

This plasmid pGL3-4ERPP-TK thus obtained was digested with BamHI (produced by TAKARA SHUZO CO., LTD.) and then treated with T4DNA polymerase (produced by TAKARA SHUZO CO., LTD.) to form a blunt terminal, whereby obtaining a DNA fragment.

On the other hand, pGFP-C1 (produced by Toyobo Co., Ltd.) was digested with Bsu36I (NEB) and then treated with T4DNA polmerase (produced by TAKARA SHUZO CO., LTD.) to form a blunt terminal whereby obtaining a 1.6 kb of a DNA fragment.

Both DNA fragments were ligated to construct a reporter plasmid pGL3-4ERPP-TK neo.

REFERENCE EXAMPLE 5

Introduction of Human PPARγ- and RXRα-Expressing Plasmid and Reporter Plasmid into CHO-K1 Cell and Establishment of Expressed Cell After a CHO-K1 cell cultured in a 750 ml tissue culture flask (produced by Corning Costar Corporation, USA) containing HAM F12 medium (produced by NISSUI SEIYAKU) supplemented with 10% Fetal Bovine Serum (produced by Life Technologies, Inc., USA) was scraped by treating with 0.5 g/L trypsin-2 g/L EDTA (ethylenediaminetetraacetic acid)(produced by Life Technologies, Inc., USA), the cell was washed with PBS (phosphate-buffered saline) (produced by Life Technologies, Inc., USA), centrifuged (1000 rpm, 5 minutes) and then suspended in PBS. Subsequently, a DNA was introduced into the cell under the condition shown below using GENE PULSER (produced by Bio-Rad Laboratories, USA).

Namely, to a cuvette having a 0.4 cm gap, added were $8 \times 10^6$ cells and 10 μg of plasmid pVgRXR2-hPPARγ obtained in Reference Example 3 and 10 μg of reporter plasmid pGL3-4ERPP-TK neo obtained in Reference Example 4, which was subjected to electroporation at the voltage of 0.25 kV under the capacitance of 960 μF. Subsequently, the cell was transferred into a HAM F12 medium containing 10% Fetal Bovine Serum and cultured for 24 hours and then the cell was scraped again and centrifuged, and then suspended in HAM F12 medium containing 10% Fetal Bovine Serum supplemented with 500 μg/ml of GENETICIN (produced by Life Technologies, Inc., USA) and 250 μg/ml of ZEOCIN (produced by Invitrogen, USA) and diluted to the density of $10^4$ cells/ml. The cell was inoculated to a 96-well plate (produced by Corning Costar Corporation, USA), which was cultured in a $CO_2$ gas incubator at 37° C., whereby obtaining a GENETICIN- and ZEOCIN-resistant transformant.

Subsequently, after the transformant cell line thus obtained was cultured in a 24-well plate(produced by Corning Costar Corporation, USA), selected was a cell line in which the luciferase was expressed and induced, i.e., PPARγ:RXRα:4ERPP/CHO-K1 cell by addition of 10 μM pioglitazone hydrochloride.

REFERENCE EXAMPLE 6

A mixture of 2-(4-chlorophenyl)-2-oxoethylamine hydrochloride (1.51 g), monomethyl terephalate chloride (1.45 g) and N,N-dimethylacetamide (15 ml) was stirred at room temperature for 2 hours. The reaction mixture was poured into water and extracted with ethyl acetate. The ethyl acetate layer was washed successively with a 1N aqueous solution of sodium hydroxide, 1 N hydrochloric acid and water, and then dried (MgSO₄), concentrated to obtain methyl 4-[N-[2-(4-chlorophenyl)-2-oxoethyl]carbamoyl]benzoate (660 mg, yield: 27%).

NMR (CDCl₃) δ 3.96 (3H, s), 4.95 (1H, d, J=4.5 Hz), 7.25–7.35 (1H, m), 7.52 (2H, d, J=9 Hz), 7.9–8.05 (4H, m), 8.15 (2H, d, J=9 Hz).

REFERENCE EXAMPLE 7

In the same manner as in Reference Example 6, ethyl 4-(2-amino-1-oxoethyl)benzoate hydrochloride and 4-trifluoromethylbenzoyl chloride were condensed to obtain ethyl 4-[2-(4-trifluoromethylbenzoylamino)-1-oxoethyl]benzoate. Yield: 53%. NMR (CDCl₃) δ 1.43 (3H, t, J=7 Hz), 4.43 (2H, q, J=7 Hz), 5.01 (2H, d, J=4 Hz), 7.31 (1H, brs), 7.75 (2H, d, J=8 Hz), 7.95–8.25 (6H, m).

REFERENCE EXAMPLE 8

In the same manner as in Reference Example 6, ethyl 4-(2-amino-1-oxoethyl)benzoate hydrochloride and 4-chlorobenzoyl chloride were condensed to obtain ethyl 4-[2-(4-chlorobenzoylamino)-1-oxoethyl]benzoate. Yield: 54%. NMR (CDCl₃) δ 1.41 (3H, t, J=7 Hz), 4.43 (2H, q, J=7 Hz), 4.99 (2H, d, J=4 Hz), 7.23 (1H, brs), 7.46 (2H, d, J=8.5 Hz), 7.84 (2H, d, J=8.5 Hz), 8.09 (2H, d, J=8.5 Hz), 8.21 (2H, d, J=8.5 Hz).

REFERENCE EXAMPLE 9

A mixture of ethyl 4-(2-phenyl-4-thiazolyl) benzoate (1.67 g), a 1N aqueous solution of sodium hydroxide (10 ml), tetrahydrofuran (10 ml) and ethanol (10 ml) was stirred at 60 to 70° C. for 1 hour. The reaction mixture was poured into 1N hydrochloric acid. The precipitated crystals were collected by filtration and washed with water to obtain 4-(2-phenyl-4-thiazolyl]benzoic acid. The product was recrystallized from tetrahydrofuran-ethanol. Yield: 94%. Pale yellow prisms. Melting Point: 245 to 248° C.

REFERENCE EXAMPLE 10

In the same manner as in Reference Example 9, ethyl 4-[2-(4-chlorophenyl)-4-thiazolyl]benzoate was hydrolyzed to obtain 4-[2-(4-chlorophenyl)-4-thiazolyl]benzoic acid. The product was recrystallized from tetrahydrofutran-hexane. Yield: 82%. Pale yellow prisms. Melting Point: 284 to 285° C.

REFERENCE EXAMPLE 11

In the same manner as in Reference Example 9, ethyl 4-[2-(4-trifluoromethylphenyl)-4-thiazolyl]benzoate was hydrolyzed to obtain 4-[2-(4-trifluromethylphenyl)-4-thiazolyl]benzoic acid. The product was recrystallized from acetone-hexane. Yield: 55%. Yellow prisms. Melting Point: 275 to 276° C.

REFERENCE EXAMPLE 12

In the same manner as in Reference Example 9, ethyl 3-[4-(4-chlorophenyl)-2-thiazolyl]benzoate was hydrolyzed to obtain 3-[4-(4-chlorophenyl)-2-thiazolyl]benzoic acid. The product was recrystallized from tetrahydrofuran-isopropyl ether. Yield: 77%. Pale yellow prisms. Melting Point: 265 to 266° C.

REFERENCE EXAMPLE 13

In the same manner as in Reference Example 9, ethyl 4-[2-(4-chlorophenyl)-5-oxazolyl]benzoate was hydrolyzed to obtain 4-[2-(4-chlorophenyl)-5-oxazolyl]benzoic acid. The product was recrystallized from tetrahydrofuran-hexane. Yield: 61%. Pale yellow prisms. Melting Point: 268 to 270° C.

EXAMPLE 1

A mixture of methyl 4-carbamoylbenzoate (4.67 g), 4-chlorophenacyl bromide (6.50 g) and N,N-dimethylformamide (5 ml) was stirred at 130° C. for 2 hours. Hot ethanol was added to the reaction mixture, which was filtered. The filtrate was cooled to obtain crystals of methyl 4-[4-(4-chlorophenyl)-2-oxazolyl]benzoate (1.45 g, Yield: 18%). The product was recrystallized from ethanol. Pale yellow prisms. Melting Point: 183 to 184° C.

EXAMPLE 2

In the same manner as in Example 1, methyl 4-carbamoylbenzoate was reacted with 4-trifluoromethylphenacyl bromide to obtain methyl 4-[4-(4-trifluoromethylphenyl)-2-oxazolyl]benzoate. The product was recrystallized from ethanol. Yield: 30%. Pale yellow prisms. Melting Point: 182 to 183° C.

EXAMPLE 3

In the same manner as in Example 1, methyl 4-carbamoylbenzoate was reacted with 4-methoxyphenacyl bromide to obtain methyl 4-[4-(4-methoxyphenyl)-2-oxazolyl]benzoate. The product was recrystallized from ethanol. Yield: 18%. Pale yellow prisms. Melting Point: 200 to 202° C.

EXAMPLE 4

In the same manner as in Example 1, methyl 4-carbamoylbenzoate was reacted with phenacyl bromide to obtain methyl 4-(4-phenyl-2-oxazolyl)benzoate. The product was recrystallized from ethanol. Yield: 20%. Pale yellow prisms. Melting Point: 175 to 176° C.

EXAMPLE 5

In the same manner as in Example 1, benzamide was reacted with ethyl 4-bromoacetylbenzoate to obtain ethyl 4-(2-phenyl-4-oxazolyl)benzoate. The product was recrystallized from ethanol. Yield: 29%. Pale yellow prisms. Melting Point: 110 to 112° C.

EXAMPLE 6

In the same manner as in Example 1, 4-chlorobenzamide was reacted with ethyl 4-bromoacetylbenzoate to obtain ethyl 4-[2-(4-chlorophenyl)-4-oxazolyl)benzoate. The product was recrystallized from ethanol. Yield: 49%. Pale yellow prisms. Melting Point: 153 to 154° C.

EXAMPLE 7

In the same manner as in Example 1, methyl 4-carbamoylbenzoate was reacted with 2-bromoacetyl-5-chlorothienyl to obtain methyl 4-[4-(5-chloro-2-thienyl)-2-oxazolyl]benzoate. The product was recrystallized from ethanol. Yield: 9%. Pale yellow prisms. Melting Point: 189 to 190° C.

EXAMPLE 8

A mixture of methyl 4-[4-(4-chlorophenyl)-2-oxazolyl]benzoate (450 mg), a 1N aqueous solution of sodium hydroxide (2.5 ml), tetrahydrofuran (10 ml) and methanol (5 ml) was stirred at 60 to 70° C. for 20 minutes. The reaction mixture was poured into water. To the mixture was added 1N hydrochloric acid, and precipitated 4-[4-(4-chlorophenyl)-2-oxazolyl]benzoic acid (273 mg, Yield: 64%) was collected by filtration and then washed with water. The product was recrystallized from acetone-isopropyl ether to obtain pale yellow prisms. Melting Point: 283 to 284° C. (decomposition).

EXAMPLE 9

In the same manner as in Example 8, methyl 4-[4-(4-trifluoromethylphenyl)-2-oxazolyl]benzoate was hydrolyzed to obtain 4-[4-(4-trifluoromethylphenyl)-2-oxazolyl] benzoic acid. The product was recrystallized from acetone-isopropyl ether. Yield: 68%. Pale yellow prisms. Melting Point: 258 to 259° C.

EXAMPLE 10

In the same manner as in Example 8, methyl 4-[4-(4-methoxyphenyl)-2-oxazolyl]benzoate was hydrolyzed to obtain 4-[4-(4-methoxyphenyl)-2-oxazolyl]benzoic acid. The product was recrystallized from acetone. Yield: 45%. Pale yellow prisms. Melting Point: 286 to 287° C.

EXAMPLE 11

In the same manner as in Example 8, methyl 4-(4-phenyl-2-oxazolyl)benzoate was hydrolyzed to obtain 4-(4-phenyl-2-oxazolyl]benzoic acid. The product was recrystallized from tetrahydrofuran-isopropyl ether. Yield: 60%. Pale yellow prisms. Melting Point: 275 to 276° C.

EXAMPLE 12

In the same manner as in Example 8, ethyl 4-(2-phenyl-4-oxazolyl)benzoate was hydrolyzed to obtain 4-(2-phenyl-4-oxazolyl]benzoic acid. The product was recrystallized from tetrahydrofuran. Yield: 59%. Pale yellow prisms. Melting Point,: 271 to 273° C.

EXAMPLE 13

In the same manner as in Example 8, ethyl 4-[2-(4-chlorophenyl)-4-oxazolyl]benzoate was hydrolyzed to obtain 4-[2-(4-chlorophenyl)-4-oxazolyl]benzoic acid. The product was recrystallized from acetone. Yield: 16%. Pale yellow prisms. Melting Point: 288 to 289° C.

EXAMPLE 14

In the same manner as in Example 8, methyl 4-[4-(5-chloro-2-thienyl)-2-oxazolyl]benzoate was hydrolyzed to obtain 4-[4-(5-chloro-2-thienyl)-2-oxazolyl]benzoic acid. The product was recrystallized from tetrahydrofuran-isopropyl ether. Yield: 76%. Pale yellow prisms. Melting Point: 300° C. or higher. (CDCl$_3$) δ 7.18 (1H, d, J=4 Hz), 7.40 (1H, d, J=4 Hz), 8.12 (4H, s), 8.73 (1H, s).

EXAMPLE 15

A mixture of methyl 4-carbamoylbenzoate (896 mg), 2-trifluoromethylphenacyl bromide (2.22 g) and N,N-dimethylformamide (5 ml) was stirred at 130° C. for 2 hours. Hot ethanol was added to the reaction mixture, which was poured into water, and extracted with ethyl acetate. The ethyl acetate layer was concentrated, and the residue was subjected to a silica gel column chromatography to obtain methyl 4-[4-(2-trifluoromethylphenyl)-2-oxazolyl]benzoate as an oil from a fraction eluted with ethyl acetate-hexane. This oil was dissolved in a mixture of tetrahydrofuran (10 ml) and ethanol (10 ml), and hydrolyzed by adding a 1N aqueous solution of sodium hydroxide (10 ml). The reaction mixture was neutralized with 1N hydrochloric acid, and precipitated crystals were collected by filtration. The product was recrystallized from acetone-hexane to obtain 4-[4-(2-trifluoromethylphenyl)-2-oxazolyl]benzoic acid (203 mg, yield: 12%). Colorless prisms. Melting Point: 264 to 265° C.

EXAMPLE 16

In the same manner as in Example 1, methyl 4-carbamoylbenzoate was reacted with 3-trifluoromethylphenacyl bromide to obtain methyl 4-[4-(3-trifluoromethylphenyl)-2-oxazolyl]benzoate. The product was recrystallized from ethanol. Yield: 21%. Pale yellow prisms. Melting Point: 134 to 135° C.

EXAMPLE 17

In the same manner as in Example 1, methyl 4-carbamoylbenzoate was reacted with 3,5-bis(trifluoromethyl)phenacyl bromide to obtain methyl 4-[4-[3,5-bis(trifluoromethyl)phenyl]-2-oxazolyl]benzoate. The product was. recrystallized from ethanol., Yield: 24%. Pale yellow prisms. Melting Point: 180 to 181° C.

EXAMPLE 18

In the same manner as in Example 1, methyl 4-carbamoylbenzoate was reacted with 4-difluoromethoxyphenacyl bromide to obtain methyl 4-[4-(4-difluoromethoxylphenyl)-2-oxazolyl]benzoate. The product was recrystallized from ethanol. Yield: 21%. Pale yellow prisms. Melting Point: 160 to 161° C.

EXAMPLE 19

In the same manner as in Example 1, 4-trifluoromethylbenzamide was reacted with ethyl 4-bromoacetylbenzoate to obtain ethyl 4-[2-(4-trifluoromethylphenyl)-4-oxazolyl]benzoate. The product was recrystallized from ethanol. Yield: 21%. Pale yellow prisms. Melting Point: 168 to 170° C.

EXAMPLE 20

In the same manner as in Example 1, 3-trifluoromethylbenzamide was reacted with ethyl 4-bromoacetylbenzoate to obtain ethyl 4-[2-(3-trifluoromethylphenyl)-4-oxazolyl]benzoate. The product was recrystallized from ethanol. Yield: 22%. Pale yellow prisms. Melting Point: 132 to 133° C.

EXAMPLE 21

In the same manner as in Example 1, methyl 3-carbamoylbenzoate was reacted with 4-trifluoromethylphenacyl bromide to obtain methyl 3-[4-(4-trifluoromethylphenyl)-2-oxazolyl]benzoate. The product was recrystallized from ethanol. Yield: 30%. Pale yellow prisms. Melting Point: 151 to 152° C.

EXAMPLE 22

In the same manner as in Example 8, methyl 4-[4-(3-trifluoromethylphenyl)-2-oxazolyl]benzoate was hydrolyzed to obtain 4-[4-(3-trifluoromethylphenyl)-2-oxazolyl]benzoic acid. The product was recrystallized from acetone-hexane. Yield: 59%. Pale yellow prisms. Melting Point: 253 to 254° C.

EXAMPLE 23

In the same manner as in Example 8, methyl 4-[4-[3,5-bis(trifluoromethyl)phenyl]-2-oxazolyl]benzoate was hydrolyzed to obtain 4-[4-[3,5-bis(trifluoromethyl)phenyl]-2-oxazolyl]benzoic acid. The product was recrystallized from acetone-hexane. Yield: 71%. Pale yellow prisms. Melting Point: 277 to 279° C.

EXAMPLE 24

In the same manner as in Example 8, methyl 4-[4-(4-difluoromethoxylphenyl)-2-oxazolyl]benzoate was hydrolyzed to obtain 4-[4-(4-difluoromethoxylphenyl)-2-oxazolyl]benzoic acid. The product was recrystallized from acetone-hexane. Yield: 73%. Pale yellow prisms. Melting Point: 261 to 262° C.

EXAMPLE 25

In the same manner as in Example 8, ethyl 4-[2-(4-trifluoromethylphenyl)-4-oxazolyl]benzoate was hydrolyzed to obtain 4-[2-(4-trifluoro methylphenyl)-4-oxazolyl]benzoic acid. The product was recrystallized from acetone-hexane. Yield: 73%. Pale yellow prisms. Melting Point: 294 to 295° C.

EXAMPLE 26

In the same manner as in Example 8, ethyl 4-[2-(3-trifluoromethylphenyl)-4-oxazolyl]benzoate was hydrolyzed to obtain 4-[2-(3-trifluoromethylphenyl)-4-oxazolyl]benzoic acid. The product was recrystallized from acetone hexane. Yield: 70%. Pale yellow prisms. Melting Point: 268 to 269° C.

EXAMPLE 27

In the same manner as in Example 8, methyl 3-[4-(4-trifluoromethylphenyl)-2-oxazolyl]benzoate was hydrolyzed to obtain 3-[4-(4-trifluoromethylphenyl)-2-oxazolyl]benzoic acid. The product was recrystallized from acetone-hexane. Yield: 65%. Colorless prisms. Melting Point: 206 to 208° C.

EXAMPLE 28

A mixture of methyl 4-thiocarbamoylbenzoate (1.56 g), 4-difluoromethoxyphenacyl bromide (2.65 g) and ethanol (15 ml) was stirred at 80 to 90° C. for 1 hour. The reaction mixture was cooled, and precipitated crystals were collected by filtration to obtain methyl 4-[4-(4-difluoromethoxyphenyl)-2-thiazolyl]benzoate (2.00 g, yield: 69%). The product was recrystallized from ethanol to obtain pale yellow prisms. Melting Point: 146 to 148° C.

EXAMPLE 29

In the same manner as in Example 28, methyl 4- thiocarbamoylbenzoate was reacted with 4-chlorophenylacyl bromide to obtain methyl 4-[4-(4-chlorophenyl)-2-thiazolyl]benzoate. The product was recrystallized from ethanol. Yield: 70%. Pale yellow prisms. Melting point: 186 to 187° C.

EXAMPLE 30

In the same manner as in Example 28, methyl 4-thiocarbamoylbenzoate was reacted with 2-bromoacethyl-5-chlorothiphene to obtain methyl 4-[4-(5-chloro-2-thienyl)-2-thiazolyl]benzoate. The product was recrystallized from ethanol. Yield: 71%. Pale yellow prisms. Melting point: 171 to 172° C.

EXAMPLE 31

In the same manner as in Example 28, thionicotinamide was reacted with ethyl 4-bromoacetylbenzoate to obtain ethyl 4-[2-(3-pyridyl)-4-thiazolyl]benzoate hydrobromide. The product was recrystallized from ethanol. Yield: 67%. Pale yellow prisms. Melting point: 234 to 236° C.

EXAMPLE 32

In the same manner as in Example 28, methyl 4-thiocarbamoylbenzoate was reacted with 4-trifluoromethylphenacyl bromide to obtain methyl 4-[4-(4-trifluoromethylphenyl)-2-thiazolyl]benzoate. The product was recrystallized from ethanol. Yield: 61%. Colorless prisms. Melting point: 156 to 158° C.

EXAMPLE 33

In the same manner as in Example 28, methyl 4-thiocarbamoylbenzoate was reacted with 4-methylphenacyl bromide to obtain methyl 4-[4-(4-methylphenyl)-2-thiazolyl]benzoate. The product was recrystallized from ethanol. Yield: 61%. Pale yellow prisms. Melting point: 185 to 187° C.

EXAMPLE 34

In the same manner as in Example 28, methyl 4-thiocarbamoylbenzoate was reacted with 3-bromoacetylpyridine hydrobromide to obtain methyl 4-[4-(3-pyridyl)-2-thiazolyl]benzoate hydrobromide. The product was recrystallized from ethanol. Yield: 80%. Pale yellow prisms. Melting point: 241 to 242° C.

EXAMPLE 35

In the same manner as in Example 28, methyl 4-thiocarbamoylbenzoate was reacted with 4-bromoacetylpyridine hydrobromide to obtain methyl 4-[4-(4-pyridyl)-2-thiazolyl]benzoate hydrobromide. The product was recrystallized from ethanol. Yield: 66%. Pale yellow prisms. Melting point: 238 to 240° C.

EXAMPLE 36

In the same manner as in Example 28, thioisonicotinamide was reacted with ethyl 4-bromoacetylbenzoate to obtain ethyl 4-[2-(4-pyridyl)-4-thiazolyl]benzoate hydrobromide. The product was recrystallized from ethanol. Yield: 67%. Pale yellow prisms. Melting point: 248 to 250° C.

EXAMPLE 37

A mixture of methyl 4-thiocarbamoylbenzoate (1.00 g), 2-trifluoromethyphenacyl bromide (1.50 g) and N,N-dimethylformamide (3 ml) was stirred at 120 to 130° C. for 3 hours. The reaction mixture was poured into water, and precipitated crystals were collected by filtration and then subjected to a silica gel column chromatography. From a fraction eluted with ethyl acetate-hexane (1:4, v/v), methyl 4-[4-(2-trifluoromethylphenyl)-2-thiazolyl]benzoate (1.01 g, yield: 54%) was obtained. The product was recrystallized from hexane-toluene to obtain colorless prisms. Melting point: 122 to 123° C.

EXAMPLE 38

In the same manner as in Example 28, methyl 4-thiocarbamoylbenzoate was reacted with 2-bromoacetylpyridine hydrobromide to obtain methyl 4-[4-(2-pyridyl)-2-thiazolyl]benzoate hydrobromide. The product was recrystallized from ethanol. Yield: 80%. Pale yellow prisms. Melting point: 243 to 244° C.

EXAMPLE 39

In the same manner as in Example 28, 4-chlorobenzamide was reacted with ethyl 5-bromoacethyl-2-thienylcarboxylate to obtain ethyl 5-[2-(4-chlorophenyl)-4-thiazolyl]-2-thienylcarboxylate. The product was recrystallized from ethanol. Yield: 51%. Pale yellow prisms. Melting point: 234 to 236° C.

EXAMPLE 40

In the same manner as in Example 28, methyl 4'-thiocarbamoylbenzoate was reacted with 3-trifluoromethoxyphenacyl bromide to obtain methyl 4-[4-(3-trifluoromethoxyphenyl)-2-thiazolyl]benzoate. The product was recrystallized from ethanol. Yield: 49%. Pale yellow prisms. Melting point: 132 to 134° C.

EXAMPLE 41

In the same manner as in Example 28, methyl 4-thiocarbamoylbenzoate was reacted with 4-trifluoromethoxyphenacyl bromide to obtain methyl 4-[4-(4-trifluoromethoxyphenyl)-2-thiazolyl]benzoate. The product was recrystallized from ethanol. Yield: 60%. Pale yellow prisms. Melting point: 138 to 139° C.

EXAMPLE 42

In the same manner as in Example 28, methyl 4-thiocarbamoylbenzoate was reacted with 2,3,4,5,6-pentafluorophenacyl bromide to obtain methyl 4-[4-(2,3,4,5,6-pentafluorophenyl)-2-thiazolyl]benzoate. The product was recrystallized from ethanol. Yield: 60%. Pale yellow prisms. Melting point: 141 to 142° C.

EXAMPLE 43

In the same manner as in Example 28, methyl 4-thiocarbamoylbenzoate was reacted with 3-chlorophenacyl bromide to obtain methyl 4-[4-(3-chlorophenyl)-2-thiazolyl]benzoate. The product was recrystallized from ethanol. Yield: 72%. Pale yellow prisms. Melting point: 150 to 151° C.

EXAMPLE 44

In the same manner as in Example 28, methyl 3-thiocarbamoylbenzoate was reacted with 4-trifluoromethylphenacyl bromide to obtain methyl 3-[4-(4-trifluoromethylphenyl)-2-thiazolyl]benzoate. The product was recrystallized from ethanol. Yield: 74%. Colorless prisms. Melting point: 142 to 143° C.

EXAMPLE 45

In the same manner as in Example 28, methyl 3-thiocarbamoylbenzoate was reacted with 3-trifluoromethylphenacyl bromide to obtain methyl 3-[4-(3-trifluoromethylphenyl)-2-thiazolyl]benzoate. The product was recrystallized from ethanol. Yield: 72%. Colorless prisms. Melting point: 105 to 106° C.

EXAMPLE 46

In the same manner as in Example 28, methyl 3-thiocarbamoylbenzoate was reacted with 2,4-difluorophenacyl bromide to obtain methyl 3-[4-(2,4-difluorophenyl)-2-thiazolyl]benzoate. The product was recrystallized from ethanol. Yield: 69%. Pale yellow prisms. Melting point: 121 to 122° C.

EXAMPLE 47

In the same manner as in Example 28, methyl 3-thiocarbamoylbenzoate was reacted with 4-methoxyphenacyl bromide to obtain methyl 3-[4-(4-methoxyphenyl)-2-thiazolyl]benzoate. The product was recrystallized from ethanol. Yield: 74%. Pale yellow prisms. Melting point: 108 to 109° C.

EXAMPLE 48

In the same manner as in Example 28, methyl 3-thiocarbamoylbenzoate was reacted with 3,4-difluorophenacyl bromide to obtain-methyl 3-[4-(3,4-difluorophenyl)-2-thiazolyl]benzoate. The product was recrystallized from ethanol. Yield: 70%. Colorless prisms. Melting point: 147 to 148° C.

EXAMPLE 49

In the same manner as in Example 28, ethyl 3-thiocarbamoylbenzoate was reacted with 3-bromoacetyl-2,5-dimethylfuran to obtain ethyl 3-[4-(2,5-dimethyl-3-furyl)-2-thiazolyl]benzoate. The product was recrystallized from ethanol. Yield: 16%, Pale yellow prisms. Melting point: 100 to 101° C.

EXAMPLE 50

In the same manner as in Example 28, methyl 3-thiocarbamoylbenzoate was reacted with 3-trifluoromethoxyphenacyl bromide to obtain methyl 3-[4-(3-trifluoromethoxyphenyl)-2-thiazolyl]benzoate. The product was recrystallized from ethanol. Yield: 34%. Colorless prisms. Melting point: 84 to 85° C.

EXAMPLE 51

A mixture of methyl 4-[4-(4-difluoromethoxyphenyl)-2-thiazolyl]benzoate (1.00 g), a 1N aqueous solution of sodium hydroxide (6 ml), tetrahydrofuran (10 ml) and methanol (10 ml) was stirred at 60. to 70° C. for 1 hour. The mixture was poured into water and 1N hydrochloric acid was added. Precipitated 4-[4-(4-difluoromehtoxyphenyl)-2-thiazolyl]benzoic acid was collected by filtration, and washed with water. The product was recrystallized from acetone-hexane to obtain pale yellow prisms (610 mg, yield: 64%). Melting point: 252 to 253° C.

EXAMPLE 52

In the same manner as in Example 51, methyl 4-[4-(4-chlorophenyl)-2-thiazolyl]benzoate was hydrolyzed to obtain 4-[4-(4-chlorophenyl)-2-thiazolyl]benzoic acid. The product-was recrystallized from tetrahydrofuran-ethanol. Yield: 66%. Pale yellow prisms. Melting point: 284 to 285° C.

EXAMPLE 53

In the same manner as in Example 51, methyl 4-[4-(5-chloro-2-thienyl)-2-thiazolyl]benzoate was hydrolyzed to obtain 4-[4-(5-chloro-2-thienyl)-2-thiazolyl]benzoic acid. The product was recrystallized from tetrahydrofuran-isopropyl ether. Yield: 63%. Pale yellow prisms. Melting point: 283 to 284° C.

EXAMPLE 54

In the same manner as in Example 51, ethyl 4-[2-(3-pyridyl)-4-thiazolyl]benzoate hydrobromide was hydrolyzed to obtain 4-[2-(3-pyridyl)-4-thiazolyl]benzoic acid. The product was recrystallized from tetrahydrofuran-isopropyl ether. Yield: 81%. Pale yellow prisms. Melting point: >300° C. NMR (DMSO-$d_6$) δ 7.59 (1H, dd, J=8,5 Hz), 8.06 (2H, d, J=8.5 Hz), 8.21 (2H, d, J=8.5 Hz), 8.4–8.5 (1H, m), 8.47 (1H, s), 8.72 (1H, dd, J=5.2 Hz), 9.24 (1H, d, J=2 Hz).

EXAMPLE 55

In the same manner as in Example 51, methyl 4-[4-(4-trifluoromethylphenyl)-2-thiazolyl]benzoate was hydrolyzed to obtain 4-[4-(4-trifluoromethylphenyl)-2-thiazolyl]benzoic acid. The product was recrystallized from acetone-hexane. Yield: 81%. Colorless prisms. Melting point: 164 to 165° C.

EXAMPLE 56

In the same manner as in Example 51, methyl 4-[4-(4-methylphenyl)-2-thiazolyl]benzoate was hydrolyzed to obtain 4-[4-(4-methylphenyl)-2-thiazolyl]benzoic acid. The product was recrystallized from tetrahydrofuran-hexane. Yield: 83%. Colorless prisms. Melting point: 289 to 290° C.

EXAMPLE 57

In the same manner as in Example 51, methyl 4-[4-(3-pyridyl)-2-thiazolyl]benzoate hydrobromide was hydrolyzed to obtain 4-[4-(3-pyridyl)-2-thiazolyl]benzoic acid. The product was recrystallized from tetrahydrofuran-hexane. Yield: 65%. Pale yellow prisms. Melting point: 303 to 304° C.

EXAMPLE 58

In the same manner as in Example 51, methyl 4-[4-(4-pyridyl)-2-thiazolyl]benzoate hydrobromide was hydrolyzed to obtain 4-[4-(4-pyridyl)-2-thiazolyl]benzoic acid. The product was recrystallized from N,N-dimethylformamide-water. Yield: 12%. Pale yellow prisms. Melting point: >300° C. NMR (DMSO-$d_6$) δ 8.02 (2H, d, J=5.5 Hz, 8.10 (2H, d, J=8.5 Hz), 8.18 (2H, d, J=8.5 Hz), 8.61 (1H, s), 8.69 (2H, d, J=5.5 Hz).

EXAMPLE 59

In the same manner as in Example 51, ethyl 4-[2-(4-pyridyl)-4-thiazolyl]benzoate hydrobromide was hydrolyzed to obtain 4-[2-(4-pyridyl)-4-thiazolyl]benzoic acid. The product was recrystallized from N,N-dimethylformamide-water. Yield: 51%. Pale yellow prisms. Melting point: >300° C. NMR (DMSO-$d_6$) δ 7.95–8.15 (4H, m), 8.15–8.30 (2H, m), 8.54 (1H, s), 8.7–8.9 (2H, m).

EXAMPLE 60

In the same manner as in Example 51, methyl 4-[4-(2-trifluoromethylphenyl)-2-thiazolyl]benzoate was hydrolyzed to obtain 4-[4-(2-trifluoromethylphenyl)-2-thiazolyl]benzoic acid. The product was recrystallized from acetone-hexane. Yield: 68%. Colorless prisms. Melting point: 225 to 227° C.

EXAMPLE 61

In the same manner as in Example 51, methyl 4-[4-(2-pyridyl)-2-thiazolyl]benzoate hydrobromide was hydrolyzed to obtain 4-[4-(2-pyridyl)-2-thiazolyl]benzoic acid. The product was recrystallized from tetrahydrofuran-isopropyl ether. Yield: 67%. Pale yellow prisms. Melting point: >300° C. NMR (DMSO-d$_6$) δ 7.35–7.45 (1H, m), 7.9–8.05 (1H, m), 8.10 (2H, d, J=8.5 Hz), 8.19 (2H, d, J=8.5 Hz), 8.43 (1H, s), 8.67 (1H, d, J=4.5 Hz).

EXAMPLE 62

In the same manner as in Example 51, ethyl 5-[2-(4-chloropheny)-4-thiazoyl]-2-thienylcarboxlate was hydrolyzed to obtain 5-[2-(4-chlorophenyl)-4-thiazoyl]-2-thienyl carboxylic acid. The Product was recrystallizied from tetrahydrofuran-hexane. Yield: 74%. Pale yellow prisms. Melting point: 273 to 274° C.

EXAMPLE 63

In the same manner as in Example 51, methyl 4-[4-(3-trifluoromethoxylphenyl)-2-thiazolyl]benzoate was hydrolyzed to obtain 4-[4-(3-trifluoromethoxylphenyl)-2-thiazolyl]benzoic acid. The product was recrystallized from acetone-hexane. Yield: 57%. Colorless prisms. Melting point: 233 to 234° C.

EXAMPLE 64

In the same manner as in Example 51, methyl 4-[4-(4-trifluoromethoxylphenyl)-2-thiazolyl]benzoate was hydrolyzed to obtain 4-[4-(4-trifluoromethoxylphenyl)-2-thiazolyl]benzoic acid. The product was recrystallized from acetone-hexane. Yield: 70%. Pale yellow prisms. Melting point: 245 to 246° C.

EXAMPLE 65

In the same manner as in Example 51, methyl 4-[4-(2,3,4,5,6-pentafluorophenyl)-2-thiazolyl]benzoate was hydrolyzed to obtain 4-[4-(2,3,4,5,6-pentafluorophenyl)-2-thiazolyl]benzoic acid. The product was recrystallized from acetone-hexane. Yield: 70%. Colorless prisms. Melting point: 273 to 274° C.

EXAMPLE 66

In the same manner as in Example 51, methyl 4-[4-(3-chlorophenyl)-2-thiazolyl]benzoate was hydrolyzed to obtain 4-[4-(3chlorophenyl)-2-thiazolyl]benzoic acid. The product was recrystallized from tetrahydrofurean-isopropyl ether. Yield: 75%. Colorless psims. Melting point: 2518 to 259° C.

EXAMPLE 67

In the same manner as in Example 51, methyl 3-[4-(4-trifluoromethylphenyl)-2-thiazolyl]benzoate was hydrolyzed to obtain 3-[4-(4-trifluoromethylphenyl)-2-thiazolyl] benzoic acid. The product was recrystallized from acetone-hexane. Yield: 62%. Colorless prisms. Melting point: 230 to 231° C.

EXAMPLE 68

In the same manner as in Example 51, methyl 3-[4-(3trifluoromethylphenyl)-2-thiazolyl]benzoate was hydrolyzed to obtain 3-[4-(3-trifluoromethylphenyl)-2-thiazolyl] benzoic acid. The product was recrystallized from acetone-hexane. Yield: 84%. Colorless prisms. Melting point: 229 to 230° C.

EXAMPLE 69

In the same manner.as in Example 51, methyl 3-[4-(2,4-difluorophenyl)-2-thiazolyl]benzoate was hydrolyzed to obtain 3-[4-(2,4-difluorophenyl)-2-thiazolyl]benzoic acid. The product was recrystallized from acetone-hexane. Yield: 74%. Colorless prisms. Melting point: 255 to 256° C.

EXAMPLE 70

In the same manner as in Example 51, methyl 3-[4-(4-methoxyphenyl)-2-thiazolyl]benzoate was hydrolyzed to obtain 3-[4-(4-methoxyphenyl)-2-thiazolyl]benzoic acid. The product was recrystallized from acetone-hexanes. Yield: 82%. Colorless prisms. Melting point: 236to 238° C.

EXAMPLE 71

In the same manner as in Example 51, methyl 3-[4-(3,4-difluorophenyl)-2-thiazolyl]benzoate was hydrolyzed to obtain 3-[4-(3,4-difluorophenyl)-2-thiazolyl]benzoic acid. The product was recrystallized from acetone-hexane. Yield: 82%. Colorless prisms. Melting point: 255 to 256° C.

EXAMPLE 72

In the same manner as in Example 51, ethyl 3-[4-(2,5-dimethyl-3-furyl)-2-thiazolyl]benzoate was hydrolyzed to obtain 3-[4-(2,5-dimethyl-3-furyl)-2-thiazolyl]benzoic acid. The product was recrystallized from acetone-hexane. Yield: 59%. Pale yellow prisms. Melting point: 174 to 175° C.

EXAMPLE 73

In the same manner as in Example 51, methyl 3-[4-(3-trifluoromethoxylphenyl)-2-thiazolyl]benzoate was hydrolyzed to obtain 3-[4-(3-trifluoromethoxylphenyl)-2-thiazolty]benzoic acid. The product was recrystallized from acetone-hexane. Yield: 73%. Colorless prisms. Melting point: 182 to 183° C.

EXAMPLE 74

A mixture of ethyl 3-thiocarbamoylbenzoate (2.09 g), 3,4-dimethylpenacyl bromide (2.67 g) and ethanol (15 ml) was stirred at 80 to 90° C. for 1 hour. The reaction mixture was cooled, and precipitated crystals were collected by filtratin to obtain ethyl 3-[4-(3,4-dimethylphenyl)-2-thiazolyl]benzoate (2.25 g, yield: 67%. The product was recrystallized from ethanol to obtain colorless prisms. Melting point: 114 to 115° C.

EXAMPLE 75

In the same manner as in Example 74, methyl 4-thiocarbamoylbenzoate was reacted with 4-bromophenacyl bromide to obtain methyl 4-[4-(4-bromophenyl)-2-thiazolyl]benzoate. The product was recrystallized from ethanol. Yield: 73%. Colorless prisms. Melting point: 206 to 207° C.

EXAMPLE 76

In the same manner as in Example 74, methyl 4-thiocarbamoylbenzoate was reacted with 3,4-dimethylphenacyl bromide to obtain ethyl 3-[4-(3,4-dimethylphenyl)-2-thiazolyl]-benzoate. The product was recrystallized from ethanol. Yield: 83%. Colorless prisms. Melting point: 147 to 148° C.

EXAMPLE 77

In the same manner as in Example 74, methyl 4-thiocarbamoylbenzoate was reacted with 3-bromoacetyl-2,5-dimethylfuran to obtain methyl 4-[4-(2,5-dimethyl-3- furyl)-2-thiazolyl]benzoate. The product was recrystallized from ethanol. Yield: 36%. Pale yellow prisms. Melting point: 103 to 105° C.

EXAMPLE 78

In the same manner as in Example 74, ethyl 3-thiocarbamoylbenzocate was reacted with 3-bromoacetyl-2,5-dimethylthy to obtain ethyl 3-[4-(2,5-dimethyl-3-thienyl)-2-thiazolyl]benzoate. The product was recrystallized from ethanol. Yield: 61%. Pale yellow prisms. Melting point: 115 to 116° C.

EXAMPLE 79

In the same manner as in Example 74, methyl 4-thiocarbamoylbenzoate was reacted with 3-bromoacetyl-2,5-dimethylthiophene to obtain methyl 4-[4-(2,5-dimethyl-3-thienyl)-2-thiazolyl]benzoate. The product was recrystallized from ethanol. Yield: 64%. Pale yellow pritsms. Melting point: 109 to 110° C.

EXAMPLE 80

In the same manner as in Example 74, methyl 4-thiocarbamoylbenzoate was reacted with 3-bromoacetyl-2,5-dichlorothiophene to obtain methyl 4-[4-(2,5-dichloro-3-thienyl)-2-thiazolyl]benzoate. The product was recrystallized from ethanol. Yield: 74%. Pale yellow prisms. Melting point: 149 to 150° C.

EXAMPLE 81

In the same manner as in Example 74, ethyl 3-thiocarbamoylbenzoate was reacted with 3-bromoacetyl-2,5-dichlorolhiophene to obtain ethyl 3-[4-(2,5-dichloro-3-thienyl)-2-thiazolyl]benzoate. The product was recrystallized from ethanol. Yield: 83%. Pale yellow prisms. Melting point: 125 to 126° C.

EXAMPLE 82

In the same manner as in Example 74, ethyl 3-thiocarbamoylbenzoate was reacted with 4-ethoxyphenacyl bromide to obtain ethyl 3-[4-(4-ethoxyphenyl)-2-thiazolyl]benzoate. The product was recrystallized from ethanol. Yield: 59%. Pale yellow prisms. Melting point: 108 to 110° C.

EXAMPLE 83

In the same manner as in Example 74, methyl 4-thiocarbamoylbenzoate was reacted with 4-ethoxyphenacyl bromide to obtain methyl 3-[4-(4-ethoxyphenyl)-2-thiazolyl]benzoate. The product was recrystallized from ethanol. Yield: 80%. Pale yellow prisms. Melting point: 192 to 193° C.

EXAMPLE 84

In the same manner as in Example 74, ethyl 3-thiocarbamoylbenzoate was reacted with 4-t-butylphenacyl bromide to obtain ethyl 3-[4-(4-t-butylphenyl)-2-thiazolyl]benzoate. The product was recrystallized from ethanol. Yield: 37%. Pale yellow prisms. Melting point: 96 to 97° C.

EXAMPLE 85

In the same manner as in Example 74, methyl 4-thiocarbamoylbenzoate was reacted with 4-t-butylphenacyl bromide to obtain methyl 4-[4-(4-t-butylphenyl)-2-thiazolyl]benzoate. The product was recrystallized from ethanol. Yield: 68%. Pale yellow prisms. Melting point: 154 to 155° C.

EXAMPLE 86

In the same manner as in Example 74, ethyl 3-thiocarbamoylbenzoate was reacted with 4-isopropylphenacyl bromide to obtain ethyl 3-[4-(4-isopropylphenyl)-2-thiazolyl]benzoate. The product was recrystallized from ethanol. Yield: 46%. Pale yellow prisms. Melting point: 91 to 92° C.

EXAMPLE 87

In the same manner as in Example 74, methyl 4-thiocearbamoylbenzoate was reacted with 4-isopropylphenacyl bromide to obtain methyl 4-[4-(4-isopropylphenyl)-2-thiazolyl]benzoate. The product was recrystallized from ethanol. Yield: 50%. Pale yellow prisms. Melting point: 134 to 135° C.

EXAMPLE 88

A mixture of ethyl 3-[4-(3,4-dimethylphenyl)-2-thiazolyl]benzoate (1.25 g), a 1N aqueous solution of sodium hydroxide (10 ml), tetrahydrofuran (10 ml) and ethanol (10 ml) was stirred at 60 to 70° C. for 1 hour. The reaction mixture was poured into 1N hydrochloric acid, and precipitated crystals were collected by filtration, and then washed with water. The product was recrystallized from acetone-hexane to obtain 3-[4-(3,4-dimethylphenyl)-2-thiazolyl]benzoic acid (825 mg, yield: 72%). Colorless prisms. Melting point: 235 to 236° C.

EXAMPLE 89

In the same manner as in Example 88, methyl 4-[4-(4-bromophenyl)-2-thiazolyl]benzoate was hydrolyzed to obtain 4-[4-(4-bromophenyl)-2-thiazolyl]benzoic acid. The product was recrystallized from tetrahydrofuran-hexane. Yield: 51%:. Colorless prisms. Melting point: >300° C. NMR (DMSO-$d_6$) δ:7.67 (2H, d, J=9 Hz), 8.0–8.2 (6H, m), 8.32 (1H, s).

EXAMPLE 90

In the same manner as in Example 88, methyl 4-[4-(3,4-dimethylphenyl)-2-thiazolyl]benzoate was hydrolyzed to obtain 4-[4-(3,4-dimethylphenyl)-2-thiazolyl]benzoic acid. The product was recrystallized from acetone-hexane. Yield: 83%. Pale yellow prisms. Melting point: 261 to 262° C.

EXAMPLE 91

In the same manner as in Example 88, methyl 4-[4-(2,5-dimethyl-3-furyl)-2-thiazolyl]benzoate was hydrolyzed to obtain 4-[4-(2,5-dimethyl-3-furyl)-2-thiazolyl]benzoic acid. The product was recrystallized from tetrahydrofuran-hexane. Yield: 63%. Pale yellow prisms. Melting point: 264 to 265° C.

EXAMPLE 92

In the same manner as in Example 88, ethyl 3-[4-(2,5-dimethyl-3-thienyl)-2-thiazolyl]benzoate was hydrolyzed to obtain 3-[4-(2,5-dimethyl-3-thienyl)-2-thiazolyl]benzoic acid. The product was recrystallized from acetone-hexane. Yield: 54%. Pale yellow prisms. Melting point: 155 to 156° C.

EXAMPLE 93

In the same manner as in Example 88, methyl 4-[4-(2,5-dimethyl-3-thienyl)-2-thiazolyl]benzoate was hydrolyzed to obtain 4-[4-(2,5-dimethyl-3-thienyl)-2-thiazolyl]benzoic acid. The product was recrystallized from acetone-hexane. Yield: 56%. Pale yellow prisms. Melting point: 239 to 240° C.

EXAMPLE 94

In the same manner as in Example 88, methyl 4-[4-(2,5-dichloro-3-thienyl)-2-thiazolyl]benzoate was hydrolyzed to obtain 4-[4-(2,5-dichloro-3-thienyl)-2-thiazolyl]benzoic acid. The product was recrystallized from tetrahydrofuran-hexane. Yield: 86%. Pale yellow prisms. Melting point: 266 to 267° C.

EXAMPLE 95

In the same manner as in Example 88, ethyl 3-[4-(2,5-dichloro-3-thienyl)-2-thiazolyl]benzoate was hydrolyzed to obtain 3-[4-(2,5-dichloro-3-thienyl)-2-thiazolyl]benzoic acid. The product was recrystallized from acetone-hexane. Yield: 60%. Pale yellow prisms. Melting point: 241 to 242° C.

EXAMPLE 96

In the same manner as in Example 88, ethyl 3-[4-(4-ethoxyphenyl)-2-thiazolyl]benzoate was hydrolyzed to obtain 3-[4-(4-ethoxyphenyl)-2-thiazolyl]benzoic acid. The product was recrystallized from acetone-hexane. Yield: 79%. Pale yellow prisms. Melting point: 231 to 232° C.

EXAMPLE 97

In the same manner as in Example 88, methyl 3-[4-(4-ethoxyphenyl)-2-thiazolyl]benzoate was hydrolyzed to obtain 3-[4-(4-ethoxyphenyl)-2-thiazolyl]benzoic acid. The product was recrystallized from tetrahydrofuran-hexane. Yield: 69%. Pale yellow prisms. Melting point: 280 to 281° C.

EXAMPLE 98

In the same manner as in Example 88, ethyl 3-[4-(4-t-butylphenyl)-2-thiazolyl]benzoate was hydrolyzed to obtain 3-[4-(4-t-butylphenyl)-2-thiazolyl]benzoic acid. The product was recrystallized from acetone-hexane. Yield: 36%. Pale yellow prisms. Melting point: 250 to 251° C.

EXAMPLE 99

In the same manner as in Example 88, methyl 4-[4-(4-t-butylphenyl)-2-thiazolyl]benzoate was hydrolyzed to obtain 4-[4-(4-butylphenyl)-2-thiazolyl]benzoic acid. The product was recrystallized from tetrahydrofuran-hexane. Yield: 70%. Pale yellow prisms. Melting point: 263 to 265° C.

EXAMPLE 100

In the same manner as in Example 88, ethyl 3-[4-(4-isopropylphenyl)-2-thiazolyl]benzoate was hydrolyzed to obtain 3-[4-(4-isopropylphenyl)-2-thiazolyl]benzoic acid. The product was recrystallized from ethyl acetate-hexane. Yield: 64%. Pale yellow prisms. Melting point: 214 to 215° C.

EXAMPLE 101

In the same manner as in Example 88, methyl 4-[4-(4-isopropylphenyl)-2-thiazolyl]benzoate was hydrolyzed to obtain 4-[4-(4-isopropylphenyl)-2-thiazolyl]benzoic acid. The product was recrystallized from tetrahydrofuran-hexane. Yield: 50%. Pale yellow prisms. Melting point: 257 to 258° C.

EXAMPLE 102

In the same manner as in Example 74, thiobenzamide was reacted with ethyl 4-bromoacetylbenzoate to obtain ethyl 4-(2-phenyl-4-thiazolyl]benzoate. The product was recrystallized from ethanol. Yield: 68%. Pale yellow prisms. Melting point: 72 to 73° C.

EXAMPLE 103

In the same manner as in Example 74, 4-chlorothiobenzamide was reacted with ethyl 4-bromoacetylbenzoate to obtain ethyl 4-[2-(4-chlorophenyl)-4-thiazolyl)benzoate. The product was recrystallized from ethanol. Yield: 47%. Pale yellow prisms. Melting point: 105 to 106° C.

EXAMPLE 104

In the same manner as in Example 74, 4-trifluoromethylthiobenzamide was reacted with ethyl 4-bromoacetylbenzoate to obtain ethyl 4-[2-(4-trifluoromethylphenyl)-4-thiazolyl)benzoate. The product was recrystallized from ethanol. Yield: 56%. Pale yellow prisms. Melting point: 163 to 164° C.

EXAMPLE 105

In the same manner as in Example 74, thioisonicotinamide was reacted with ethyl 4-bromoacetylbenzoate to obtain ethyl 4-[2-(4-pyridyl)-4-thiazolyl)benzoate hydrobromide. The product was, recrystallized from ethanol. Yield: 67%. Pale Yellow prisms. Melting point: 247 to 248° C.

EXAMPLE 106

A mixture of ethyl 4-[2-(4-chlorobenzoylamino)-1-oxoethyl]benzoate (1.04 g), phosphorus oxychloride (0.92 g) and toluene (10 ml) was refluxed under heating for 1 hour. The reaction mixture was poured into water, and precipitated crystals of ethyl 4-[2-(4-chlorophenyl)-5-oxazolyl]benzoate (560 mg, yield: 57%) were collected by filtration. The product was recrystallized from ethyl acetate-hexane to obtain pale yellow prisms. Melting point: 137 to 138° C.

EXAMPLE 107

In the same manner as in Example 106, ethyl 4-[2-(4-trifluoromethylbenzoylamino)-1-oxoethyl]benzoate was reacted with phosphorus oxychloride to obtain ethyl 4-[2-(4-trifluoromethylphenyl)-5-oxazolyl]benzoate. The product was recrystallized from ethanol. Yield: 60%. Pale yellow prisms. Melting point: 142 to 143° C.

EXAMPLE 108

In the same manner as in Example 106, ethyl 4-[N-(4-chlorobenzoylmethyl)carbamoyl]benzoate was reacted with phosphorus oxychloride to obtain ethyl 4-[5-(4-chlorophenyl)-2-oxazolyl]benzoate. The product was recrystallized from ethyl acetate-isopropyl ether. Yield: 80%. Pale yellow prisms. Melting point: 195 to 197° C.

EXAMPLE 109

A mixture of ethyl 4-[2-(4-chlorophenyl)-5-oxazolyl]benzoate (500 mg), a 1N aqueous solution of sodium hydroxide (5 ml), tetrahydrofuran (5 ml) and ethanol (5 ml) was stirred at 60 to 70° C. for 1 hour. The reaction mixture was poured into 1N hydrochloric acid, and precipitated crystals of 4-[2-(4-chlorophenyl)-5-oxazolyl]benzoic,acid (320 mg, yield: 70%). were collected by filtration. The product was recrystallized from tetrahydrofuran-hexane to obtain pale yellow prisms. Melting point: 292 to 293° C.

EXAMPLE 110

In the same manner as in Example 109, ethyl 4-[2-(4-trifluoromethylphenyl)-5-oxazolyl]benzoate was hydrolyzed to obtain 4-[2-(4-trifluoromethylphenyl)-5-oxazolyl]benzoic acid. The product was recrystallized from acetone-isopropyl ether. Yield: 68%. Pale yellow prisms. Melting point: 253 to 254° C.

EXAMPLE 111

A mixture of ethyl 4-[2-(4-trifluoromethylbenzoylamino)-1-oxoethyl]benzoate (900 mg), Lawesson's reagent (960 mg) and xylene (5 ml) was stirred at 140 t 145° C. for 2 hours. The reaction mixture was cooled, and precipitated crystals of ethyl 4-[2-(4-trifluoromethylphenyl)-5-thiazolyl]benzoate (378 mg, yield: 43%) were collected by filtration. The product was recrystallized from xylene-isopropyl ether to obtain pale yellow prisms. Melting point: 174 to 176° C.

EXAMPLE 112

In the same manner as in Example 111, ethyl 4-[N-(4-chlorobenzoylmethyl)carbamoyl]benzoate was reacted with Lawesson's reagent to obtain ethyl 4-[5-(4-chlorophenyl)-2-thiazolyl]benzoate. The product was recrystallized from xylene-isopropyl ether. Yield: 89%. Pale yellow prisms. Melting point: 167 to 168° C.

EXAMPLE 113

A mixture of ethyl 4-[2-(4-trifluoromethylphenyl)-5-thiazolyl]benzoate (360 mg), a 1N aqueous solution of sodium hydroxide (3 ml), tetrahydrofuran (5 ml) and ethanol (5 ml) was stirred at 60 to 70° C. for 1 hour. The reaction mixture was poured into 1N hydrochloric acid, and precipitated 4-[2-(4-trifluoromethylphenyl)-5-thiazolyl]benzoic acid (150 mg, yield: 45%) was collected by filtration. The product was recrystallized from acetone-isopropyl ether to obtain pale yellow prisms. Melting point: 294 to 295° C.

EXAMPLE 114

In the same manner as in Example 113, ethyl 4-[5-(4-chlorophenyl)-2-thiazolyl]benzoate was hydrolyzed to obtain 4-[5-(4-chlorophenyl)-2-thiazolyl]benzoic acid. The product was recrystallized from ethanol-water. Yield: 50%. Pale yellow prisms. Melting point: >300° C. NMR (DMSO-$d_6$) δ: 7.5–7.6 (2H, m), 7.75–7.85 (2H, m) 8.04 (4H, s), 8.40 (1H, s).

EXPERIMENTAL EXAMPLE 1

PPAR γ-RX α Heterodimer Ligand Activity

PPAR γ:RXR α:4ERPP/CHO-K1 cells obtained in Reference Example 5 were cultured in HAM F12 medium (produced by NISSUI SEIYAKU) containing 10% Fetal bovine serum (produced by Life Technologies, Inc., USA) and then inoculated to a 96-well white plate (produced by Corning Costar Corporation, USA) at the density of 2×10$^4$ cells/well, and cultured in a $CO_2$ gas incubator at 37° C. overnight.

After washing the 96 well white plate with PBS (Phosphate-buffered saline), 90 μl of HAM F12 medium containing 0.1% fatty acid-free bovine serum albumin (BSA) and 10 μl of test compound were added to each well, and the plate was cultured in a $CO_2$ gas incubator at 37° C. for 48 hours. After removing the medium, 40 μl of PIKK-AGENE 7.5 (produced by Wako Pure Chemical Industries, Ltd.) was added to the well. After stirring, the luciferase activity was determined using Lumistar (produced by BMG Labtechnologies GmbH, Germany).

A fold induction was calculated based on the luciferase activity of each test compound by estimating the luciferase activity in the non-treatment group as 1. The values of the test compound concentration and the fold induction were used to calculate the $EC_{50}$ values, the effective concentration of a test compound for 50% of the maximum fold induction, by using PRISM 2.01 (produced by GraphPad Software Inc. USA).

4-[4-(4-Chlorophenyl)-2-thiazolyl]benzoic acid as a test compound exhibited a potent PPARγ-RXRα heterodimer ligand activity at a concentration ranging from $10^{-5}$ M to $10^{-9}$ M.

EXPERIMENTAL EXAMPLE 2

Hypoglycemic and Hypolipidemic (Hypotriglyceridemic) Activities in Mice

Test compound was mixed in a powdered diet (CE-2, Japan Clea) at the concentration of 0.01%, and freely given to KKA$^y$ mice (9 to 12 weeks old, 5 mice in a group) a model of obese and non-insulin-dependent diabetes mellitus (Type 2 diabetes mellitus), for four days. This model mouse is known to exhibit pathologic profiles such as fatty liver and diabetic nephropathy in addition to hyperglycemia, hyperlipidemia, hyperinsulinemia and insulin resistance (Journal of Nutritional Science and Vitaminology, Vol.38, p.27 (1992)). During the experimental period, water was given freely Blood was obtained from orbital venous plexus, and glucose and triglyceride levels in plasma were determined enzymatically using L type Wako Glu2 (Wako Pure Chemical Industries, Ltd.) and L type Wako TG·H (Wako Pure Chemical Industries, Ltd.), respectively. 4-[4-(4-Chlorophenyl)-2-thiazolyl]benzoic acid as a test compound exhibited a potent hypoglycemic and hypolipidemic (hypotriglyceridemic) activities at a dose ranging from 0.1 to 50 mg/kg/day, although the dose depended on the intake amount of the above powdered diet.

EXPERIMENTAL EXAMPLE 3

(PPARγ-RXR α Heterodimer Ligand Activity)

PPARγ:RXRα:4ERPP/CHO-K1 cells obtained in Reference. Example 5 were cultured in HAM F12 medium (produced by NISSUI SEIYAKU) containing 10% Fetal bovine serum (produced by Life Technologies, Inc., USA) and then inoculated to a 96-well white plate (produced by Corning Costar Corporation, USA) at the density of 2×10$^4$ cells/well, and cultured in a $CO_2$ gas incubator at 37° C. overnight.

After washing the 96 well white plate with PBS (Phosphate-buffered saline), 90 μl of HAM F12 medium containing 0.1% fatty acid-free bovine serum albumin (BSA) and 10 μl of test compound were added to each well, and the plate was cultured in a $CO_2$ gas incubator at 37° C. for 48 hours. After removing the medium, 40 μl of PIKK-AGENE 7.5 produced by Wako Pure Chemical Industries, Ltd.) was added to the well. After stirring, the luciferase activity was determined using Lumistar (produced by BMG Labtechnologies Gmbh, Germany).

A fold induction was calculated based on the luciferase activity of each test compound by estimating the luciferase activity in the non-treatment group as 1. The values of the test compound concentration and the fold induction were used to calculate the $EC_{50}$ values, the effective concentration of a test compound for 50% of the maximum induction, by using PRISM 2.01 (produced by GraphPad Software Inc. USA). The results are shown in [Table 1].

TABLE 1

| Ex. No. of test compound | EC50 ($\mu$M) |
| --- | --- |
| 8 | 0.092 |
| 9 | 0.023 |
| 55 | 0.068 |
| 64 | 0.31 |
| 72 | 0.0006 |
| 95 | 0.10 |
| 96 | 0.0019 |
| 100 | 0.0051 |
| 110 | 0.048 |
| 113 | 0.060 |

As described above, the compound of the invention exhibited a potent PPAR$\gamma$-RXR$\alpha$ heterodimer ligand activity.

EXPREIMENTAL EXAMPLE 4

Hypoglycemic and Hypolipidemic (Hypotriglyceridemic) Activities in Mice

Test compound was mixed in a powdered diet (CE-2, Japan Clea) at the concentration of 0.01%, and freely given to KKA$^y$ mice (9 to 12 weeks old, 5 mice in a group), a model of obese and.non-insulin-dependent diabetes mellitus (Type 2 diabtes mellitus), for four days. During this period, water was given freely. Blood was obtained from orbital venous plexus, and glucose and triglyceride levels in plasma were determined enzymatically using L type Wako Glu2 (Wako Pure Chemical Industries, Ltd.) and L type Wako TG·H (Wako Pure Chemical Industries, Ltd.), respectively.

The value of each treatment group is represented as reduction rate (%) compared with the non-treatment group, which is shown in [Table 2].

TABLE 2

| Ex. No. of test compound | Hypoglycemic effect (%) | Hypolipidemic effect (%) |
| --- | --- | --- |
| 9 | 51 | 67 |
| 55 | 70 | 86 |
| 64 | 68 | 88 |
| 110 | 73 | 87 |
| 113 | 45 | 53 |

As described above, the compound of the invention has a potent hypoglycemic and hypolipidemic effects, and it is useful as an agent for preventing and treating diabetes, hyperlipidemia, impaired glucose tolerance, etc.

PREPARATION EXAMPLE 1

Production of Capsules

| | |
| --- | --- |
| 1) 4-[4-(4-Trifluoromethylphenyl)-2-thiazolyl]benzoic acid | 30 mg |
| 2) Microcrystalline cellulose | 10 mg |
| 3) Lactose | 19 mg |
| 4) Magnesium stearate | 1 mg |
| Total | 60 mg |

1), 2), 3) and 4) are admixed and filled in a gelatin capsule.

PREPARATION EXAMPLE 2

Production of Tablets

| | |
| --- | --- |
| 1) 4-[4-(4-Trifluoromethylphenyl)-2-thiazolyl]benzoic acid | 30 mg |
| 2) Lactose | 50 g |
| 3) Corn starch | 15 g |
| 4) Carboxymethylcellulose calcium | 44 g |
| 5) Magnesium stearate | 1 g |
| 1000 Tablets, Total | 140 g |

The whole amounts of 1), 2) and 3) and 30 g of 4) a kneaded with water, dried in vacuum, and then granulated. The granular mixture is admixed with 14 g of 4) and 1 g of 5) and the resulting mixture is tableted using a tableting machine, Thus, 1000 tablets each containing 30 mg of Compound (7) are obtained.

INDUSTRIAL APPLICABILITY

A pharmaceutical composition of the invention is low in toxicity, and can be employed, for instance, as an agent for preventing or treating diabetes (e.g., insulin-dependent diabetes, non-insulin-dependent diabetes, gestational diabetes), an agent for preventing or treating hyperlipidemia (e.g., hypertriglyceridemia, hypercholesterolemia, hypo-HDL-cholesterolemia), an insulin sensitivity enhancing agent, an insulin resistance improving agent, an agent for preventing or treating impaired glucose tolerance (IGT), and an agent for preventing transition from impaired glucose tolerance to diabetes.

Further, a pharmaceutical composition of the invention cain be used, for instance, as an agent for preventing or treating diabetic complications (e.g., neuropathy, nephropathy, retinopathy, cataract, macroangiopathy, osteopenia), obesity, osteoporosis, cachexia (e.g., carcinomatous cachexia tuberculous cachexia, diabetic cachexia, hemopathic cachexia, endocrinopathic cachexia, infectious, cachexia or cachexia induced by acquired immunodeficiency syndrome), fatty liver, hypertension, polycystic ovary syndrome, renal diseases (e.g., diabetic nephropathy, glomerular nephritis, glomerulosclerosis, nephrotic syndrome, hypertensive nephrosclerosis, terminal renal disorder), muscular dystrophy, myocardiac infarction, angina pectoris, cerebral infarction, insulin resistant syndrome, syndrome X, hyperinsulinemia-induced sensory disorder, tumor (e.g., leukemia, breast cancer, prostate cancer, skin cancer), arteriosclerosis (e.g., atherosclerosis) and as a pharmaceutical for controllineg appetite or food intake.

SEQUENCE LISTING

<160> NUMBER OF SEQ ID NOS: 8

<210> SEQ ID NO 1
<211> LENGTH: 33
<212> TYPE: DNA
<213> ORGANISM: Artificial Sequence
<220> FEATURE:
<223> OTHER INFORMATION: This represents a synthetic DNA primer prepared
      with reference to the base sequence of PPAR (gamma) gene

<400> SEQUENCE: 1
gtgggtaccg aaatgaccat ggttgacaca gag                                    33

<210> SEQ ID NO 2
<211> LENGTH: 33
<212> TYPE: DNA
<213> ORGANISM: Artificial Sequence
<220> FEATURE:
<223> OTHER INFORMATION: This represents a synthetic DNA primer prepared
      with reference to the base sequence of PPAR (gamma) gene

<400> SEQUENCE: 2
ggggtcgacc aggactctct gctagtacaa gtc                                    33

<210> SEQ ID NO 3
<211> LENGTH: 33
<212> TYPE: DNA
<213> ORGANISM: Artificial Sequence
<220> FEATURE:
<223> OTHER INFORMATION: This represents a synthetic DNA primer prepared
      with reference to the base sequence of RXR (alpha) gene

<400> SEQUENCE: 3
ttagaattcg acatggacac caaacatttc ctg                                    33

<210> SEQ ID NO 4
<211> LENGTH: 33
<212> TYPE: DNA
<213> ORGANISM: Artificial Sequence
<220> FEATURE:
<223> OTHER INFORMATION: This represents a synthetic DNA primer prepared
      with reference to the base sequence of RXR (alpha) gene

<400> SEQUENCE: 4
cccctcgagc taagtcattt ggtgcggcgc ctc                                    33

<210> SEQ ID NO 5
<211> LENGTH: 36
<212> TYPE: DNA
<213> ORGANISM: Artificial Sequence
<220> FEATURE:
<223> OTHER INFORMATION: This represents a synthetic 5'-terminal
      phosphorylated DNA used to prepare a DNA fragment containing
      PPAR-responding element (PPRE) of an acyl CoA oxidase

<400> SEQUENCE: 5
tcgacagggg accaggacaa aggtcacgtt cgggag                                 36

<210> SEQ ID NO 6
<211> LENGTH: 36
<212> TYPE: DNA
<213> ORGANISM: Artificial Sequence
<220> FEATURE:
<223> OTHER INFORMATION: This represents a synthetic 5'-terminal
      phosphorylated DNA used to prepare a DNA fragment containing
      PPAR-responding element (PPRE) of an acyl CoA oxidase

```
<400> SEQUENCE: 6
tcgactcccg aacgtgacct ttgtcctggt cccctg                    36

<210> SEQ ID NO 7
<211> LENGTH: 28
<212> TYPE: DNA
<213> ORGANISM: Artificial Sequence
<220> FEATURE:
<223> OTHER INFORMATION: This represents a synthetic DNA primer prepared
      with reference to the base sequence of the promoter region of
      thymidine kinase

<400> SEQUENCE: 7
cccagatctc cccagcgtct tgtcattg                             28

<210> SEQ ID NO 8
<211> LENGTH: 28
<212> TYPE: DNA
<213> ORGANISM: Artificial Sequence
<220> FEATURE:
<223> OTHER INFORMATION: This represents a synthetic DNA primer prepared
      with reference to the base sequence of the promoter region of
      thymidine kinase

<400> SEQUENCE: 8
tcaccatggt caagcttta agcgggtc                              28
```

What is claimed is:

1. An oxazole compound represented by formula (I-1):

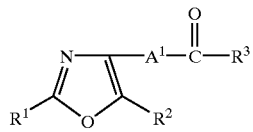

wherein $R^1$ is an aromatic hydrocarbon group or an aromatic heterocyclic group, each of which may be substituted;

$R^2$ is hydrogen or an unsubstituted or substituted hydrocarbon group;

$A^1$ is an aromatic hydrocarbon group or thienyl group, each of which may be substituted;

$R^3$ is a group represented by the formula:
- $-OR^5$ wherein $R^5$ is hydrogen or an unsubstituted or substituted hydrocarbon group,
- or $-NR^6R^7$ wherein $R^6$ and $R^7$ are same or different and each is hydrogen or an unsubstituted or substituted hydrocarbon group, or $R^6$ and $R^7$ may be taken together with an adjacent nitrogen atom to form a ring, or its salt.

2. An oxazole compound represented by formula (I-2):

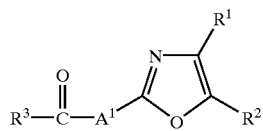

wherein $R^1$ is an aromatic hydrocarbon group or an aromatic heterocyclic group, each of which may be substituted;

$R^2$ is hydrogen or an unsubstituted or substituted hydrocarbon group;

$A^1$ is an aromatic hydrocarbon group or thienyl group, each of which may be substituted;

$R^3$ is a group represented by the formula:
- $-OR^5$ wherein $R^5$ is hydrogen or an unsubstituted or substituted hydrocarbon group,
- or $-NR^6R^7$ wherein $R^6$ and $R^7$ are same or different and each is hydrogen or an unsubstituted or substituted hydrocarbon group,
- or $R^6$ and $R^7$ may be taken together with an adjacent nitrogen atom to form a ring, provided that compounds represented by the formulae:

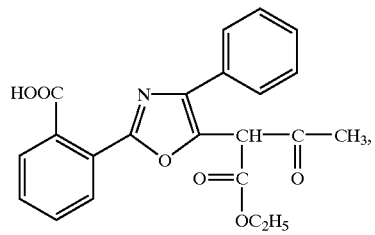

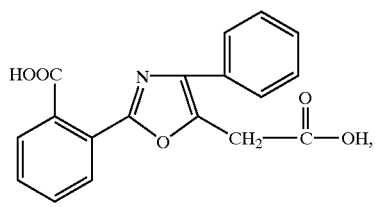

-continued

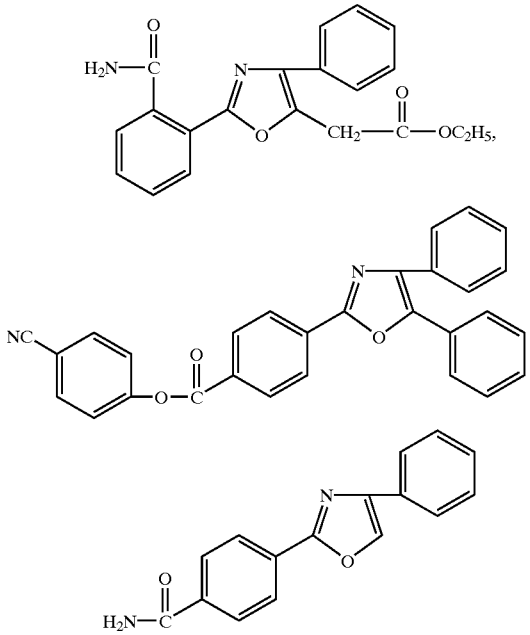

are excluded, or its salt.

3. An oxazole compound or its salt according to claim 2 wherein $R^2$ is hydrogen or an unsubstituted or substituted non-aromatic hydrocarbon group except for a non-aromatic hydrocarbon group which is substituted by a non-esterified or esterified carboxyl group, and $R^3$ is a group represented by the formula: —$OR^5$.

4. An oxazole compound represented by formula (I-3):

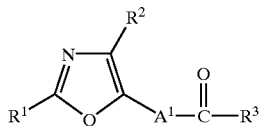

(I-3)

wherein $R^1$ is an aromatic hydrocarbon group or an aromatic heterocyclic group, each of which may be substituted;
$R^2$ is hydrogen or an unsubstituted or substituted hydrocarbon group;
$A^1$ is a phenyl group having a —$COR^3$ group in a meta- or para-position;
$R^3$ is OH;
or its salt.

5. An imidazole compound represented by formula (I-4):

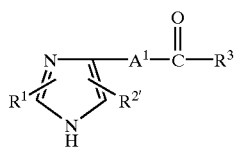

(I-4)

wherein $R^1$ is an aromatic hydrocarbon group or aromatic heterocyclic group, each of which may be substituted;
$R^{2'}$ is hydrogen or an unsubstituted or substituted non-aromatic hydrocarbon group;
$A^1$ is an aromatic hydrocarbon group or thienyl group, each of which may be substituted;

$R^3$ is a group represented by the formula:
—$OR^5$ wherein $R^5$ is hydrogen or an unsubstituted or substituted hydrocarbon group,
or —$NR^6R^7$ wherein $R^6$ and $R^7$ are same or different and each is hydrogen or an unsubstituted or substituted hydrocarbon group,
or $R^6$ and $R^7$ may be taken together with an adjacent nitrogen atom to form a ring,
provided that a compound represented by the formula:

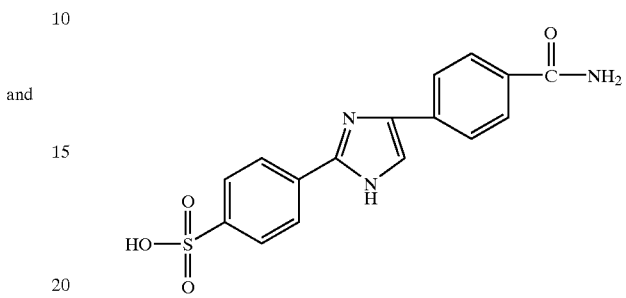

is excluded, or its salt.

6. An imidazole compound or its salt according to claim 5 wherein $R^1$ is an unsubstituted or substituted aromatic hydrocarbon group except for an aromatic hydrocarbon group substituted by sulfo group.

7. An imidazole compound represented by formula (I-5):

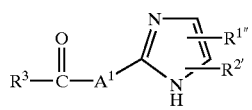

(I-5)

wherein $R^{1''}$ is an unsubstituted or substituted aromatic hydrocarbon group and said aromatic hydrocarbon group does not form a condensed ring;
$R^{2'}$ is hydrogen or an unsubstituted or substituted non-aromatic hydrocarbon group;
$A^1$ is an aromatic hydrocarbon group or thienyl group, each of which may be substituted;
$R^3$ is a group represented by the formula: —$OR^5$ wherein $R^5$ is hydrogen or an unsubstituted or substituted hydrocarbon group,
or its salt.

8. A thiazole compound represented by formula (I-6):

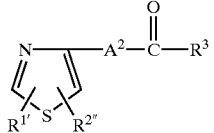

(I-6)

wherein $R^{1'}$ is an unsubstituted or substituted aromatic hydrocarbon group except for an aromatic hydrocarbon group substituted by a group having an intervening hetero atom;
$R^{2''}$ is hydrogen or an alkyl group;
$A^2$ is an unsubstituted or substituted aromatic hydrocarbon group except for an aromatic hydrocarbon group substituted by a group having an intervening hetero atom;
$R^3$ is a group represented by the formula: —$OR^5$ wherein $R^5$ is hydrogen or an unsubstituted or substituted hydrocarbon group, or —NR$^6$R$^7$ wherein R$^6$ and R$^7$ are same or different and each is hydrogen or an unsubstituted or substituted hydrocarbon group, or R$^6$ and R$^7$ may be taken together with an adjacent nitrogen atom to form a ring, provided that compounds represented by the formulae:

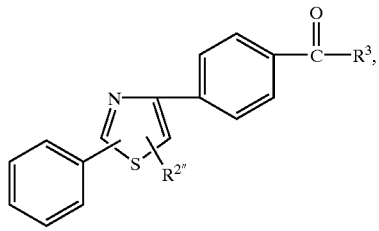

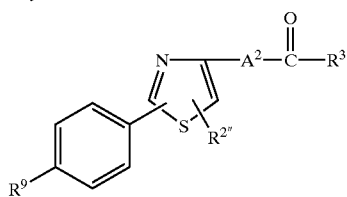

wherein R$^9$ is methoxy group, methyl group, chlorine, t-butyl group or trifluoromethyl group and,

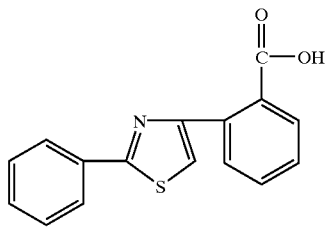

and its HBr salt are excluded,
or its salt.

9. A thiazole derivative or its salt according to claim 8 wherein R$^{1'}$ is an aromatic hydrocarbon group having at least two substituents.

10. A thiazole derivative or its salt according to claim 8 wherein R$^{1'}$ is phenyl group having a substituent in an ortho- or meta-position.

11. A thiazole compound represented by formula (I-7):

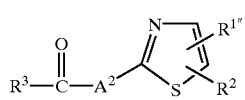

(I-7)

wherein R$^{1''}$ is an aromatic hydrocarbon group having at least two substituents;

R$^2$ is hydrogen or an unsubstituted or substituted hydrocarbon group;

A$^2$ is a phenyl group having —COR$^3$ group in an ortho-position;

R$^3$ is a group represented by the formula:
—OR$^5$ wherein R$^5$ is hydrogen or an unsubstituted or substituted hydrocarbon group,
or —NR$^6$R$^7$ wherein R$^6$ and R$^7$ are same or different and each is hydrogen or an unsubstituted or substituted hydrocarbon group, or R$^6$ and R$^7$ may be taken together with an adjacent nitrogen atom to form a ring, or its salt.

12. A thiazole compound or its salt according to claim 11 wherein R$^2$ is an unsubstituted or substituted hydrocarbon group.

13. A compound selected from the group consisting of:
i) 4-[4-(4-chlorophenyl)-2-oxazolyl]benzoic acid,
ii) 4-[4-(4-trifluoromethylphenyl)-2-oxazolyl]benzoic acid,
iii) 4-[4-(4-trifluoromethylphenyl)-2-thiazolyl]benzoic acid,
iv) 4-[4-(4-trifluoromethoxyphenyl)-2-thiazolyl]benzoic acid,
v) 3-[4-(4-isopropylphenyl)-2-thiazolyl]benzoic acid,
vi) 3-[4-(4-ethoxyphenyl)-2-thiazolyl]benzoic acid,
vii) 4-[2-(4-trifluoromethylphenyl)-5-oxazolyl]benzoic acid,
viii) 4-[2-(4-trifluoromethylphenyl)-5-thiazolyl]benzoic acid,
ix) 3-[4-(2,5-dimethyl-3-furyl)-2-thiazolyl]benzoic acid,
x) 3-[4-(2,5-dichloromethyl-3-thienyl)-2-thiazolyl]benzoic acid, and salts thereof.

14. A pharmaceutical composition comprising at least one compound selected from the group consisting of
4-[4-(4-chlorophenyl)-2-oxazolyl]benzoic acid,
4-[4-(4-trifluoromethylphenyl)-2-oxazolyl]benzoic acid,
4-[4-(4-trifluoromethylphenyl)-2-thiazolyl]benzoic acid,
4-[4-(4-trifluoromethoxyphenyl)-2-thiazolyl]benzoic acid,
3-[4-(4-isopropylphenyl)-2-thiazolyl]benzoic acid,
3-[4-(4-ethoxyphenyl)-2-thiazolyl]benzoic acid,
4-[2-(4-trifluoromethylphenyl)-5-oxazolyl]benzoic acid,
4-[2-(4-trifluoromethylphenyl)-5-thiazolyl]benzoic acid,
3-[4-(2,5-dimethyl-3-furyl)-2-thiazolyl]benzoic acid,
3-[4-(2,5-dichloromethyl-3-thienyl)-2-thiazolyl]benzoic acid,
and salts therof;
and a pharmacologically acceptable carrier.

15. A method for regulating peroxisome proliferator-activated receptor function comprising administering pharmaceutically effective amount of a 1,3-azole compound represented by formula (I):

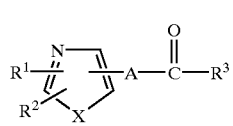

(I)

wherein R$^1$ is an aromatic hydrocarbon group or an aromatic heterocyclic group, each of which may be substituted;

R$^2$ is hydrogen or an unsubstituted or substituted hydrocarbon group;

X is O, S or a group represented by the formula: —NR$^4$— wherein R$^4$ is hydrogen or an unsubstituted or substituted alkyl group;

A is an aromatic hydrocarbon group or an aromatic heterocyclic group, each of which may be substituted;

R$^3$ is a group represented by the formula:
—OR$^5$ wherein R$^5$ is hydrogen or an unsubstituted or substituted hydrocarbon group, or —NR⁶R⁷ wherein $R^6$ and $R^7$ are same or different and each is hydrogen or an unsubstituted or substituted hydrocarbon group, or $R^6$ and $R^7$ may be taken together with an adjacent nitrogen atom to form a ring, provided that compounds represented by the formulae:

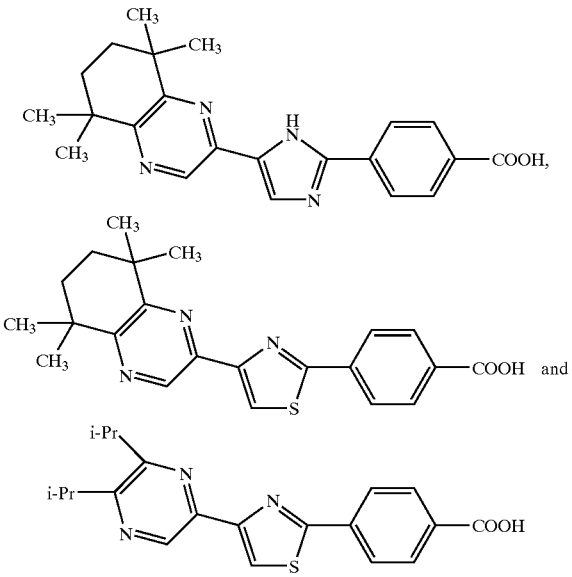

are excluded, or its salt to a mammal in need thereof.

16. The method of claim 15 wherein $R^1$ of said 1,3-azole compound is an aromatic hydrocarbon group or an aromatic heterocyclic group which does not contain a nitrogen atom, each of which may be substituted.

17. The method of claim 15, wherein regulation of peroxisome proliferator-activated receptor function is for treating diabetes.

18. The method of claim 15, wherein regulation of peroxisome proliferator-activated receptor function is for improving lipid metabolism.

19. The method of claim 15, wherein regulation of peroxisome proliferator-activated receptor function is for treating hyperlipidemia.

20. The method of claim 15, wherein regulation of peroxisome proliferator-activated receptor function is for treating obesity.

21. The method of claim 15, wherein regulation of peroxisome proliferator-activated receptor function is for enhancing insulin sensitivity.

22. The method of claim 15, wherein regulation of peroxisome proliferator-activated receptor function is for improving insulin resistance.

23. The method of claim 15, wherein regulation of peroxisome proliferator-activated receptor function is for treating impaired glucose tolerance.

24. A method for regulating a peroxisome proliferator-activated receptor function comprising administering a pharmaceutically effective amount of at least one compound selected from the group consisting of:

4-[4-(4-chlorophenyl)-2-oxazolyl]benzoic acid,
4-[4-(4-trifluoromethylphenyl)-2-oxazolyl]benzoic acid,
4-[4-(4-trifluoromethylphenyl)-2-thiazolyl]benzoic acid,
4-[4-(4-trifluoromethoxyphenyl)-2-thiazolyl]benzoic acid,
3-[4-(4-isopropylphenyl)-2-thiazolyl]benzoic acid,
3-[4-(4-ethoxyphenyl)-2-thiazolyl]benzoic acid,
4-[2-(4-trifluoromethylphenyl)-5-oxazolyl]benzoic acid,
4-[2-(4-trifluoromethylphenyl)-5-thiazolyl]benzoic acid,
3-[4-(2,5-dimethyl-3-furyl)-2-thiazolyl]benzoic acid,
3-[4-(2,5-dichloromethyl-3-thienyl)-2-thiazolyl]benzoic acid and salts thereof to a mammal in need thereof.

25. The method of claim 15, wherein said peroxisome proliferator-activated receptor is PPARγ.

* * * * *